US009828428B2

(12) United States Patent
Ma et al.

(10) Patent No.: US 9,828,428 B2
(45) Date of Patent: Nov. 28, 2017

(54) ANTI-IL-13 RECEPTOR ALPHA 2 ANTIBODIES AND ANTIBODY-DRUG CONJUGATES

(71) Applicant: Pfizer Inc., New York, NY (US)

(72) Inventors: Dangshe Ma, Millwood, NY (US); Fang Jin, Waban, MA (US); Lioudmila Gennadievna Tchistiakova, Stoneham, MA (US); Puja Sapra, River Edge, NJ (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 14/439,897

(22) PCT Filed: Oct. 30, 2013

(86) PCT No.: PCT/IB2013/059786
§ 371 (c)(1),
(2) Date: Apr. 30, 2015

(87) PCT Pub. No.: WO2014/072888
PCT Pub. Date: May 15, 2014

(65) Prior Publication Data
US 2015/0266962 A1 Sep. 24, 2015

Related U.S. Application Data

(60) Provisional application No. 61/723,545, filed on Nov. 7, 2012, provisional application No. 61/749,610, filed on Jan. 7, 2013, provisional application No. 61/886,156, filed on Oct. 3, 2013, provisional application No. 61/889,179, filed on Oct. 10, 2013.

(51) Int. Cl.
*C07K 16/28* (2006.01)
*A61K 47/48* (2006.01)
*G01N 33/574* (2006.01)
*A61K 39/395* (2006.01)
*A61K 39/00* (2006.01)

(52) U.S. Cl.
CPC .... *C07K 16/2866* (2013.01); *A61K 47/48384* (2013.01); *A61K 47/48546* (2013.01); *A61K 47/48561* (2013.01); *A61K 47/48715* (2013.01); *G01N 33/57492* (2013.01); *A61K 2039/505* (2013.01); *C07K 2317/24* (2013.01); *C07K 2317/33* (2013.01); *C07K 2317/56* (2013.01); *C07K 2317/565* (2013.01); *C07K 2317/76* (2013.01); *C07K 2317/77* (2013.01); *C07K 2317/92* (2013.01); *C07K 2317/94* (2013.01); *G01N 2333/7155* (2013.01)

(58) Field of Classification Search
None
See application file for complete search history.

(56) References Cited

U.S. PATENT DOCUMENTS

| 8,613,925 | B2 | 12/2013 | Nash et al. |
| 8,828,401 | B2 | 9/2014 | Doroski et al. |
| 2011/0110955 | A1 | 5/2011 | Debinski et al. |
| 2013/0323234 | A1 | 12/2013 | Laurent et al. |
| 2014/0056915 | A1 | 2/2014 | Nash et al. |

FOREIGN PATENT DOCUMENTS

| WO | 02/17968 A2 | 3/2002 |
| WO | 2004/087758 A2 | 10/2004 |
| WO | 2005/042028 A2 | 5/2005 |
| WO | 2012/007896 A1 | 1/2012 |
| WO | 2013/072813 A2 | 5/2013 |
| WO | 2013/093809 A1 | 6/2013 |

OTHER PUBLICATIONS

Wang et al. Nuc. Acids Research, 1999; vol. 27, pp. 4609-4618.*
Kaufman et al, Blood, 1999, vol. 94, pp. 3178-3184.*
Wigley et al. Reprod Fert Dev, 1994, vol. 6: 585-588.*
Campbell et al. , Theriology 47(1): 63-72, 1997.*
Rubanyi, biol. Aspects Med. (2001) 22:113-142.*
Juengst (British Medical Journal (2003) vol. 326, pp. 1410-1411.*
Crystal, R. Science, vol. 270, 1995, pp. 404-410.*
Bernard et al, "Expression of Interleukin 13 Receptor in Glioma and Renal Cell Carcinoma: IL13Rα2 as a Decoy Receptor for IL13". Laboratory Investigation 81(9):1223-1231 (2001).
Bernardi et al, "Immunonanoshells for targeted photothermal ablation in medulloblastoma and glioma: an in vitro evaluation using human cell lines", Journal of Neuro-Oncology 86(2):165-172 (2008).
Debinski et al, "Receptor for Interleukin 13 Is a Marker and Therapeutic Target for Human High-Grade Gliomas", Clinical Cancer Research 5:985-990 (1999).
Donaldson et al, "The Murine IL-13 Receptor α2: Molecular Cloning, Characterization, and Comparison with Murine IL-13 Receptor α1", The Journal of Immunology 161:2317-2324 (1998).
Fujisawa et al—Targeting IL-13Rα2 in human pancreatic ductal adenocarcinoma with combination therapy of IL-13-PE and gemcitabine, International Journal of Cancer 128(5):1221-1231 (2011).
Jarboe et al, "Expression of Interleukin-13 Receptor α2 in Glioblastoma Multiforme: Implications for Targeted Therapies", Cancer Research 67:7983-7986 (2007).
Kioi et al—Targeting IL-13Rα2-positive cancer with a novel recombinant immunotoxin composed of a single-chain antibody and mutated Pseudomonas exotoxin, Molecular Cancer Therapeutics 7(6):1579-1587 (2008).
Lupardus et al, "Molecular Basis for Shared Cytokine Recognition Revealed in the Structure of an Unusually High Affinity Complex between IL-13 and IL-13Rα2", Structure 18(3):332-342 (2010).

(Continued)

Primary Examiner — Joanne Hama
Assistant Examiner — Fozia Hamud
(74) Attorney, Agent, or Firm — Maria V. Marucci

(57) ABSTRACT

Disclosed herein are anti-IL-13-Rα2 antibodies and antibody drug conjugates and methods for preparing and using the same.

23 Claims, 11 Drawing Sheets

(56) References Cited

OTHER PUBLICATIONS

Marie et al, "Maternal embryonic leucine zipper kinase transcript abundance correlates with malignancy grade in human astrocytomas", International Journal of Cancer 122:807-815 (2008).
PCT International Search Report and Written Opinion for PCT/IB2013/059786 issued Feb. 25, 2014.
Shimamura et al, "Interleukin 13 Mediates Signal Transduction through Interleukin 13 Receptor α2 in Pancreatic Ductal Adenocarcinoma: Role of IL-13 Pseudomonas Exotoxin in Pancreatic Cancer Therapy", Clinical Cancer Research 16:577-586 (2010).
Wykosky et al, "Interleukin-13 Receptor α2, EphA2, and Fos-Related Antigen 1 as Molecular Denominators of High-Grade Astrocytomas and Specific Targets for Combinatorial Therapy", Clinical Cancer Research 14:199-208 (2008).
Takenouchi et al, "Epigenetic Modulation Enhances the Therapeutic Effect of Anti-IL-13Rβ2 Antibody in Human Mesothelioma Xenografts", Clinical Cancer Research 17(9):2819-2829 (2011).

* cited by examiner

FIG. 4A

SEQ ID NO: 1 hu08-VH v1.0
EVQLVESGGGLVQPGGSLRLSCAASGFTFSRNGMSWVRQAPGKGLEWVATVSSGGSYIYYADSVKGRFTISRDNAK
NSLYLQMNSLRAEDTAVYYCARQGTTALATRFFDVWGQGTLVTVSS

SEQ ID NO: 2 hu08 HCDR1
SRNGMS

SEQ ID NO: 3 hu08 HCDR2
TVSSGGSYIYYADSVKG

SEQ ID NO: 4 hu08 HCDR3
QGTTALATRFFDV

SEQ ID NO: 5 hu08-VL v1.0
DIQMTQSPSSLSASVGDRVTITCKASQDVGTAVAWYQQKPGKAPKLLIYSASYRSTGVPSRFSGSGSGTDFTLTISSL
QPEDFATYYCQHHYSAPWTFGGGTKVEIK

SEQ ID NO: 6 hu08 LCDR1
KASQDVGTAVA

SEQ ID NO: 7 hu08 LCDR2
SASYRST

SEQ ID NO: 8 hu08 LCDR3
QHHYSAPWT

SEQ ID NO: 9 hu07-VH v1.0
EVQLVESGGGLVQPGGSLRLSCAASGFTFTKYGVHWVRQAPGKGLEWVAVKWAGGSTDYNSALMSRFTISRDNAK
NSLYLQMNSLRAEDTAVYYCARDHRDAMDYWGQGTLVTVSS

SEQ ID NO: 10 hu07 HCDR1
TKYGVH

SEQ ID NO: 11 hu07 HCDR2
VKWAGGSTDYNSALMS

SEQ ID NO: 12 hu07 HCDR3
DHRDAMDY

SEQ ID NO: 13 hu07-VL v1.0
DIQMTQSPSSLSASVGDRVTITCTASLSVSSTYLHWYQQKPGKAPKLLIYSTSNLASGVPSRFSGSGSGTDFTLTISSL
QPEDFATYYCHQYHRSPLTFGGGTKVEIK

SEQ ID NO: 14 hu07 LCDR1
TASLSVSSTYLH

SEQ ID NO: 15 hu07 LCDR2
STSNLAS

SEQ ID NO: 16 hu07 LCDR3
HQYHRSPLT

FIG. 4B

SEQ ID NO: 17 hu08-VH v1.0
GAGGTGCAGCTGGTGGAGTCTGGCGGCGGACTGGTGCAGCCTGGCGGCTCTCTGAGACTGTCTTGTGCCGCC
TCCGGCTTCACCTTCAGTAGGAATGGCATGTCTTGGGTGAGGCAGGCCCCTGGCAAGGGCCTGGAGTGGGTGG
CCACCGTTAGTAGTGGTGGTAGTTACATCTACTATGCAGACAGTGTGAAGGGGCGGTTCACCATCTCCAGGGAC
AACGCCAAGAACTCCCTGTACCTCCAGATGAACTCCCTGAGGGCCGAGGATACCGCCGTGTACTACTGTGCCA
GACAAGGGACTACGGCACTAGCTACGAGGTTCTTCGATGTCTGGGGCCAGGGCACCCTGGTGACCGTGTCCTC
T

SEQ ID NO: 18 hu08-VL v1.0
GACATCCAGATGACCCAGTCCCCCTCTTCTCTGTCTGCCTCTGTGGGCGACAGAGTGACCATCACCTGTAAGGC
CAGTCAGGATGTAGGTACTGCTGTAGCCTGGTATCAGCAGAAGCCTGGCAAGGCTCCCAAGCTGCTGATCTACT
CGGCATCCTACCGGTCCACTGGCGTGCCTTCCAGATTCTCCGGCTCTGGCTCTGGCACCGATTTCACCCTGACC
ATCTCCTCCCTCCAGCCTGAGGATTTCGCCACCTACTACTGCCAGCACCATTATAGTGCTCCGTGGACGTTTGG
CGGCGGAACAAAGGTGGAGATCAAG

SEQ ID NO: 19 hu08-VH v1.1
EVQLVESGGGLVQPGGSLRLSCAASGFTF<u>SRNGMS</u>WVRQTPDKRLEWVA<u>TVSSGGSYIYYADSVKG</u>RFTISRDNAK
NSLYLQMSSLRAEDTAVYYCAR<u>QGTTALATRFFDV</u>WGQGTLVTVSS

SEQ ID NO: 20 hu08-VH v1.1
GAGGTGCAGCTGGTGGAGTCTGGCGGCGGACTGGTGCAGCCTGGCGGCTCTCTGAGACTGTCTTGTGCCGCC
TCCGGCTTCACCTTCAGTAGGAATGGCATGTCTTGGGTGAGGCAGACCCCTGACAAGCGCCTGGAGTGGGTGG
CCACCGTTAGTAGTGGTGGTAGTTACATCTACTATGCAGACAGTGTGAAGGGGCGGTTCACCATCTCCAGGGAC
AACGCCAAGAACTCCCTGTACCTCCAGATGAGCTCCCTGAGGGCCGAGGATACCGCCGTGTACTACTGTGCCA
GACAAGGGACTACGGCACTAGCTACGAGGTTCTTCGATGTCTGGGGCCAGGGCACCCTGGTGACCGTGTCCTC
T
SEQ ID NO: 21 hu08-VL v1.1
DIQMTQSPSSLSASVGDRVTITC<u>KASQDVGTAVA</u>WYQQIPGKAPKLLIY<u>SASYRST</u>GVPDRFSGSGSGTDFSFIISSLQ
PEDFATYYC<u>QHHYSAPWT</u>FGGGTKVEIK

SEQ ID NO: 22 hu08-VL v1.1
GACATCCAGATGACCCAGTCCCCCTCTTCTCTGTCTGCCTCTGTGGGCGACAGAGTGACCATCACCTGTAAGGC
CAGTCAGGATGTAGGTACTGCTGTAGCCTGGTATCAGCAGATCCCTGGCAAGGCTCCCAAGCTGCTGATCTACT
CGGCATCCTACCGGTCCACTGGCGTGCCTGACAGATTCTCCGGCTCTGGCTCTGGCACCGATTTCTCCTTTATC
ATCTCCTCCCTCCAGCCTGAGGATTTCGCCACCTACTACTGCCAGCACCATTATAGTGCTCCGTGGACGTTTGG
CGGCGGAACAAAGGTGGAGATCAAG

FIG. 4C

SEQ ID NO: 23 mu08 VH
EVQLVESGGDLVRPGGSLQLSCAASGFTF<u>SRNGMS</u>WVRQTPDRRLEWVA<u>TVSSGGSYIYYADSVKG</u>RFTISRDNAR
NTLYLQMSSLKSEDTAMYYCAR<u>QGTTALATRFFD</u>VWGAGTTVTVSS

SEQ ID NO: 24 mu08 VL
DIVMTQSHKFISTSVGDRVSITC<u>KASQDVGTAVA</u>WYQQIPGQSPKLLIY<u>SASYRST</u>
GIPDRFTGSGSGTDFSFIISSVQAEDLALYYC<u>QHHYSAPWT</u>FGGGTTLDIK

SEQ ID NO: 25 mu07 VH
QVQLKESGPGLVAPSQSLSINCTVSGFSL<u>TKYGVH</u>WIRQSPGKGLEWLG<u>VKWAGGSTDYNSALMS</u>RLTISKDNNKS
QVFLKMNSLQSDDSAMYYCAR<u>DHRDAMDY</u>WGQGTSVTVSS

SEQ ID NO: 26 mu07 VL
QVVLTQSPAIMSASPGERVTMTC<u>TASLSVSSTYLH</u>WYHQKPGSSPKLWIY<u>STSNLAS</u>GVPARFSGSGSGTSYSLTISS
MEAEDAATYYC<u>HQYHRSPLT</u>FGSGTKLELK

SEQ ID NO: 27 cyno IL-13Ra2
DTEIKVNPPQDFEIVDPGYLGYLYLQWQPPLSLDNFKECTVEYELKYRNIGSETWTTIITKNLHYKDGFDLNKGIEAKIH
TLLPWQCTNGSEVQSSWAEATYWISPQGIPETKVQDMDCVYYNWQYLLCSWKPGIGVLLDTNYNLFYWYEGLDRAL
QCVDYIKVDGQNIGCRFPYLESSDYKDFYICVNGSSETKPIRSSYFTFQLQNIVKPLPPVCLTCTQESLYEIKLKWSIPL
GPIPARCFVYEIEIREDDTTLVTTTVENETYTLKITNETRQLCFVVRSKVNIYCSDDGIWSEWSDKQCWEVEELLKKTLL
LFLLPFGFILILVIFVTGLLL

SEQ ID NO: 28 hu08 HC 1.0 L443C
EVQLVESGGGLVQPGGSLRLSCAASGFTF<u>SRNGMS</u>WVRQAPGKGLEWVA<u>TVSSGGSYIYYADSVKG</u>RFTISRDNAK
NSLYLQMNSLRAEDTAVYYCAR<u>QGTTALATRFFD</u>VWGQGTLVTVSSASTKGPSVFPLAPSSKSTSGGTAALGCLVKD
YFPEPVTVSWNSGALTSGVHTFPAVLQSSGLYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSCSPGK

FIG. 4D

SEQ ID NO: 29 hu08 HC 1.0 Q347C
EVQLVESGGGLVQPGGSLRLSCAASGFTF<u>SRNGMS</u>WVRQAPGKGLEWVA<u>TVSSGGSYIYYADSVK</u>GRFTISRDNAK
NSLYLQMNSLRAEDTAVYYCAR<u>QGTTALATRFFDV</u>WGQGTLVTVSSASTKGPSVFPLAPSSKSTSGGTAALGCLVKD
YFPEPVTVSWNSGALTSGVHTFPAVLQSSGLYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPCVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLSPGK

SEQ ID NO: 30 hu08 KC 1.0 kA111C
DIQMTQSPSSLSASVGDRVTITC<u>KASQDVGTAVA</u>WYQQKPGKAPKLLIY<u>SASYRST</u>GVPSRFSGSGSGTDFTLTISSL
QPEDFATYYC<u>QHHYSAPWT</u>FGGGTKVEIKRTVACPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSFNRGEC

SEQ ID NO: 31 hu08 KC 1.0 kK183C
DIQMTQSPSSLSASVGDRVTITC<u>KASQDVGTAVA</u>WYQQKPGKAPKLLIY<u>SASYRST</u>GVPSRFSGSGSGTDFTLTISSL
QPEDFATYYC<u>QHHYSAPWT</u>FGGGTKVEIKRTVAAPSVFIFPPSDEQLKSGTASVVCLLNNFYPREAKVQWKVDNALQ
SGNSQESVTEQDSKDSTYSLSSTLTLSCADYEKHKVYACEVTHQGLSSPVTKSFNRGEC

SEQ ID NO: 32 hu08 KC 1.0 kK188C
DIQMTQSPSSLSASVGDRVTITC<u>KASQDVGTAVA</u>WYQQKPGKAPKLLIY<u>SASYRST</u>GVPSRFSGSGSGTDFTLTISSL
QPEDFATYYC<u>QHHYSAPWT</u>FGGGTKVEIKRTVAAPSVFIFPPSDEQLKSGTASVVCLLNNFYPREAKVQWKVDNALQ
SGNSQESVTEQDSKDSTYSLSSTLTLSKADYECHKVYACEVTHQGLSSPVTKSFNRGEC

SEQ ID NO: 33 hu08 HC 1.0 L443C/K392C
EVQLVESGGGLVQPGGSLRLSCAASGFTF<u>SRNGMS</u>WVRQAPGKGLEWVA<u>TVSSGGSYIYYADSVK</u>GRFTISRDNAK
NSLYLQMNSLRAEDTAVYYCAR<u>QGTTALATRFFDV</u>WGQGTLVTVSSASTKGPSVFPLAPSSKSTSGGTAALGCLVKD
YFPEPVTVSWNSGALTSGVHTFPAVLQSSGLYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSREEMTKNQVSLTCLVKGFYPSDIAVE
WESNGQPENNYCTTPPVLDSDGSFFLYSKLTVDKSRWQQGNVFSCSVMHEALHNHYTQKSLSCSPGK

SEQ ID NO: 34 hu08 HC 1.0 L443C/V422C
EVQLVESGGGLVQPGGSLRLSCAASGFTF<u>SRNGMS</u>WVRQAPGKGLEWVA<u>TVSSGGSYIYYADSVK</u>GRFTISRDNAK
NSLYLQMNSLRAEDTAVYYCAR<u>QGTTALATRFFDV</u>WGQGTLVTVSSASTKGPSVFPLAPSSKSTSGGTAALGCLVKD
YFPEPVTVSWNSGALTSGVHTFPAVLQSSGLYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNCFSCSVMHEALHNHYTQKSLSCSPGK

FIG. 4E

SEQ ID NO: 35 hu07-HC-v1.5
EVQLVESGGGLVQPGGSLRLSCAASGFSLTKYGVHWVRQAPGKGLEWVGVKWAGGSTDYNSALMSRFTISKDNAK
NSLYLQMNSLRAEDTAVYYCARDHRDAMDYWGQGTLVTVSASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APELLGGPSVFLFPPKPKDTLMISRTPEVTCVVVDVSHEDPEVKFNWYVDGVEVHNAKTKPREEQYNSTYRVVSVLT
VLHQDWLNGKEYKCKVSNKALPAPIEKTISKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEALHNHYTQKSLSLSPGK

SEQ ID NO: 36 hu07-LC-v1.7
DIQMTQSPSSLSASVGDRVTITCTASLSVSSTYLHWYQQKPGSSPKLWIYSTSNLASGVPSRFSGSGSGTSYTLTISS
LQPEDFATYYCHQYHRSPLTFGGGTKVEIKRTVAAPSVFIFPPSDEQLKSGTASVVCLLNNFYPREAKVQWKVDNAL
QSGNSQESVTEQDSKDSTYSLSSTLTLSKAAYEKHKVYACEVTHQGLSSPVTKSFNRGEC

SEQ ID NO: 37 hu07 VH 1.1
EVQLVESGGGLVQPGGSLRLSCAASGFSLTKYGVHWVRQAPGKGLEWVGVKWAGGSTDYNSALMSRLTISRDNAK
SSLYLQMNSLRAEDTAVYYCARDHRDAMDYWGQGTLVTVSS

SEQ ID NO: 38 hu07 VH 1.2
EVQLVESGGGLVQPGGSLRLSCAASGFTFTKYGVHWVRQAPGKGLEWVAVKWAGGSTDYNSALMSRFTISKDNAK
NSLYLQMNSLRAEDTAVYYCARDHRDAMDYWGQGTLVTVSS

SEQ ID NO: 39 hu07 VH 1.3
EVQLVESGGGLVQPGGSLRLSCAASGFSLTKYGVHWVRQAPGKGLEWVAVKWAGGSTDYNSALMSRFTISKDNAK
NSLYLQMNSLRAEDTAVYYCARDHRDAMDYWGQGTLVTVSS

SEQ ID NO: 40 hu07 VH 1.4
EVQLVESGGGLVQPGGSLRLSCAASGFSLTKYGVHWVRQAPGKGLEWVAVKWAGGSTDYNSALMSRFTISRDNAK
NSLYLQMNSLRAEDTAVYYCARDHRDAMDYWGQGTLVTVSS

SEQ ID NO: 41 hu07 VH 1.5
EVQLVESGGGLVQPGGSLRLSCAASGFSLTKYGVHWVRQAPGKGLEWVGVKWAGGSTDYNSALMSRFTISKDNAK
NSLYLQMNSLRAEDTAVYYCARDHRDAMDYWGQGTLVTVSS

FIG. 4F

SEQ ID NO: 42 hu07 VL 1.1
DIQMTQSPSSLSASVGDRVTITC<u>TASLSVSSTYLH</u>WYQQKPGSSPKLLIY<u>STSNLAS</u>GVPSRFSGSGSGTSFTLTISSL
QPEDFATYYC<u>HQYHRSPLT</u>FGGGTKVEIK

SEQ ID NO: 43 hu07 VL 1.2
DIQMTQSPSSLSASVGDRVTITC<u>TASLSVSSTYLH</u>WYQQKPGKAPKLWIY<u>STSNLAS</u>GVPSRFSGSGSGTDFTLTISS
LQPEDFATYYC<u>HQYHRSPLT</u>FGGGTKVEIK

SEQ ID NO: 44 hu07 VL 1.3
DIQMTQSPSSLSASVGDRVTITC<u>TASLSVSSTYLH</u>WYQQKPGKAPKLLIY<u>STSNLAS</u>GVPSRFSGSGSGTDYTLTISSL
QPEDFATYYC<u>HQYHRSPLT</u>FGGGTKVEIK

SEQ ID NO: 45 hu07 VL 1.4
DIQMTQSPSSLSASVGDRVTITC<u>TASLSVSSTYLH</u>WYQQKPGKAPKLWIY<u>STSNLAS</u>GVPSRFSGSGSGTDYTLTISS
LQPEDFATYYC<u>HQYHRSPLT</u>FGGGTKVEIK

SEQ ID NO: 46 hu07 VL 1.5
DIQMTQSPSSLSASVGDRVTITC<u>TASLSVSSTYLH</u>WYQQKPGSSPKLWIY<u>STSNLAS</u>GVPSRFSGSGSGTSFTLTISSL
QPEDFATYYC<u>HQYHRSPLT</u>FGGGTKVEIK

SEQ ID NO: 47 hu07 VL 1.6
DIQMTQSPSSLSASVGDRVTITC<u>TASLSVSSTYLH</u>WYQQKPGSSPKLLIY<u>STSNLAS</u>GVPSRFSGSGSGTSYTLTISSL
QPEDFATYYC<u>HQYHRSPLT</u>FGGGTKVEIK

SEQ ID NO: 48 hu07 VL 1.7
DIQMTQSPSSLSASVGDRVTITC<u>TASLSVSSTYLH</u>WYQQKPGSSPKLWIY<u>STSNLAS</u>GVPSRFSGSGSGTSYTLTISS
LQPEDFATYYC<u>HQYHRSPLT</u>FGGGTKVEIK

SEQ ID NO:49 hu08 heavy chain constant region
ASTKGPSVFPLAPSSKSTSGGTAALGCLVKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKCKVSNKALPAPIEKTISKAKGQPREPQVY
TLPPSREEMTKNQVSLTCLVKGFYPSDIAVEWESNGQPENNYKTTPPVLDSDGSFFLYSKLTVDKSRWQQGNVFSC
SVMHEALHNHYTQKSLSLSPGK

FIG. 4G

SEQ ID NO: 50 hu08-HC v1.0

EVQLVESGGGLVQPGGSLRLSCAASGFTF<u>SRNGMS</u>WVRQAPGKGLEWVA<u>TVSSGGSYIYYADSVKG</u>RFTISRDNAK
NSLYLQMNSLRAEDTAVYYCAR<u>QGTTALATRFFDV</u>WGQGTLVTVSSASTKGPSVFPLAPSSKSTSGGTAALGCLVKD
YFPEPVTVSWNSGALTSGVHTFPAVLQSSGLYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLSPGK

SEQ ID NO: 51 hu08 LC v1.0

DIQMTQSPSSLSASVGDRVTITC<u>KASQDVGTAVA</u>WYQQKPGKAPKLLIY<u>SASYRST</u>GVPSRFSGSGSGTDFTLTISSL
QPEDFATYYC<u>QHHYSAPWT</u>FGGGTKVEIKRTVAAPSVFIFPPSDEQLKSGTASVVCLLNNFYPREAKVQWKVDNALQ
SGNSQESVTEQDSKDSTYSLSSTLTLSKA<u>A</u>YEKHKVYACEVTHQGLSSPVTKSFNRGEC

SEQ ID NO: 52 hu08 LC constant region Km(3) D77A mutant

TVAAPSVFIFPPSDEQLKSGTASVVCLLNNFYPREAKVQWKVDNALQSGNSQESVTEQDSKDSTYSLSSTLTLSKAAY
EKHKVYACEVTHQGLSSPVTKSFNRGEC

SEQ ID NO: 53 hu08 LC constant region 45, 77, 83 genus

TVAAPSVFIFPPSDEQLKSGTASVVCLLNNFYPREAKVQWKVDNxLQSGNSQESVTEQDSKDSTYSLSSTLTLSKAxY
EKHKxYACEVTHQGLSSPVTKSFNRGEC

Wherein x at position 45 is A or V, x at position 77 is selected from the group consisting of A, G, I, V, L, R, S, T, Q, P, N, M, H and W, and x at position 83 is L or V.

SEQ ID NO: 54 hu08 LC constant region Km(3) D77 genus mutation

TVAAPSVFIFPPSDEQLKSGTASVVCLLNNFYPREAKVQWKVDNALQSGNSQESVTEQDSKDSTYSLSSTLTLSKAxY
EKHKVYACEVTHQGLSSPVTKSFNRGEC

Wherein x at position 77 is selected from the group consisting of A, G, I, V, L, R, S, T, Q, P, N, M, H and W.

SEQ ID NO: 55 hu08 LC constant region Km(3) Wild Type

TVAAPSVFIFPPSDEQLKSGTASVVCLLNNFYPREAKVQWKVDNALQSGNSQESVTEQDSKDSTYSLSSTLTLSKA<u>D</u>
YEKHKVYACEVTHQGLSSPVTKSFNRGEC

```
                      SEQUENCE LISTING

<160> NUMBER OF SEQ ID NOS: 55

<210> SEQ ID NO 1
<211> LENGTH: 122
<212> TYPE: PRT
<213> ORGANISM: Artificial Sequence
<220> FEATURE:
<223> OTHER INFORMATION: Synthetic Peptide Sequence
```

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Gly Met Ser Trp Val Arg Gln Ala Pro Gly Lys Gly Leu Glu Trp Val
        35                  40                  45

Ala Thr Val Ser Ser Gly Gly Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Thr Thr Ala Leu Ala Thr Arg Phe Phe Asp Val Trp
            100                 105                 110

Gly Gln Gly Thr Leu Val Thr Val Ser Ser
        115                 120

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 2

Ser Arg Asn Gly Met Ser
1               5

<210> SEQ ID NO 3
<211> LENGTH: 17
<212> TYPE: PRT
<213> ORGANISM: Artificial Sequence
<220> FEATURE:
<223> OTHER INFORMATION: Synthetic peptide sequence

<400> SEQUENCE: 3

Thr Val Ser Ser Gly Gly Ser Tyr Ile Tyr Tyr Ala Asp Ser Val Lys
1               5                   10                  15

Gly

<210> SEQ ID NO 4
<211> LENGTH: 13
<212> TYPE: PRT
<213> ORGANISM: Artificial Sequence
<220> FEATURE:
<223> OTHER INFORMATION: Synthetic peptide sequence

<400> SEQUENCE: 4

Gln Gly Thr Thr Ala Leu Ala Thr Arg Phe Phe Asp Val
1               5                   10

<210> SEQ ID NO 5
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 5

Asp Ile Gln Met Thr Gln Ser Pro Ser Ser Leu Ser Ala Ser Val Gly
1               5                   10                  15

```
Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Ser Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Ser Ala Pro Trp
                85                  90                  95

Thr Phe Gly Gly Gly Thr Lys Val Glu Ile Lys
            100                 105
```

<210> SEQ ID NO 6
<211> LENGTH: 11
<212> TYPE: PRT
<213> ORGANISM: Artificial Sequence
<220> FEATURE:
<223> OTHER INFORMATION: Synthetic peptide sequence

<400> SEQUENCE: 6

```
Lys Ala Ser Gln Asp Val Gly Thr Ala Val Ala
1               5                   10
```

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 7

```
Ser Ala Ser Tyr Arg Ser Thr
1               5
```

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 8

```
Gln His His Tyr Ser Ala Pro Trp Thr
1               5
```

<210> SEQ ID NO 9
<211> LENGTH: 116
<212> TYPE: PRT
<213> ORGANISM: Artificial Sequence
<220> FEATURE:
<223> OTHER INFORMATION: Synthetic peptide sequence

<400> SEQUENCE: 9

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Lys Tyr
            20                  25                  30

Gly Val His Trp Val Arg Gln Ala Pro Gly Lys Gly Leu Glu Trp Val
        35                  40                  45

Ala Val Lys Trp Ala Gly Gly Ser Thr Asp Tyr Asn Ser Ala Leu Met
    50                  55                  60
```

```
Ser Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Tyr Cys Ala
             85                  90                  95

Arg Asp His Arg Asp Ala Met Asp Tyr Trp Gly Gln Gly Thr Leu Val
        100                 105                 110

Thr Val Ser Ser
        115

<210> SEQ ID NO 10
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 10

Thr Lys Tyr Gly Val His
1               5

<210> SEQ ID NO 11
<211> LENGTH: 16
<212> TYPE: PRT
<213> ORGANISM: Artificial Sequence
<220> FEATURE:
<223> OTHER INFORMATION: Synthetic peptide sequence

<400> SEQUENCE: 11

Val Lys Trp Ala Gly Gly Ser Thr Asp Tyr Asn Ser Ala Leu Met Ser
1               5                   10                  15

<210> SEQ ID NO 12
<211> LENGTH: 8
<212> TYPE: PRT
<213> ORGANISM: Artificial Sequence
<220> FEATURE:
<223> OTHER INFORMATION: Synthetic peptide sequence

<400> SEQUENCE: 12

Asp His Arg Asp Ala Met Asp Tyr
1               5

<210> SEQ ID NO 13
<211> LENGTH: 108
<212> TYPE: PRT
<213> ORGANISM: Artificial Sequence
<220> FEATURE:
<223> OTHER INFORMATION: Synthetic peptide sequence

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Thr Ala Ser Leu Ser Val Ser Ser Thr
            20                  25                  30

Tyr Leu His Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys His Gln Tyr His Arg Ser Pro
             85                  90                  95
```

Leu Thr Phe Gly Gly Gly Thr Lys Val Glu Ile Lys
            100                 105

<210> SEQ ID NO 14
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 14

Thr Ala Ser Leu Ser Val Ser Ser Thr Tyr Leu His
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 15

Ser Thr Ser Asn Leu Ala Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 16

His Gln Tyr His Arg Ser Pro Leu Thr
1               5

<210> SEQ ID NO 17
<211> LENGTH: 366
<212> TYPE: DNA
<213> ORGANISM: Artificial Sequence
<220> FEATURE:
<223> OTHER INFORMATION: Synthetic nucleotide sequence

<400> SEQUENCE: 17
gaggtgcagc tggtggagtc tggcggcgga ctggtgcagc ctggcggctc tctgagactg      60
tcttgtgccg cctccggctt caccttcagt aggaatggca tgtcttgggt gaggcaggcc     120
cctggcaagg gcctggagtg gtggccacc gttagtagtg gtggtagtta catctactat     180
gcagacagtg tgaaggggcg gttcaccatc tccaggaca cgccaagaa ctccctgtac      240 ctccagatga actccctgag ggccgaggat accgccgtgt actactgtgc cagacaaggg     300
actacggcac tagctacgag gttcttcgat gtctggggcc agggcaccct ggtgaccgtg     360
tcctct                                                                366

<210> SEQ ID NO 18
<211> LENGTH: 321
<212> TYPE: DNA
<213> ORGANISM: Artificial Sequence
<220> FEATURE:
<223> OTHER INFORMATION: Synthetic nucleotide sequence

<400> SEQUENCE: 18
gacatccaga tgacccagtc cccctcttct ctgtctgcct ctgtgggcga cagagtgacc      60

```
atcacctgta aggccagtca ggatgtaggt actgctgtag cctggtatca gcagaagcct    120
ggcaaggctc ccaagctgct gatctactcg gcatcctacc ggtccactgg cgtgccttcc    180
agattctccg gctctggctc tggcaccgat tcaccctga ccatctcctc cctccagcct     240
gaggatttcg ccacctacta ctgccagcac cattatagtg ctccgtggac gtttggcggc    300
ggaacaaagg tggagatcaa g                                              321
```

<210> SEQ ID NO 19
<211> LENGTH: 122
<212> TYPE: PRT
<213> ORGANISM: Artificial Sequence
<220> FEATURE:
<223> OTHER INFORMATION: Synthetic peptide sequence

<400> SEQUENCE: 19

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Gly Met Ser Trp Val Arg Gln Thr Pro Asp Lys Arg Leu Glu Trp Val
        35                  40                  45

Ala Thr Val Ser Ser Gly Gly Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Val Tyr Tyr Cys
                85                  90                  95

Ala Arg Gln Gly Thr Thr Ala Leu Ala Thr Arg Phe Phe Asp Val Trp
            100                 105                 110

Gly Gln Gly Thr Leu Val Thr Val Ser Ser
        115                 120
```

<210> SEQ ID NO 20
<211> LENGTH: 366
<212> TYPE: DNA
<213> ORGANISM: Artificial Sequence
<220> FEATURE:
<223> OTHER INFORMATION: Synthetic nucleotide sequence

<400> SEQUENCE: 20

```
gaggtgcagc tggtggagtc tggcggcgga ctggtgcagc ctggcggctc tctgagactg    60
tcttgtgccg cctccggctt caccttcagt aggaatggca tgtcttgggt gaggcagacc    120
cctgacaagc gcctggagtg ggtggccacc gttagtagtg gtggtagtta catctactat    180
gcagacagtg tgaaggggcg gttcaccatc tccaggaca acgccaagaa ctccctgtac     240
ctccagatga gctccctgag gccgaggat accgccgtgt actactgtgc cagacaaggg    300
actacggcac tagctacgag gttcttcgat gtctggggcc agggcaccct ggtgaccgtg    360
tcctct                                                               366
```

<210> SEQ ID NO 21
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 21

```
Asp Ile Gln Met Thr Gln Ser Pro Ser Ser Leu Ser Ala Ser Val Gly
```

```
 1               5                   10                  15
Asp Arg Val Thr Ile Thr Cys Lys Ala Ser Gln Asp Val Gly Thr Ala
                20                  25                  30

Val Ala Trp Tyr Gln Gln Ile Pro Gly Lys Ala Pro Lys Leu Leu Ile
            35                  40                  45

Tyr Ser Ala Ser Tyr Arg Ser Thr Gly Val Pro Asp Arg Phe Ser Gly
        50                  55                  60

Ser Gly Ser Gly Thr Asp Phe Ser Phe Ile Ile Ser Ser Leu Gln Pro
65                  70                  75                  80

Glu Asp Phe Ala Thr Tyr Tyr Cys Gln His His Tyr Ser Ala Pro Trp
                85                  90                  95

Thr Phe Gly Gly Gly Thr Lys Val Glu Ile Lys
                100                 105
```

<210> SEQ ID NO 22
<211> LENGTH: 321
<212> TYPE: DNA
<213> ORGANISM: Artificial Sequence
<220> FEATURE:
<223> OTHER INFORMATION: Synthetic nucleotide sequence

<400> SEQUENCE: 22

```
gacatccaga tgacccagtc cccctcttct ctgtctgcct ctgtgggcga cagagtgacc      60
atcacctgta aggccagtca ggatgtaggt actgctgtag cctggtatca gcagatccct     120
ggcaaggctc ccaagctgct gatctactcg gcatcctacc ggtccactgg cgtgcctgac     180
agattctccg gctctggctc tggcaccgat ttctccttta tcatctcctc cctccagcct     240
gaggatttcg ccacctacta ctgccagcac cattatagtg ctccgtggac gtttggcggc     300
ggaacaaagg tggagatcaa g                                                321
```

<210> SEQ ID NO 23
<211> LENGTH: 122
<212> TYPE: PRT
<213> ORGANISM: Mus musculus

<400> SEQUENCE: 23

```
Glu Val Gln Leu Val Glu Ser Gly Gly Asp Leu Val Arg Pro Gly Gly
1               5                   10                  15

Ser Leu Gln Leu Ser Cys Ala Ala Ser Gly Phe Thr Phe Ser Arg Asn
            20                  25                  30

Gly Met Ser Trp Val Arg Gln Thr Pro Asp Arg Arg Leu Glu Trp Val
        35                  40                  45

Ala Thr Val Ser Ser Gly Gly Ser Tyr Ile Tyr Tyr Ala Asp Ser Val
    50                  55                  60

Lys Gly Arg Phe Thr Ile Ser Arg Asp Asn Ala Arg Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Gln Gly Thr Thr Ala Leu Ala Thr Arg Phe Phe Asp Val Trp
                100                 105                 110

Gly Ala Gly Thr Thr Val Thr Val Ser Ser
                115                 120
```

<210> SEQ ID NO 24
<211> LENGTH: 107
<212> TYPE: PRT
<213> ORGANISM: Mus musculus

<400> SEQUENCE: 24

```
Asp Ile Val Met Thr Gln Ser His Lys Phe Ile Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Ile Pro Gly Gln Ser Pro Lys Leu Leu Ile
        35                  40                  45

Tyr Ser Ala Ser Tyr Arg Ser Thr Gly Ile Pro Asp Arg Phe Thr Gly
    50                  55                  60

Ser Gly Ser Gly Thr Asp Phe Ser Phe Ile Ile Ser Val Gln Ala
65                  70                  75                  80

Glu Asp Leu Ala Leu Tyr Tyr Cys Gln His His Tyr Ser Ala Pro Trp
                85                  90                  95

Thr Phe Gly Gly Gly Thr Thr Leu Asp Ile Lys
            100                 105
```

<210> SEQ ID NO 25
<211> LENGTH: 116
<212> TYPE: PRT
<213> ORGANISM: Mus musculus

<400> SEQUENCE: 25

```
Gln Val Gln Leu Lys Glu Ser Gly Pro Gly Leu Val Ala Pro Ser Gln
1               5                   10                  15

Ser Leu Ser Ile Asn Cys Thr Val Ser Gly Phe Ser Leu Thr Lys Tyr
            20                  25                  30

Gly Val His Trp Ile Arg Gln Ser Pro Gly Lys Gly Leu Glu Trp Leu
        35                  40                  45

Gly Val Lys Trp Ala Gly Gly Ser Thr Asp Tyr Asn Ser Ala Leu Met
    50                  55                  60

Ser Arg Leu Thr Ile Ser Lys Asp Asn Asn Lys Ser Gln Val Phe Leu
65                  70                  75                  80

Lys Met Asn Ser Leu Gln Ser Asp Asp Ser Ala Met Tyr Tyr Cys Ala
                85                  90                  95

Arg Asp His Arg Asp Ala Met Asp Tyr Trp Gly Gln Gly Thr Ser Val
            100                 105                 110

Thr Val Ser Ser
        115
```

<210> SEQ ID NO 26
<211> LENGTH: 108
<212> TYPE: PRT
<213> ORGANISM: Mus musculus

<400> SEQUENCE: 26

```
Gln Val Val Leu Thr Gln Ser Pro Ala Ile Met Ser Ala Ser Pro Gly
1               5                   10                  15

Glu Arg Val Thr Met Thr Cys Thr Ala Ser Leu Ser Val Ser Ser Thr
            20                  25                  30

Tyr Leu His Trp Tyr His Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80
```

```
Ala Glu Asp Ala Ala Thr Tyr Tyr Cys His Gln Tyr His Arg Ser Pro
                85                  90                  95

Leu Thr Phe Gly Ser Gly Thr Lys Leu Glu Leu Lys
            100                 105

<210> SEQ ID NO 27
<211> LENGTH: 337
<212> TYPE: PRT
<213> ORGANISM: Macaca fascicularis

<400> SEQUENCE: 27

Asp Thr Glu Ile Lys Val Asn Pro Pro Gln Asp Phe Glu Ile Val Asp
1               5                   10                  15

Pro Gly Tyr Leu Gly Tyr Leu Tyr Leu Gln Trp Gln Pro Pro Leu Ser
            20                  25                  30

Leu Asp Asn Phe Lys Glu Cys Thr Val Glu Tyr Glu Leu Lys Tyr Arg
        35                  40                  45

Asn Ile Gly Ser Glu Thr Trp Thr Thr Ile Ile Thr Lys Asn Leu His
    50                  55                  60

Tyr Lys Asp Gly Phe Asp Leu Asn Lys Gly Ile Glu Ala Lys Ile His
65                  70                  75                  80

Thr Leu Leu Pro Trp Gln Cys Thr Asn Gly Ser Glu Val Gln Ser Ser
                85                  90                  95

Trp Ala Glu Ala Thr Tyr Trp Ile Ser Pro Gln Gly Ile Pro Glu Thr
            100                 105                 110

Lys Val Gln Asp Met Asp Cys Val Tyr Tyr Asn Trp Gln Tyr Leu Leu
        115                 120                 125

Cys Ser Trp Lys Pro Gly Ile Gly Val Leu Leu Asp Thr Asn Tyr Asn
    130                 135                 140

Leu Phe Tyr Trp Tyr Glu Gly Leu Asp Arg Ala Leu Gln Cys Val Asp
145                 150                 155                 160

Tyr Ile Lys Val Asp Gly Gln Asn Ile Gly Cys Arg Phe Pro Tyr Leu
                165                 170                 175

Glu Ser Ser Asp Tyr Lys Asp Phe Tyr Ile Cys Val Asn Gly Ser Ser
            180                 185                 190

Glu Thr Lys Pro Ile Arg Ser Ser Tyr Phe Thr Phe Gln Leu Gln Asn
        195                 200                 205

Ile Val Lys Pro Leu Pro Pro Val Cys Leu Thr Cys Thr Gln Glu Ser
    210                 215                 220

Leu Tyr Glu Ile Lys Leu Lys Trp Ser Ile Pro Leu Gly Pro Ile Pro
225                 230                 235                 240

Ala Arg Cys Phe Val Tyr Glu Ile Glu Ile Arg Glu Asp Asp Thr Thr
                245                 250                 255

Leu Val Thr Thr Thr Val Glu Asn Glu Thr Tyr Thr Leu Lys Ile Thr
            260                 265                 270

Asn Glu Thr Arg Gln Leu Cys Phe Val Val Arg Ser Lys Val Asn Ile
        275                 280                 285

Tyr Cys Ser Asp Asp Gly Ile Trp Ser Glu Trp Ser Asp Lys Gln Cys
    290                 295                 300

Trp Glu Val Glu Glu Leu Leu Lys Thr Leu Leu Leu Phe Leu Leu Leu
305                 310                 315                 320

Pro Phe Gly Phe Ile Leu Ile Leu Val Ile Phe Val Thr Gly Leu Leu
                325                 330                 335

Leu
```

<210> SEQ ID NO 28
<211> LENGTH: 452
<212> TYPE: PRT
<213> ORGANISM: Artificial Sequence
<220> FEATURE:
<223> OTHER INFORMATION: Synthetic peptide sequence

<400> SEQUENCE: 28

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Gly Met Ser Trp Val Arg Gln Ala Pro Gly Lys Gly Leu Glu Trp Val
        35                  40                  45

Ala Thr Val Ser Ser Gly Gly Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Thr Thr Ala Leu Ala Thr Arg Phe Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365
```

```
Ser Leu Thr Cys Leu Val Lys Gly Phe Tyr Pro Ser Asp Ile Ala Val
    370             375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Cys
        435                 440                 445
Ser Pro Gly Lys
    450
```

<210> SEQ ID NO 29
<211> LENGTH: 452
<212> TYPE: PRT
<213> ORGANISM: Artificial Sequence
<220> FEATURE:
<223> OTHER INFORMATION: Synthetic peptide sequence

<400> SEQUENCE: 29

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Arg Asn
            20                  25                  30
Gly Met Ser Trp Val Arg Gln Ala Pro Gly Lys Gly Leu Glu Trp Val
        35                  40                  45
Ala Thr Val Ser Ser Gly Gly Ser Tyr Ile Tyr Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Gln Gly Thr Thr Ala Leu Ala Thr Arg Phe Phe Asp Val Trp
            100                 105                 110
Gly Gln Gly Thr Leu Val Thr Val Ser Ser Ala Ser Thr Lys Gly Pro
        115                 120                 125
Ser Val Phe Pro Leu Ala Pro Ser Ser Lys Ser Thr Ser Gly Gly Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
        195                 200                 205
His Lys Pro Ser Asn Thr Lys Val Asp Lys Lys Val Glu Pro Lys Ser
    210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
```

His Glu Asp Pro Glu Val Lys Phe Asn Trp Tyr Val Asp Gly Val Glu
                275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Cys
                340                 345                 350

Val Tyr Thr Leu Pro Pro Ser Arg Glu Glu Met Thr Lys Asn Gln Val
                355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
            435                 440                 445

Ser Pro Gly Lys
        450

<210> SEQ ID NO 30
<211> LENGTH: 214
<212> TYPE: PRT
<213> ORGANISM: Artificial Sequence
<220> FEATURE:
<223> OTHER INFORMATION: Synthetic peptide sequence

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
                20                  25                  30

Val Ala Trp Tyr Gln Gln Lys Pro Gly Lys Ala Pro Lys Leu Leu Ile
            35                  40                  45

Tyr Ser Ala Ser Tyr Arg Ser Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Ser Ala Pro Trp
                85                  90                  95

Thr Phe Gly Gly Gly Thr Lys Val Glu Ile Lys Arg Thr Val Ala Cys
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 31
<211> LENGTH: 214
<212> TYPE: PRT
<213> ORGANISM: Artificial Sequence
<220> FEATURE:
<223> OTHER INFORMATION: Synthetic peptide sequence

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Ser Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Ser Ala Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Cys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 32
<211> LENGTH: 214
<212> TYPE: PRT
<213> ORGANISM: Artificial Sequence
<220> FEATURE:
<223> OTHER INFORMATION: Synthetic peptide sequence

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Ser Thr Gly Val Pro Ser Arg Phe Ser Gly
                50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Ser Ala Pro Trp
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Cys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 33
<211> LENGTH: 452
<212> TYPE: PRT
<213> ORGANISM: Artificial Sequence
<220> FEATURE:
<223> OTHER INFORMATION: Synthetic peptide sequence

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
                20                  25                  30

Gly Met Ser Trp Val Arg Gln Ala Pro Gly Lys Gly Leu Glu Trp Val
            35                  40                  45

Ala Thr Val Ser Ser Gly Gly Ser Tyr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Thr Thr Ala Leu Ala Thr Arg Phe Phe Asp Val Trp
                100                 105                 110

Gly Gln Gly Thr Leu Val Thr Val Ser Ser Ala Ser Thr Lys Gly Pro
                115                 120                 125

Ser Val Phe Pro Leu Ala Pro Ser Ser Lys Ser Thr Ser Gly Gly Thr
                130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
        210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
        260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Glu Glu Met Thr Lys Asn Gln Val
    355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Cys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Cys
    435                 440                 445

Ser Pro Gly Lys
    450

<210> SEQ ID NO 34
<211> LENGTH: 452
<212> TYPE: PRT
<213> ORGANISM: Artificial Sequence
<220> FEATURE:
<223> OTHER INFORMATION: Synthetic peptide sequence

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Gly Met Ser Trp Val Arg Gln Ala Pro Gly Lys Gly Leu Glu Trp Val
        35                  40                  45

Ala Thr Val Ser Ser Gly Gly Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Gln Gly Thr Thr Ala Leu Ala Thr Arg Phe Phe Asp Val Trp
                100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
        210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Cys Phe Ser Cys Ser Val
            420                 425                 430

Met His Glu Ala Leu His Asn His Tyr Thr Gln Lys Ser Leu Ser Cys
        435                 440                 445

Ser Pro Gly Lys
    450

<210> SEQ ID NO 35
<211> LENGTH: 445
<212> TYPE: PRT
<213> ORGANISM: Artificial Sequence
<220> FEATURE:
<223> OTHER INFORMATION: Synthetic peptide sequence

<400> SEQUENCE: 35

-continued

Glu Val Gln Leu Val Glu Ser Gly Gly Leu Val Gln Pro Gly Gly
1               5                   10                  15

Ser Leu Arg Leu Ser Cys Ala Ala Ser Gly Phe Ser Leu Thr Lys Tyr
            20                  25                  30

Gly Val His Trp Val Arg Gln Ala Pro Gly Lys Gly Leu Glu Trp Val
            35                  40                  45

Gly Val Lys Trp Ala Gly Gly Ser Thr Asp Tyr Asn Ser Ala Leu Met
        50                  55                  60

Ser Arg Phe Thr Ile Ser Lys Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Asp His Arg Asp Ala Met Asp Tyr Trp Gly Gln Gly Thr Leu Val
            100                 105                 110

Thr Val Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

```
Gln Gly Asn Val Phe Ser Cys Ser Val Met His Glu Ala Leu His Asn
                420                 425                 430
His Tyr Thr Gln Lys Ser Leu Ser Leu Ser Pro Gly Lys
        435                 440                 445

<210> SEQ ID NO 36
<211> LENGTH: 215
<212> TYPE: PRT
<213> ORGANISM: Artificial Sequence
<220> FEATURE:
<223> OTHER INFORMATION: Synthetic peptide sequence

<400> SEQUENCE: 36

Asp Ile Gln Met Thr Gln Ser Pro Ser Ser Leu Ser Ala Ser Val Gly
1               5                   10                  15
Asp Arg Val Thr Ile Thr Cys Thr Ala Ser Leu Ser Val Ser Ser Thr
            20                  25                  30
Tyr Leu His Trp Tyr Gln Gln Lys Pro Gly Ser Ser Pro Lys Leu Trp
        35                  40                  45
Ile Tyr Ser Thr Ser Asn Leu Ala Ser Gly Val Pro Ser Arg Phe Ser
    50                  55                  60
Gly Ser Gly Ser Gly Thr Ser Tyr Thr Leu Thr Ile Ser Ser Leu Gln
65                  70                  75                  80
Pro Glu Asp Phe Ala Thr Tyr Tyr Cys His Gln Tyr His Arg Ser Pro
                85                  90                  95
Leu Thr Phe Gly Gly Gly Thr Lys Val Glu Ile Lys Arg Thr Val Ala
            100                 105                 110
Ala Pro Ser Val Phe Ile Phe Pro Pro Ser Asp Glu Gln Leu Lys Ser
        115                 120                 125
Gly Thr Ala Ser Val Val Cys Leu Leu Asn Asn Phe Tyr Pro Arg Glu
    130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Ala Tyr Glu Lys His Lys Val
            180                 185                 190
Tyr Ala Cys Glu Val Thr His Gln Gly Leu Ser Ser Pro Val Thr Lys
        195                 200                 205
Ser Phe Asn Arg Gly Glu Cys
    210                 215

<210> SEQ ID NO 37
<211> LENGTH: 116
<212> TYPE: PRT
<213> ORGANISM: Artificial Sequence
<220> FEATURE:
<223> OTHER INFORMATION: Synthetic peptide sequence

<400> SEQUENCE: 37

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Ser Leu Thr Lys Tyr
            20                  25                  30
Gly Val His Trp Val Arg Gln Ala Pro Gly Lys Gly Leu Glu Trp Val
        35                  40                  45
Gly Val Lys Trp Ala Gly Gly Ser Thr Asp Tyr Asn Ser Ala Leu Met
    50                  55                  60
```

```
Ser Arg Leu Thr Ile Ser Arg Asp Asn Ala Lys Ser Ser Leu Tyr Leu
 65                  70                  75                  80

Gln Met Asn Ser Leu Arg Ala Glu Asp Thr Ala Val Tyr Tyr Cys Ala
             85                  90                  95

Arg Asp His Arg Asp Ala Met Asp Tyr Trp Gly Gln Gly Thr Leu Val
         100                 105                 110

Thr Val Ser Ser
        115
```

<210> SEQ ID NO 38
<211> LENGTH: 116
<212> TYPE: PRT
<213> ORGANISM: Artificial Sequence
<220> FEATURE:
<223> OTHER INFORMATION: Synthetic peptide sequence

<400> SEQUENCE: 38

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Lys Tyr
             20                  25                  30

Gly Val His Trp Val Arg Gln Ala Pro Gly Lys Gly Leu Glu Trp Val
         35                  40                  45

Ala Val Lys Trp Ala Gly Gly Ser Thr Asp Tyr Asn Ser Ala Leu Met
     50                  55                  60

Ser Arg Phe Thr Ile Ser Lys Asp Asn Ala Lys Asn Ser Leu Tyr Leu
 65                  70                  75                  80

Gln Met Asn Ser Leu Arg Ala Glu Asp Thr Ala Val Tyr Tyr Cys Ala
             85                  90                  95

Arg Asp His Arg Asp Ala Met Asp Tyr Trp Gly Gln Gly Thr Leu Val
         100                 105                 110

Thr Val Ser Ser
        115
```

<210> SEQ ID NO 39
<211> LENGTH: 116
<212> TYPE: PRT
<213> ORGANISM: Artificial Sequence
<220> FEATURE:
<223> OTHER INFORMATION: Synthetic peptide sequence

<400> SEQUENCE: 39

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Leu Thr Lys Tyr
             20                  25                  30

Gly Val His Trp Val Arg Gln Ala Pro Gly Lys Gly Leu Glu Trp Val
         35                  40                  45

Ala Val Lys Trp Ala Gly Gly Ser Thr Asp Tyr Asn Ser Ala Leu Met
     50                  55                  60

Ser Arg Phe Thr Ile Ser Lys Asp Asn Ala Lys Asn Ser Leu Tyr Leu
 65                  70                  75                  80

Gln Met Asn Ser Leu Arg Ala Glu Asp Thr Ala Val Tyr Tyr Cys Ala
             85                  90                  95

Arg Asp His Arg Asp Ala Met Asp Tyr Trp Gly Gln Gly Thr Leu Val
         100                 105                 110

Thr Val Ser Ser
```

<210> SEQ ID NO 40
<211> LENGTH: 116
<212> TYPE: PRT
<213> ORGANISM: Artificial Sequence
<220> FEATURE:
<223> OTHER INFORMATION: Synthetic peptide sequence

<400> SEQUENCE: 40

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Lys Tyr
            20                  25                  30

Gly Val His Trp Val Arg Gln Ala Pro Gly Lys Gly Leu Glu Trp Val
        35                  40                  45

Ala Val Lys Trp Ala Gly Gly Ser Thr Asp Tyr Asn Ser Ala Leu Met
    50                  55                  60

Ser Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Asp His Arg Asp Ala Met Asp Tyr Trp Gly Gln Gly Thr Leu Val
            100                 105                 110

Thr Val Ser Ser
        115
```

<210> SEQ ID NO 41
<211> LENGTH: 116
<212> TYPE: PRT
<213> ORGANISM: Artificial Sequence
<220> FEATURE:
<223> OTHER INFORMATION: Synthetic peptide sequence

<400> SEQUENCE: 41

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Lys Tyr
            20                  25                  30

Gly Val His Trp Val Arg Gln Ala Pro Gly Lys Gly Leu Glu Trp Val
        35                  40                  45

Gly Val Lys Trp Ala Gly Gly Ser Thr Asp Tyr Asn Ser Ala Leu Met
    50                  55                  60

Ser Arg Phe Thr Ile Ser Lys Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Asp His Arg Asp Ala Met Asp Tyr Trp Gly Gln Gly Thr Leu Val
            100                 105                 110

Thr Val Ser Ser
        115
```

<210> SEQ ID NO 42
<211> LENGTH: 108
<212> TYPE: PRT
<213> ORGANISM: Artificial Sequence
<220> FEATURE:
<223> OTHER INFORMATION: Synthetic peptide sequence

<400> SEQUENCE: 42

```
Asp Ile Gln Met Thr Gln Ser Pro Ser Ser Leu Ser Ala Ser Val Gly
1               5                   10                  15

Asp Arg Val Thr Ile Thr Cys Thr Ala Ser Leu Ser Val Ser Ser Thr
            20                  25                  30

Tyr Leu His Trp Tyr Gln Gln Lys Pro Gly Ser Ser Pro Lys Leu Leu
        35                  40                  45

Ile Tyr Ser Thr Ser Asn Leu Ala Ser Gly Val Pro Ser Arg Phe Ser
    50                  55                  60

Gly Ser Gly Ser Gly Thr Ser Phe Thr Leu Thr Ile Ser Ser Leu Gln
65                  70                  75                  80

Pro Glu Asp Phe Ala Thr Tyr Tyr Cys His Gln Tyr His Arg Ser Pro
                85                  90                  95

Leu Thr Phe Gly Gly Gly Thr Lys Val Glu Ile Lys
            100                 105
```

<210> SEQ ID NO 43
<211> LENGTH: 108
<212> TYPE: PRT
<213> ORGANISM: Artificial Sequence
<220> FEATURE:
<223> OTHER INFORMATION: Synthetic peptide sequence

<400> SEQUENCE: 43

```
Asp Ile Gln Met Thr Gln Ser Pro Ser Ser Leu Ser Ala Ser Val Gly
1               5                   10                  15

Asp Arg Val Thr Ile Thr Cys Thr Ala Ser Leu Ser Val Ser Ser Thr
            20                  25                  30

Tyr Leu His Trp Tyr Gln Gln Lys Pro Gly Lys Ala Pro Lys Leu Trp
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys His Gln Tyr His Arg Ser Pro
                85                  90                  95

Leu Thr Phe Gly Gly Gly Thr Lys Val Glu Ile Lys
            100                 105
```

<210> SEQ ID NO 44
<211> LENGTH: 108
<212> TYPE: PRT
<213> ORGANISM: Artificial Sequence
<220> FEATURE:
<223> OTHER INFORMATION: Synthetic peptide sequence

<400> SEQUENCE: 44

```
Asp Ile Gln Met Thr Gln Ser Pro Ser Ser Leu Ser Ala Ser Val Gly
1               5                   10                  15

Asp Arg Val Thr Ile Thr Cys Thr Ala Ser Leu Ser Val Ser Ser Thr
            20                  25                  30

Tyr Leu His Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys His Gln Tyr His Arg Ser Pro
```

```
                       85                  90                  95

Leu Thr Phe Gly Gly Gly Thr Lys Val Glu Ile Lys
                100                 105

<210> SEQ ID NO 45
<211> LENGTH: 108
<212> TYPE: PRT
<213> ORGANISM: Artificial Sequence
<220> FEATURE:
<223> OTHER INFORMATION: Synthetic peptide sequence

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Thr Ala Ser Leu Ser Val Ser Ser Thr
                20                  25                  30

Tyr Leu His Trp Tyr Gln Gln Lys Pro Gly Lys Ala Pro Lys Leu Trp
            35                  40                  45

Ile Tyr Ser Thr Ser Asn Leu Ala Ser Gly Val Pro Ser Arg Phe Ser
        50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys His Gln Tyr His Arg Ser Pro
                85                  90                  95

Leu Thr Phe Gly Gly Gly Thr Lys Val Glu Ile Lys
                100                 105

<210> SEQ ID NO 46
<211> LENGTH: 108
<212> TYPE: PRT
<213> ORGANISM: Artificial Sequence
<220> FEATURE:
<223> OTHER INFORMATION: Synthetic peptide sequence

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Thr Ala Ser Leu Ser Val Ser Ser Thr
                20                  25                  30

Tyr Leu His Trp Tyr Gln Gln Lys Pro Gly Ser Ser Pro Lys Leu Trp
            35                  40                  45

Ile Tyr Ser Thr Ser Asn Leu Ala Ser Gly Val Pro Ser Arg Phe Ser
        50                  55                  60

Gly Ser Gly Ser Gly Thr Ser Phe Thr Leu Thr Ile Ser Ser Leu Gln
65                  70                  75                  80

Pro Glu Asp Phe Ala Thr Tyr Tyr Cys His Gln Tyr His Arg Ser Pro
                85                  90                  95

Leu Thr Phe Gly Gly Gly Thr Lys Val Glu Ile Lys
                100                 105

<210> SEQ ID NO 47
<211> LENGTH: 108
<212> TYPE: PRT
<213> ORGANISM: Artificial Sequence
<220> FEATURE:
<223> OTHER INFORMATION: Synthetic peptide sequence

<400> SEQUENCE: 47

Asp Ile Gln Met Thr Gln Ser Pro Ser Ser Leu Ser Ala Ser Val Gly
1               5                   10                  15
```

Asp Arg Val Thr Ile Thr Cys Thr Ala Ser Leu Ser Val Ser Ser Thr
            20                  25                  30

Tyr Leu His Trp Tyr Gln Gln Lys Pro Gly Ser Ser Pro Lys Leu Leu
        35                  40                  45

Ile Tyr Ser Thr Ser Asn Leu Ala Ser Gly Val Pro Ser Arg Phe Ser
50                  55                  60

Gly Ser Gly Ser Gly Thr Ser Tyr Thr Leu Thr Ile Ser Ser Leu Gln
65                  70                  75                  80

Pro Glu Asp Phe Ala Thr Tyr Tyr Cys His Gln Tyr His Arg Ser Pro
            85                  90                  95

Leu Thr Phe Gly Gly Gly Thr Lys Val Glu Ile Lys
            100                 105

<210> SEQ ID NO 48
<211> LENGTH: 108
<212> TYPE: PRT
<213> ORGANISM: Artificial Sequence
<220> FEATURE:
<223> OTHER INFORMATION: Synthetic peptide sequence

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Thr Ala Ser Leu Ser Val Ser Ser Thr
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ser Arg Phe Ser
50                  55                  60

Gly Ser Gly Ser Gly Thr Ser Tyr Thr Leu Thr Ile Ser Ser Leu Gln
65                  70                  75                  80

Pro Glu Asp Phe Ala Thr Tyr Tyr Cys His Gln Tyr His Arg Ser Pro
            85                  90                  95

Leu Thr Phe Gly Gly Gly Thr Lys Val Glu Ile Lys
            100                 105

<210> SEQ ID NO 49
<211> LENGTH: 330
<212> TYPE: PRT
<213> ORGANISM: Artificial Sequence
<220> FEATURE:
<223> OTHER INFORMATION: Synthetic peptide sequence

<400> SEQUENCE: 49

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys

```
            100                 105                 110
Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 50
<211> LENGTH: 452
<212> TYPE: PRT
<213> ORGANISM: Artificial Sequence
<220> FEATURE:
<223> OTHER INFORMATION: Synthetic peptide sequence

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Gly Met Ser Trp Val Arg Gln Ala Pro Gly Lys Gly Leu Glu Trp Val
        35                  40                  45

Ala Thr Val Ser Ser Gly Gly Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Thr Thr Ala Leu Ala Thr Arg Phe Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
```

```
            130                 135                 140
Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 51
<211> LENGTH: 214
<212> TYPE: PRT
<213> ORGANISM: Artificial Sequence
<220> FEATURE:
<223> OTHER INFORMATION: Synthetic peptide sequence

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
```

```
                   35                  40                  45
Tyr Ser Ala Ser Tyr Arg Ser Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln His Tyr Ser Ala Pro Trp
                 85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Ala Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 52
<211> LENGTH: 106
<212> TYPE: PRT
<213> ORGANISM: Artificial Sequence
<220> FEATURE:
<223> OTHER INFORMATION: Mutant version of human constant kappa domain

<400> SEQUENCE: 52

Thr Val Ala Ala Pro Ser Val Phe Ile Phe Pro Pro Ser Asp Glu Gln
 1               5                  10                  15

Leu Lys Ser Gly Thr Ala Ser Val Val Cys Leu Leu Asn Asn Phe Tyr
             20                  25                  30

Pro Arg Glu Ala Lys Val Gln Trp Lys Val Asp Asn Ala Leu Gln Ser
         35                  40                  45

Gly Asn Ser Gln Glu Ser Val Thr Glu Gln Asp Ser Lys Asp Ser Thr
     50                  55                  60

Tyr Ser Leu Ser Ser Thr Leu Thr Leu Ser Lys Ala Ala Tyr Glu Lys
 65                  70                  75                  80

His Lys Val Tyr Ala Cys Glu Val Thr His Gln Gly Leu Ser Ser Pro
                 85                  90                  95

Val Thr Lys Ser Phe Asn Arg Gly Glu Cys
            100                 105

<210> SEQ ID NO 53
<211> LENGTH: 106
<212> TYPE: PRT
<213> ORGANISM: Artificial Sequence
<220> FEATURE:
<223> OTHER INFORMATION: Mutant version of human constant kappa domain
<220> FEATURE:
<221> NAME/KEY: MISC_FEATURE
<222> LOCATION: (45)..(45)
<223> OTHER INFORMATION: Xaa at position 45 is Ala or Val
<220> FEATURE:
<221> NAME/KEY: MISC_FEATURE
```

<222> LOCATION: (77)..(77)
<223> OTHER INFORMATION: Xaa at position 77 is Ala, Gly, Ile, Val, Leu,
      Arg, Ser, Thr, Gln, Pro, Asn, Met, His or Trp
<220> FEATURE:
<221> NAME/KEY: MISC_FEATURE
<222> LOCATION: (83)..(83)
<223> OTHER INFORMATION: Xaa at position 83 is Leu or Val

<400> SEQUENCE: 53

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Xaa Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Xaa Tyr Glu Lys
65                  70                  75                  80

His Lys Xaa Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 54
<211> LENGTH: 106
<212> TYPE: PRT
<213> ORGANISM: Artificial Sequence
<220> FEATURE:
<223> OTHER INFORMATION: Mutant version of human constant kappa domain
<220> FEATURE:
<221> NAME/KEY: MISC_FEATURE
<222> LOCATION: (77)..(77)
<223> OTHER INFORMATION: Xaa at position 77 is Ala, Gly, Ile, Val, Leu,
      Arg, Ser, Thr, Gln, Pro, Asn, Met, His or Trp

<400> SEQUENCE: 54

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Xaa Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 55
<211> LENGTH: 106
<212> TYPE: PRT
<213> ORGANISM: Artificial Sequence
<220> FEATURE:
<223> OTHER INFORMATION: Mutant version of human constant kappa domain

<400> SEQUENCE: 55

Thr Val Ala Ala Pro Ser Val Phe Ile Phe Pro Pro Ser Asp Glu Gln
1               5                   10                  15

-continued

```
Leu Lys Ser Gly Thr Ala Ser Val Val Cys Leu Leu Asn Asn Phe Tyr
            20              25              30

Pro Arg Glu Ala Lys Val Gln Trp Lys Val Asp Asn Ala Leu Gln Ser
        35              40              45

Gly Asn Ser Gln Glu Ser Val Thr Glu Gln Asp Ser Lys Asp Ser Thr
    50              55              60

Tyr Ser Leu Ser Ser Thr Leu Thr Leu Ser Lys Ala Asp Tyr Glu Lys
65              70              75              80

His Lys Val Tyr Ala Cys Glu Val Thr His Gln Gly Leu Ser Ser Pro
                85              90              95

Val Thr Lys Ser Phe Asn Arg Gly Glu Cys
            100             105
```

US 9,828,428 B2

ANTI-IL-13 RECEPTOR ALPHA 2 ANTIBODIES AND ANTIBODY-DRUG CONJUGATES

CROSS REFERENCE TO RELATED APPLICATIONS

This application is a national stage submission under 35 U.S.C. §371 from International Application No. PCT/IB2013/059786, filed Oct. 30, 2013 which claims the benefit of priority of U.S. Provisional Patent Application No. 61/723,545 filed Nov. 7, 2012, U.S. Provisional Patent Application No. 61/749,610 filed Jan. 7, 2013, U.S. Provisional Patent Application No. 61/886,156 filed Oct. 3, 2013 and U.S. Provisional Patent Application No. 61/889,179 filed Oct. 10, 2013, the disclosures of each of which are incorporated herein by reference in their entirety.

REFERENCE TO SEQUENCE LISTING

This application contains a sequence listing filed electronically via EFS-Web. The sequence listing is provided as a txt file entitled "PC71968PRV4SeqListing_ST25.txt" created on Oct. 10, 2013 and having a size of 72 KB. The sequence listing contained in the txt file is part of the specification and is incorporated herein by reference in its entirety.

FIELD OF THE INVENTION

This invention pertains to anti-IL-13 receptor alpha 2 (IL-13-Rα2) antibodies and antibody-drug conjugates for the treatment of cancer.

BACKGROUND OF THE INVENTION

High levels of IL-13-Rα2 have been identified in a number of tumor cells, including pancreatic, breast, ovarian and malignant gliomas. In contrast, only a few types of normal tissues express IL-13-Rα2, and only at low levels. The treatment of cancer has improved over the past decade with surgery, radiation therapy, and chemotherapy as the primary treatment options. Such treatments can extend survival and/or relieve symptoms in many patients but are not likely to produce a cure for many patients. There remains a significant need for additional therapeutic options for cancers.

Therefore, anti-IL-13-Rα2 antibody-drug conjugates that can exert a clinically useful cytotoxic effect on IL-13-Rα2 expressing tumor cells, particularly without exerting undesirable effects on non-IL-13-Rα2 expressing cells, fulfill an unmet clinical need in the treatment of various IL-13-Rα2 expressing tumor cells.

SUMMARY OF THE INVENTION

The present invention provides anti-IL-13-Rα2 antibody-drug conjugates and methods of use for the treatment of cancer.

The present invention provides an isolated antibody or antigen-binding fragment that specifically binds to human IL-13-Rα2 wherein the antibody comprises: a heavy chain variable region comprising a CDR1, CDR2, and CDR3 of the VH sequence of SEQ ID NO: 1 and, a light chain variable region comprising a CDR1, CDR2, and CDR3 of the VL sequence of SEQ ID NO: 5.

The present invention further provides an isolated antibody or antigen-binding fragment that specifically binds to human IL-13-Rα2 wherein the antibody comprises: (a) a heavy chain CDR1 comprising SEQ ID NO: 2; (b) a heavy chain CDR2 comprising SEQ ID NO: 3; (c) a heavy chain CDR3 comprising SEQ ID NO: 4; (d) a light chain CDR1 comprising SEQ ID NO: 6; (e) a light chain CDR2 comprising SEQ ID NO: 7; and, (f) a light chain CDR3 comprising SEQ ID NO: 8.

The present invention further provides an isolated antibody or antigen-binding fragment that specifically binds to human IL-13-Rα2 wherein said isolated antibody further comprises the heavy chain variable region amino acid sequence of SEQ ID NO: 1 and the light chain variable region amino acid sequence of SEQ ID NO: 5.

The present invention further provides an isolated antibody or antigen-binding fragment that specifically binds to human IL-13-Rα2 wherein said isolated antibody comprises a heavy chain comprising the amino acid sequence of SEQ ID NO: 50 and wherein said isolated antibody comprises a light chain comprising the amino acid sequence of SEQ ID NO: 51.

The present invention further provides an antibody-drug conjugate comprising a cytotoxic agent conjugated to an antibody or antigen-binding fragment thereof that specifically binds to human IL-13-Rα2, The present invention further provides an antibody-drug conjugate that specifically binds to human IL-13-Rα2 wherein said conjugate has the formula: Ab-(L-D)p, wherein; (a) Ab is the antibody or antigen-binding fragment thereof of the present invention; (b) L-D is a linker-drug moiety, wherein L is a linker, and D is a drug; and (c) p is an integer from 1 to about 8.

The present invention further provides an antibody-drug conjugate that specifically binds to human IL-13-Rα2 wherein the linker is selected from the group consisting of maleimidocaproyl (mc) and maleimidocaproyl-Val-Cit-PABA (vc).

The present invention further provides an antibody-drug conjugate that specifically binds to human IL-13-Rα2 wherein the linker-drug moiety has the formula designated vc-0101 or mc-3377 as shown in Example 14.

The present invention further provides an antibody-drug conjugate that specifically binds to human IL-13-Rα2 wherein Ab comprises: (a) a heavy chain variable region comprising a CDR1, CDR2, and CDR3 of the VH sequence of SEQ ID NO: 1; and, (b) a light chain variable region comprising a CDR1, CDR2, and CDR3 of the VL sequence of SEQ ID NO: 5.

The present invention further provides an antibody-drug conjugate that specifically binds to human IL-13-Rα2 wherein Ab comprises: (a) a heavy chain CDR1 comprising SEQ ID NO: 2; (b) a heavy chain CDR2 comprising SEQ ID NO: 3; (c) a heavy chain CDR3 comprising SEQ ID NO: 4; (d) a light chain CDR1 comprising SEQ ID NO: 6; (e) a light chain CDR2 comprising SEQ ID NO: 7; and, (f) a light chain CDR3 comprising SEQ ID NO: 8.

The present invention further provides an antibody-drug conjugate wherein L-D is selected from the group consisting of vc-0101, mc-3377, mc-0131, MalPeg-6121, Mal Peg-0131, mc-6121, vc-3906, vc-6780, mc-8261, mc3906, and MalPeg-8261.

The present invention further provides an antibody-drug conjugate that specifically binds to human IL-13-Rα2 wherein said conjugate utilizes site-specific conjugation on engineered cysteine residues and has the formula: Ab-(L-D)p, or a pharmaceutically acceptable salt thereof wherein;

(a) Ab is the antibody or antigen-binding fragment thereof comprising a heavy chain variable region comprising a CDR1, CDR2, and CDR3 of the VH sequence shown in SEQ ID NO: 1; a light chain variable region comprising a CDR1, CDR2, and CDR3 of the VL sequence shown in SEQ ID NO: 5; and an engineered Fc region comprising at least one pair of amino acid substitutions selected from the group consisting of the amino acid sequence of SEQ ID NO:33 and SEQ ID NO:34; or an engineered Fc region and at least one engineered light chain constant region selected from group consisting of L443C (SEQ ID NO: 28), Q347C (SEQ ID NO: 29), kK183C (SEQ ID NO: 31), L443C/kA111C (SEQ ID NOS: 28 and 30), L443C/kK183C (SEQ ID NOS: 28 and 31), Q347C/kA111C (SEQ ID NOS: 29 and 30), and Q347C/kK183C (SEQ ID NOS: 29 and 31); (b) L-D is a linker-drug moiety, wherein L is a linker, and D is a drug; and (c) p is an integer from 1 to about 8.

The present invention further provides the antibody-drug conjugate described above that utilizes site specific conjugation on engineered cysteine residues, wherein the linker-drug moiety has the formula designated vc-0101 or mc-3377 as shown in Example 14, or a pharmaceutically acceptable salt or solvate form thereof, and p is an integer of about 4.

The present invention further provides the antibody-drug conjugate of the present invention that utilizes the Multi-functional Antibody Conjugates (MAC) technology, wherein said antibody or antigen binding portion thereof specifically binds to human IL-13Rα2 wherein the antibody has the mutation D185A at position 185 of the LC as shown in SEQ ID NO: 52, and the antibody is covalently conjugated to at least one drug moiety through a linker attached to a side chain of K188 of the LC of SEQ ID NO:49; wherein the drug moiety has the formula designated 0101 or 3377 as shown in Example 13, or a pharmaceutically acceptable salt or solvate form thereof, and p is an integer in a range whose lower limit may be selected from the group consisting of about 1.5, about 1.6, about 1.7, about 1.8, about 1.9, and about 2.0, and whose upper limit may be selected from the group consisting of about 2.0, about 2.1, about 2.2, about 2.3, about 2.4, about 2.5. In some aspects, p is about 2.

The present invention further provides a pharmaceutical composition comprising an antibody-drug conjugate of the present invention and a pharmaceutically acceptable carrier.

The present invention further provides a method of treating an IL-13-Rα2 expressing cancer in a patient in need thereof, comprising administering to said patient an antibody-drug conjugate of the present invention.

The present invention further provides a method of treating an IL-13-Rα2 expressing cancer wherein said cancer is selected from the group consisting of carcinomas of the bladder, breast, cervix, colon, malignant gliomas, endometrium, kidney, lung, esophagus, ovary, prostate, pancreas, melanoma, stomach, and testes.

More preferably, the present invention provides a method of treating an IL-13-Rα2 expressing cancer wherein said cancer is selected from the group consisting of, lung, colon, stomach, pancreatic, ovarian, malignant gliomas, and melanoma.

The invention further provides an antibody-drug conjugate of the present invention for use in therapy.

The invention further provides use of an antibody-drug conjugate of the present invention for the manufacture of a medicament for therapy.

The invention further provides the use of an antibody-drug conjugate of the present invention, wherein said use is for the treatment of an IL-13-Rα2 expressing cancer.

The invention further provides a nucleic acid that encodes an IL-13-Rα2 antibody, a vector comprising said nucleic acid, and a host cell comprising said vector.

The invention further provides a process for producing an IL-13-Rα2 antibody wherein said process comprises culturing the host cell comprising the above mentioned vector and recovering the antibody from the cell culture.

The invention further provides a process for producing an IL-13-Rα2 antibody-drug conjugate comprising: (a) linking a linker selected from the group consisting of maleimido-caproyl and maleimidocaproyl-Val-Cit-PABA to a drug selected from the group consisting of 0101 and 3377 resulting in a linker-drug moeity; (b) conjugating said linker-drug moeity to the antibody recovered from the cell culture of indicated above; and, (c) purifying the antibody-drug conjugate.

The invention further provides an isolated antibody that competes with an antibody or antigen-binding fragment thereof of the present invention for specific binding to human IL-13-Rα2.

The invention further provides an antibody-drug conjugate comprising an antibody or antigen-binding fragment thereof of the present invention for specific binding to human IL-13-Rα2.

The invention further provides a method for predicting whether a subject with cancer will respond to an antibody-drug conjugate of the present invention comprising: determining whether a biological sample of said cancer from the subject expresses hIL-13-Rα2.

The invention further provides a process of determining the level of hIL-13-Rα2 in a biological sample comprising the steps of: testing a sample from a subject suspected to have cancer in a immunoassay using an antibody of the present invention; determining the cell surface levels of hIL-13-Rα2 on said sample; and, comparing the cell surface levels of hIL-13-Rα2 with that of a reference subject or standard.

The invention further a method of treating an IL-13-Rα2 expressing cancer said method comprising: determining the level of hIL-13-Rα2 in a biological sample comprising the steps of: testing a sample from a subject suspected to have cancer in a immunoassay using an antibody of the present invention; determining the cell surface levels of hIL-13-Rα2 on said sample; comparing the cell surface levels of hIL-13-Rα2 with that of a normal reference subject or standard; and administering an antibody-drug conjugate of the present invention.

BRIEF DESCRIPTION OF THE DRAWINGS

FIG. 4A-4G: SEQ ID NOS: 1-55.

DETAILED DESCRIPTION OF THE INVENTION

Figure 1:
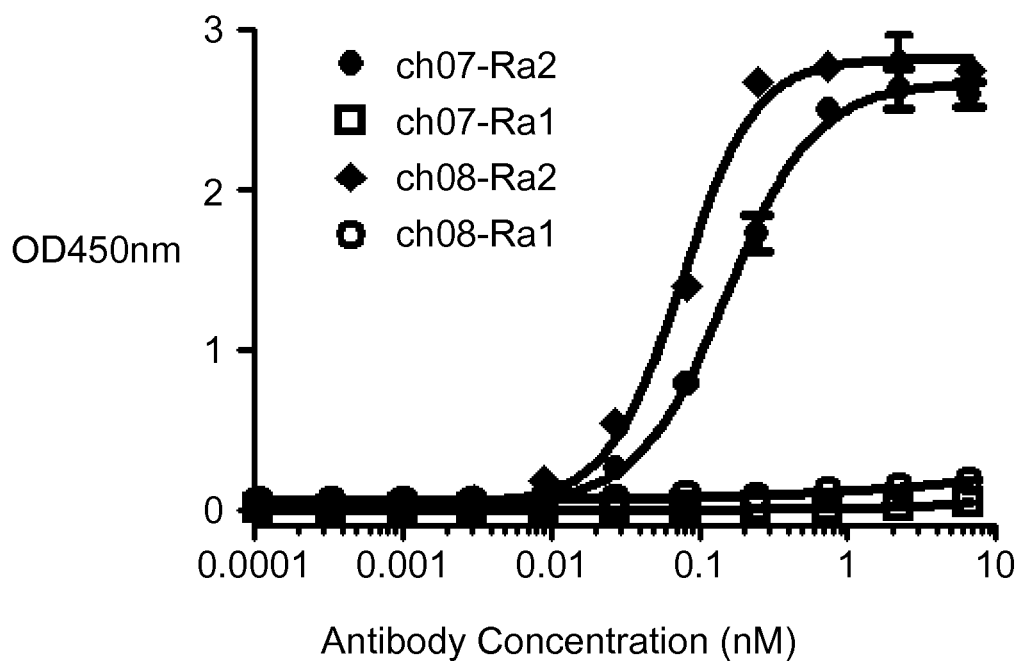
FIG. 1: Binding specificity of chimerc antibodies ch07 and ch08 to hIL-13-Rα2 but not hIL-13Rα1.

The present invention provides IL-13-Rα2 antibody-drug conjugates for the treatment of cancer. In order that the present invention is more readily understood, certain terms and general techniques are first defined.

All amino acid abbreviations used in this disclosure are those accepted by the United States Patent and Trademark Office as set forth in 37 C.F.R. §1.822(d)(1).

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well known and commonly used in the art.

The methods and techniques of the present invention are generally performed according to conventional methods well known in the art and as described in various general and more specific references that are cited and discussed throughout the present specification unless otherwise indicated. See, e.g., Sambrook J. & Russell D. *Molecular Cloning: A Laboratory Manual*, 3rd ed., Cold Spring Harbor Laboratory Press, Cold Spring Harbor, N.Y. (2000); Ausubel et al., *Short Protocols in Molecular Biology: A Compendium of Methods from Current Protocols in Molecular Biology*, Wiley, John & Sons, Inc. (2002); Harlow and Lane *Using Antibodies: A Laboratory Manual*, Cold Spring Harbor Laboratory Press, Cold Spring Harbor, N.Y. (1998); and Coligan et al., *Short Protocols in Protein Science*, Wiley, John & Sons, Inc. (2003).

An "antibody" or "Ab" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact polyclonal or monoclonal antibodies, but also any antigen binding fragment (i.e., "antigen-binding portion") or single chain thereof, fusion proteins comprising an antibody, and any other modified configuration of the immunoglobulin molecule that comprises an antigen recognition site including, for example without limitation, scFv, single domain antibodies (e.g., shark and camelid antibodies), maxibodies, minibodies, intrabodies, diabodies, triabodies, tetrabodies, v-NAR and bis-scFv (see, e.g., Hollinger and Hudson, 2005, Nature Biotechnology 23(9): 1126-1136). An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

The term "isolated" refers to a molecule that is substantially free of its natural environment. For instance, an isolated antibody is substantially free of cellular material or other proteins from the cell or tissue source from which it was derived.

The term "antigen-binding fragment" of an antibody, as used herein, refers to one or more fragments of an intact antibody that retain the ability to specifically bind to a given antigen (e.g., target IL-13-Rα2). Antigen binding functions of an antibody can be performed by fragments of an intact antibody. Examples of binding fragments encompassed within the term "antigen binding portion" of an antibody include Fab; Fab'; F(ab')$_2$; an Fd fragment consisting of the VH and CH1 domains; an Fv fragment consisting of the VL and VH domains of a single arm of an antibody; a single domain antibody (dAb) fragment (Ward et al., 1989 Nature 341:544-546), and an isolated complementarity determining region (CDR).

A "variable region" of an antibody refers to the variable region of the antibody light chain (VL) or the variable region of the antibody heavy chain (VH), either alone or in combination. As known in the art, the variable regions of the heavy and light chain each consist of four framework regions (FRs) connected by three complementarity determining regions (CDR1, CDR2, and CDR3) also known as hypervariable regions, contribute to the formation of the antigen binding site of antibodies. If variants of a subject variable region are desired, particularly with substitution in amino acid residues outside of a CDR region (i.e., in the framework region), appropriate amino acid substitution, preferably, conservative amino acid substitution, can be identified by comparing the subject variable region to the variable regions of other antibodies which contain CDR1 and CDR2 sequences in the same canoninical class as the subject variable region (Chothia and Lesk, J Mol Biol 196(4): 901-917, 1987). When choosing FR to flank subject CDRs, e.g., when humanizing or optimizing an antibody, FRs from antibodies which contain CDR1 and CDR2 sequences in the same canonical class are preferred.

A "CDR" of a variable domain are amino acid residues within the variable region that are identified in accordance with the definitions of the Kabat, Chothia, the acccumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., 1989, Nature 342:877-883. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., 1996, J. Mol. Biol., 262:732-745. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

The terms "IgG Fc region", "Fc region", "Fc domain" and "Fc", as interchangeably used herein refer to the portion of an IgG molecule that correlates to a crystallizable fragment obtained by papain digestion of an IgG molecule. The Fc region consists of the C-terminal half of the two heavy chains of an IgG molecule that are linked by disulfide bonds. It has no antigen binding activity but contains the carbohydrate moiety and the binding sites for complement and Fc receptors, including the FcRn receptor (see below). The Fc fragment contains the entire second constant domain CH2 (residues 231-340 of human IgG1, according to the Kabat numbering system) and the third constant domain CH3 (residues 341-447).

By "engineered Fc polypeptide", "engineered Fc region" and "engineered Fc" as the terms are interchangeably used herein, is meant an Fc polypeptide, or portion thereof, comprising at least one mutation, e.g., an amino acid substitution, introducing a site for conjugation. Preferably, the mutation introduces a cysteine in place of the naturally-occurring amino acid residue at that position, where the mutation creates a reactive site (e.g., a reactive sulfhydryl group) for conjugation of a moiety to the Fc.

The term "monoclonal antibody" or "mAb" refers to an antibody that is derived from a single copy or clone, including e.g., any eukaryotic, prokaryotic, or phage clone, and not the method by which it is produced. Preferably, a monoclonal antibody of the invention exists in a homogeneous or substantially homogeneous population.

"Humanized" antibody refers to forms of non-human (e.g. murine) antibodies that are chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. Preferably, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity.

"Human antibody" or "Fully Human antibody" refers to those antibodies derived from transgenic mice carrying human antibody genes or from human cells.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

A "therapeutic agent" is an agent that exerts a cytotoxic, cytostatic, and/or immunomodulatory effect on cancer cells or activated immune cells. Examples of therapeutic agents include cytotoxic agents, chemotherapeutic agents, cytostatic agents, and immunomodulatory agents.

A "chemotherapeutic agent" is a chemical compound useful in the treatment of cancer.

A "cytotoxic effect" refers to the depletion, elimination and/or the killing of a target cell(s). A "cytotoxic agent" refers to an agent that has a cytotoxic and/or cytostatic effect on a cell.

A "cytostatic effect" refers to the inhibition of cell proliferation. A "cytostatic agent" refers to an agent that has a cytostatic effect on a cell, thereby inhibiting the growth and/or expansion of a specific subset of cells.

"Antibody-drug conjugate" or "ADC" refers to antibodies or antibody fragments thereof, including antibody derivatives that bind to IL-13-Rα2 and are conjugated to cytotoxic, cytostatic, and/or therapeutic agents.

"Anti-IL-13-Rα2 Antibody-Drug conjugate" refers to an anti-IL-13-Rα2 antibody or antigen binding fragment thereof, as described herein linked to a cytotoxic drug (D) via a linker (L).

"Linker (L)" describes the direct or indirect linkage of the antibody to the drug. Attachment of a linker to a mAb can be accomplished in a variety of ways, such as through surface lysines, reductive-coupling to oxidized carbohydrates, and through cysteine residues liberated by reducing interchain disulfide linkages. A variety of ADC linkage systems are known in the art, including hydrazone-, disulfide- and peptide-based linkages.

"Drug (D)" is any substance having biological or detectable activity, for example, therapeutic agents, detectable labels, binding agents, etc., and prodrugs, which are metabolized to an active agent in vivo. The terms drug, drug moiety, payload, and compound are used interchangeably.

"L-D" is a linker-drug moiety resulting from a cytotoxic drug (D) linked to a linker (L).

The term "epitope" refers to that portion of a molecule capable of being recognized by and bound by an antibody at one or more of the antibody's antigen-binding regions. Epitopes often consist of a chemically active surface grouping of molecules such as amino acids or sugar side chains and have specific three-dimensional structural characteristics as well as specific charge characteristics. The term "antigenic epitope" as used herein, is defined as a portion of a polypeptide to which an antibody can specifically bind as determined by any method well known in the art, for example, by conventional immunoassays. A "nonlinear epitope" or "conformational epitope" comprises noncontiguous polypeptides (or amino acids) within the antigenic protein to which an antibody specific to the epitope binds. Once a desired epitope on an antigen is determined, it is possible to generate antibodies to that epitope, e.g., using the techniques described in the present specification. During the discovery process, the generation and characterization of antibodies may elucidate information about desirable epitopes. From this information, it is then possible to competitively screen antibodies for binding to the same epitope. An approach to achieve this is to conduct competition and cross-competition studies to find antibodies that compete or cross-compete with one another e.g., the antibodies compete for binding to the antigen.

The term "binding affinity ($K_D$)" as used herein, is intended to refer to the dissociation rate of a particular antigen-antibody interaction. The $K_D$ is the ratio of the rate of dissociation ($K_d$), also called the "off-rate ($k_{off}$)", to the association rate ($K_a$), or "on-rate ($k_{on}$)". Thus, $K_D$ equals $k_{off}/k_{on}$ and is expressed as a molar concentration (M). It follows that the smaller the $K_D$, the stronger the affinity of binding. Therefore, a $K_D$ of 1 μM indicates weak binding affinity compared to a $K_D$ of 1 nM. $K_D$ values for antibodies can be determined using methods well established in the art. One method for determining the $K_D$ of an antibody is by using surface plasmon resonance, typically using a biosensor system such as a Biacore® system.

The term "specifically binds" as used herein in reference to the binding between an antibody and an IL-13-Rα2 antigen and the antibody binds the IL-13-Rα2 antigen with a $K_D$ less than about 30 nM as determined by surface plasmon resonance (SPR) at 25° C.

"Pharmaceutically acceptable salt" as used herein refers to pharmaceutically acceptable organic or inorganic salts of a molecule or macromolecule.

The term "potency" is a measurement of biological activity and may be designated as IC$_{50}$, or inhibitory concentration of an antibody or antibody drug conjugate to the antigen IL-13-Rα2, needed to inhibit 50% of growth of an IL-13-Rα2 positive cell line as described in Example 15.

"EC50" is a measurement of binding capacity and is defined as the half maximal effective concentration of an antibody or antibody-drug conjugate that is needed to produce a response halfway between the baseline and maximum.

The phrase "effective amount" or "therapeutically effective amount" as used herein refers to an amount necessary (at dosages and for periods of time and for the means of administration) to achieve the desired therapeutic result. An effective amount is at least the minimal amount, but less than a toxic amount, of an active agent which is necessary to impart therapeutic benefit to a subject.

The terms "inhibit" or "neutralize" as used herein with respect to bioactivity of an antibody of the invention mean the ability of the antibody to substantially antagonize, prohibit, prevent, restrain, slow, disrupt, eliminate, stop, reduce or reverse e.g. progression or severity of that which is being inhibited including, but not limited to, a biological activity.

The term "compete", as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

The terms "polynucleotide" or "nucleic acid molecule", as used herein, are intended to include DNA molecules and RNA molecules. A nucleic acid molecule may be single-stranded or double-stranded, but preferably is double-stranded DNA.

The polynucleotides that encode the antibodies of the present invention may include the following: only the coding sequence for the variant, the coding sequence for the variant and additional coding sequences such as a functional polypeptide, or a signal or secretory sequence or a pro-protein sequence; the coding sequence for the antibody and non-coding sequence, such as introns or non-coding sequence 5' and/or 3' of the coding sequence for the antibody. The term "polynucleotide encoding an antibody" encompasses a polynucleotide which includes additional coding sequence for the variant but also a polynucleotide which includes additional coding and/or non-coding sequence. It is known in the art that a polynucleotide sequence that is optimized for a specific host cell/expression system can readily be obtained from the amino acid sequence of the desired protein (see GENEART AG, Regensburg, Germany).

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

The term "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The term "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

The polynucleotides encoding the antibodies of the present invention will typically include an expression control polynucleotide sequence operably linked to the antibody coding sequences, including naturally-associated or heterologous promoter regions known in the art. Preferably, the expression control sequences will be eukaryotic promoter systems in vectors capable of transforming or transfecting eukaryotic host cells, but control sequences for prokaryotic hosts may also be used. Once the vector has been incorporated into the appropriate host cell line, the host cell is propagated under conditions suitable for expressing the nucleotide sequences, and, as desired, for the collection and purification of the antibodies. Preferred eukaryotic cell lines include the CHO cell lines, various COS cell lines, HeLa cells, myeloma cell lines, transformed B-cells, or human embryonic kidney cell lines. The most preferred host cell is a CHO cell line.

Antibodies

Antibodies of the invention can be produced using techniques well known in the art, e.g., recombinant technologies, phage display technologies, synthetic technologies or combinations of such technologies or other technologies readily known in the art (see, for example, Jayasena, S. D., Clin. Chem., 45: 1628-50 (1999) and Fellouse, F. A., et al, J. Mol. Biol., 373(4):924-40 (2007)).

Tables 1 and 2 below depict preferred CDRs for the antibodies of the present invention.

TABLE 1

| Antibody | LCDR1 | LCDR2 | LCDR3 |
|---|---|---|---|
| hu07 | TASLSVS STYLH SEQ ID NO: 14 | STSNLAS SEQ ID NO: 15 | HQYHRSP LT SEQ ID NO: 16 |
| hu08 | KASQDVG TAVA SEQ ID NO: 6 | SASYRST SEQ ID NO: 7 | QHHYSAPWT SEQ ID NO: 8 |

TABLE 2

| Antibody | HCDR1 | HCDR2 | HCDR3 |
| --- | --- | --- | --- |
| hu07 | TKYGVH SEQ ID NO: 10 | VKWAGGSTD YNSALMS SEQ ID NO: 11 | DHRDAMDY SEQ ID NO: 12 |
| hu08 | SRNGMS SEQ ID NO: 2 | TVSSGGSYI YYADSVKG SEQ ID NO: 3 | QGTTALAT RFFDV SEQ ID NO: 4 |

An embodiment of the present invention includes an antibody or antigen binding fragment thereof, that comprises:
 a) a light chain variable region comprising:
  i) a LCDR1 having an amino acid sequence selected from the group consisting of SEQ ID NOs: 6 and 14;
  ii) a LCDR2 having an amino acid sequence selected from the group consisting of SEQ ID NOs: 7 and 15; and
  iii) a LCDR3 having an amino acid sequence selected from the group consisting of SEQ ID NOs: 8 and 16; and
 b) a heavy chain variable region comprising:
  i) a HCDR1 having an amino acid sequence selected from the group consisting of SEQ ID NOs: 2 and 10;
  ii) a HCDR2 having an amino acid sequence selected from the group consisting of SEQ ID NOs: 3 and 11; and
  iii) a HCDR1 having an amino acid sequence selected from the group consisting of SEQ ID NOs: 4 and 12.

A preferred antibody or antigen binding portion thereof, of the invention comprises:
 a) a LCVR comprising: a LCDR1 of SEQ ID NO: 6, a LCDR2 of SEQ ID NO: 7, and a LCDR3 of SEQ ID NO: 8; and
 b) a HCVR comprising: a HCDR1 of SEQ ID NO: 2, a HCDR2 of SEQ ID NO: 3, and a HCDR3 of SEQ ID NO: 4.

Another preferred antibody or antigen binding portion thereof, of the invention comprises:
 a) a LCVR comprising: a LCDR1 of SEQ ID NO: 14, a LCDR2 of SEQ ID NO: 15, and a LCDR3 of SEQ ID NO: 16; and
 b) a HCVR comprising: a HCDR1 of SEQ ID NO: 10, a HCDR2 of SEQ ID NO: 11, and a HCDR3 of SEQ ID NO: 12.

Preferred monoclonal antibodies of the invention are referred to herein as hu08 (a humanized anti-IL-13-Rα2 IgG1 antibody); and, hu07 (a humanized anti-IL-13-Rα2 IgG1 antibody). The SEQ ID NOs of the amino acid sequences encoding mAbs hu08 and hu07 are provided in Table 3 below:

TABLE 3

| mAb | LC | HC | LCVR | LCDR1 | LCDR2 | LCDR3 | HCVR | HCDR1 | HCDR2 | HCDR3 |
| --- | --- | --- | --- | --- | --- | --- | --- | --- | --- | --- |
| hu08 | 51 | 50 | 5 | 6 | 7 | 8 | 1 | 2 | 3 | 4 |
| hu07 | 53 | 52 | 41 | 14 | 15 | 16 | 48 | 10 | 11 | 12 |

An embodiment of the invention is an antibody or antigen binding fragment thereof that specifically binds to the same IL-13Rα2 epitope as an antibody comprising a first amino acid sequence that is at least 90%, 92%, 94%, 95%, 96%, 97%, 98% or 99% identical to SEQ ID NO: 1 and a second amino acid sequence that is at least 90%, 92%, 94%, 95%, 96%, 97%, 98% or 99% identical to SEQ ID NO: 5.

Another embodiment of the invention is an antibody or antigen binding fragment thereof that specifically binds to the same IL-13Rα2 epitope as an antibody comprising a first amino acid sequence that is at least 90%, 92%, 94%, 95%, 96%, 97%, 98% or 99% identical to SEQ ID NO: 48 and a second amino acid sequence that is at least 90%, 92%, 94%, 95%, 96%, 97%, 98% or 99% identical to SEQ ID NO: 41.

In some embodiments, the antibody or antigen binding fragment thereof specifically binds to IL-13Rα2, and the antibody or fragment thereof competitively inhibits the binding of an antibody comprising a first amino acid sequence that is at least 90%, 92%, 94%, 95%, 96%, 97%, 98% or 99% identical to SEQ ID NO: 1 and a second amino acid sequence that is at least 90%, 92%, 94%, 95%, 96%, 97%, 98% or 99% identical to SEQ ID NO: 5.

In some embodiments, the antibody or antigen binding fragment thereof specifically binds to IL-13Rα2, and the antibody or fragment thereof competitively inhibits the binding of an antibody comprising a first amino acid sequence that is at least 90%, 92%, 94%, 95%, 96%, 97%, 98% or 99% identical to SEQ ID NO: 48 and a second amino acid sequence that is at least 90%, 92%, 94%, 95%, 96%, 97%, 98% or 99% identical to SEQ ID NO: 41.

Representative materials of the present invention were deposited in the American Type Culture Collection (ATCC) on Nov. 6, 2012. A vector having ATCC Accession No. PTA-13304 is a polynucleotide encoding a human anti-IL-13 antibody light chain variable region designated as hu08-VLv1.0, and vector having ATCC Accession No. PTA-13305 is a polynucleotide encoding a human anti-IL-13 antibody heavy chain variable region, designated hu08-VHv1.0. The deposits were made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. Section 122 and the Commissioner's rules pursuant thereto (including 37 C.F.R. Section 1.14 with particular reference to 886 OG 638).

Conjugation of Drug Moieties to an Antibody

The drug moiety has, or is modified to include, a group reactive with a conjugation point on the antibody. For example, a drug moiety can be attached by alkylation (e.g., at the epsilon-amino group lysines or the N-terminus of antibodies), reductive amination of oxidized carbohydrate, transesterification between hydroxyl and carboxyl groups, amidation at amino groups or carboxyl groups, and conjugation to thiols. In some embodiments, the number of drug moieties, p, conjugated per antibody molecule ranges from an average of 1 to 8; 1 to 7, 1 to 6, 1 to 5, 1 to 4, 1 to 3, or 1 to 2. In some embodiments, p ranges from an average of 2 to 8, 2 to 7, 2 to 6, 2 to 5, 2 to 4 or 2 to 3. In other embodiments, p is an average of 1, 2, 3, 4, 5, 6, 7 or 8. In some embodiments, p ranges from an average of about 1 to about 8; about 1 to about 7, about 1 to about 6, about 1 to about 5, about 1 to about 4, about 1 to about 3, or about 1 to about 2. In some embodiments, p ranges from about 2 to about 8, about 2 to about 7, about 2 to about 6, about 2 to about 5, about 2 to about 4 or about 2 to about 3. For examples of chemistries that can be used for conjugation, see, e.g., Current Protocols in Protein Science (John Wiley & Sons, Inc.), Chapter 15 (Chemical Modifications of Proteins).

Linkers

The drug moiety can be linked to an antibody by a linker. Suitable linkers include, for example, cleavable and non-cleavable linkers. A cleavable linker is typically susceptible to cleavage under intracellular conditions. Suitable cleavable linkers include, for example, a peptide linker cleavable by an intracellular protease, such as lysosomal protease or an endosomal protease. In exemplary embodiments, the linker can be a dipeptide linker, such as a valine-citrulline (val-cit), a phenylalanine-lysine (phe-lys) linker, or maleimido-capronic-valine-citruline-p-aminobenzyloxycarbonyl (vc) linker. Another linker is Sulfosuccinimidyl-4-[N-maleimidomethyl]cyclohexane-1-carboxylate (smcc). Sulfo-smcc conjugation occurs via a maleimide group which reacts with sulfhydryls (thiols, —SH), while its Sulfo-NHS ester is reactive toward primary amines (as found in Lysine and the protein or peptide N-terminus). Yet another linker is maleimidocaproyl (mc). Other suitable linkers include linkers hydrolyzable at a specific pH or a pH range, such as a hydrazone linker. Additional suitable cleavable linkers include disulfide linkers. The linker may be covalently bound to the antibody to such an extent that the antibody must be degraded intracellularly in order for the drug to be released e.g. the mc linker and the like.

The preferred linkers of the present invention are maleimidocapronic-valine-citruline-p-aminobenzyloxycarbonyl (vc) and maleimidocaproyl (mc).

Engineered Fc Polypeptide

It has been previously reported that certain residues presumably present on the surface of the CH2 or CH3 domain of the heavy chain of antibodies, or on the constant domain of the light chain, or otherwise accessible, are suitable for the substitution of the naturally-occurring wild type amino acid with, for example, cysteine, and are therefore useful to engineer a site capable of conjugation to various agents (see U.S. Provisional Patent Application U.S. Ser. No. 61/580,169) herein incorporated by reference.

Amino acid modifications can be made by any method known in the art and many such methods are well known and routine for the skilled artisan. For example, but not by way of limitation, amino acid substitutions, deletions and insertions may be accomplished using any well-known PCR-based technique. Amino acid substitutions may be made by site-directed mutagenesis (see, for example, Zoller and Smith, 1982, Nucl. Acids Res. 10:6487-6500; and Kunkel, 1985, Proc. Natl. Acad. Sci USA 82:488).

In some embodiments, the engineered Fc polypeptide of the disclosure may be used to prepare an antibody, or antigen binding fragment thereof, such that the antibody or fragment thereof thereby comprises the engineered Fc region which can be used to conjugate, at the engineered residue (i.e., the amino acid substituted compared to wild type unmodified Fc), a wide variety of moieties.

In some embodiments, the engineered kappa light chain constant polypeptide of the disclosure may be used to prepare an antibody, or antigen binding fragment thereof, such that the antibody or fragment thereof thereby comprises an engineered CL region comprising an amino acid mutation, or portion thereof, which can be used to conjugate, at the engineered amino acid residue, a wide variety of moieties.

The IL-13-Rα2 antibodies of the present invention may encompass an engineered Fc polypeptide where 1, 2, or more amino acids chosen from positions: 347, 392, 398, 422 and 443 of the antibody heavy chain wherein the numbering system of the constant region is that of the EU index as set forth in Kabat et al. (1991, NIH Publication 91-3242, National Technical Information Service, Springfield, Va., hereinafter "Kabat") of a parent, native, or wild type antibody, substituted with another amino acid (including natural and non-natural/synthetic amino acids).

It should be noted that a single substitution in an Fc polypeptide, for example of a cysteine residue, normally results in the display of two corresponding residues in the resultant IgG antibody due to the homodimeric nature of IgG antibody molecules. Thus, the resultant engineered IgG antibodies of the invention may display at least 1, 2, 3, 4, or more reactive groups for the purpose of conjugation to a drug or compound. In an embodiment, one or more of the substitutions is with a cysteine residue, and the resulting engineered antibodies may display at least 1, 2, 3, 4, or more thiol groups for the purpose of conjugation to a drug or compound.

In other embodiments, the engineered Fc polypeptide of the disclosure comprises one or more substitutions selected from the positions 347, 392, 398, 422 and 443, of the heavy chain of an antibody, and wherein the numbering system of the constant region is that of the EU index as set forth in Kabat et al. (supra).

In some embodiments, the engineered Fc polypeptide of the disclosure comprises at least one pair of amino acid substitutions selected from the group consisting of: (a) the amino acid sequence of SEQ ID NO:33; and, (b) the amino acid sequence of SEQ ID NO:34.

In some embodiments, the engineered Fc polypeptide of the disclosure comprises one substitution selected from the group consisting of (a) the amino acid sequence of SEQ ID NO:28; and (b) the amino acid sequence of SEQ ID NO:29.

Engineered CK Polypeptide

The IL-13-Rα2 antibodies of the present invention may encompass an engineered antibody light chain constant region (LC), or a portion thereof, where 1, 2, or 3 amino acids chosen from positions 111, 183, or 188, of the antibody light chain, wherein the numbering system of the light chain constant region is that of the Kabat numbering system as set forth in Kabat et al. (1991, NIH Publication 91-3242, National Technical Information Service, Springfield, Va., hereinafter "Kahat"), of a parent, native, or wild type antibody, substituted with another amino acid (including natural and non-natural/synthetic amino acids).

In some embodiments, the engineered LC polypeptide of the disclosure comprises one or more substitutions selected from the group consisting of (a) the amino acid sequence of SEQ ID NO:30; (b) the amino acid sequence of SEQ ID NO:31; and (c) the amino acid sequence of SEQ ID NO:32.

In other embodiments, due to the dimeric nature of many antibodies (e.g., IgGs comprise two light chains and two heavy chains each heavy chain comprising an Fc polypeptide), an antibody of the invention may comprise at least one engineered Fc polypeptide and may further comprise at least one engineered light chain constant polypeptide thereby providing at least two site-specific conjugation sites—one in the Fc polypeptide and another in the CL polypeptide. Preferred antibodies of the invention that comprise at least one engineered Fc polypeptide and at least one engineered light chain constant region polypeptide selected from group consisting of L443C/kA111C (SEQ ID NOS: 28 and 30), L443C/kK183C (SEQ ID NOS: 28 and 31), Q347C/kA111C (SEQ ID NOS: 29 and 30), and Q347C/kK183C (SEQ ID NOS: 29 and 31).

MAC Conjugation Technology

The term multifunctional antibody conjugate, or MAC, refers to an antibody as defined herein, or antigen binding portion thereof, covalently conjugated through the constant kappa region to at least one drug moiety that exerts a biological effect to a target. Preferably, the antibody, or antigen binding portion thereof comprises K90 and H91 of SEQ ID NO:52, SEQ ID NO:53, SEQ ID NO:54, or SEQ ID NO:55, and the drug moiety is conjugated at K90. MAC technology has been described previously in WO2012/007896 and in U.S. Ser. No. 61/584,675, which are incorporated herein by reference.

The drug moiety exerts a biological effect on the target and may be a peptide, small molecule, protein, nucleic acid molecule, toxin, aptamer, or antigen binding antibody or fragment thereof. The drug moiety may be a drug having cytotoxic activity against target cells. In some aspects, the cytotoxin is in the class of compounds known as auristatin. Representative auristatins are compounds 0101 and 3377 described herein in Example 13.

Reaction of the drug moiety with the constant light domain of an antibody is particularly desirable to minimize, or prevent, any interference with binding of the Fc portion of the antibody to Fc receptors (such as FcγR and FcRn) or binding of the antibody to its respective target. Conversely, conjugation of the respective drug moiety to the Fc portion of an antibody may decrease the antibody half-life in vivo and/or its capacity to interact with the immune system (effector function). Conjugation of the drug moiety in the variable heavy chain (VH) or variable light chain (VL) region of the antibody carry a risk of diminishing the binding of the antibody to its cognate.

One of the advantages of the MAC technology is that depending on the reagents and reaction conditions (especially the leaving group ester and molar ratio of linker antibody), compositions and samples of the invention can be generated with a defined number of drug moieties relative to a defined number of antibodies. This can be especially useful when balancing the relative reactivity's and therapeutic windows of the drug moiety and antibody. Moreover, in some situations, increasing the number of drug moieties per antibody beyond a certain threshold may not result in increased target binding or therapeutic effect. It is useful therefore, to be able to control the number of drug moieties conjugated per antibody, and in doing so, direct the location of conjugation so as to minimize Fc or combining site interference. In some situations, therefore, aspects of the invention that allow for reduced conjugation, preferentially decorating only a single lysine residue, such as K90 of the hu08 LC constant region, SEQ ID NO: 52, SEQ ID NO:53, SEQ ID NO:54, or SEQ ID NO:55, can be advantageous. Furthermore, whereas conjugation to K90 is reliable and robust, conjugation to other antibody surface lysines, each of slightly different reactivity and pI can result in an heterogeneous sample of conjugated antibodies that can release conjugated molecules at inopportune or irregular times, such as during circulation and prior to delivery of the drug moiety to the target by antibody recognition.

A further aspect of the present invention is the discovery that certain mutations of D77 of the wild type constant kappa chain (SEQ ID NO: 55) improves the accessibility and/or reactivity of the K90 site for drug conjugation. In addition, the present invention provides for known polymorphisms of the kappa chain V/A at position 45 and A/L at position 83 (giving the 3 identified human constant kappa polymorphisms Km(1): V45/L83, Km(1,2): A45/L83, and Km(3) A45/V83). Accordingly, the present invention provides for MACs comprising SEQ ID NO:53. In some aspects, the present invention provides for a MAC of Km(3) polymorphism, wherein the kappa constant domain is selected from the group consisting of SEQ ID NO:52, SEQ ID NO:54 and SEQ ID NO:55.

The present invention further provides an antibody that specifically binds to human IL-13Rα2 wherein said antibody has a LC constant region as shown in SEQ ID NO: 52, said LC constant region having a lysine residue at position 80 (K80) and an alanine residue substituted for an aspartic acid residue at position 77 (D77A).

The present invention further provides an antibody that specifically binds to human IL-13Rα2 wherein said antibody has a LC constant region as shown in SEQ ID NO: 53, wherein position 45 is V or A, position 83 is A or L, and position 77 is selected from the group consisting of A, G, I, V, L, R, S, T, Q, P, N, M, H and W. In some aspects, where position 45 is V, position 83 is L. In some aspects of SEQ ID NO:53, position 77 is selected from the group consisting of A, G, I, V, L, R, S, T, Q, P, N, M, H and W. The variability of residues at positions 45 and 83 in SEQ ID NO:53 may be selected so as to only provide for any one, two or all three of the Km(1), Km(1,2), and Km(3) polymorphisms.

The present invention further provides an antibody that specifically binds to human IL-13Rα2 wherein said antibody has a LC constant region as shown in SEQ ID NO: 54, wherein position 77 is selected form the group consisting of A, G, I, V, L, R, S, T, Q, P, N, M, H and W.

The present invention further provides an antibody that specifically binds to human IL-13Rα2 wherein said antibody has a LC constant region as shown in SEQ ID NO: 55.

Therapy for Cancer

Cancers, including, but not limited to, a tumor, metastasis, or other disease or disorder characterized by uncontrolled cell growth, can be treated or prevented by administration of an antibody-drug conjugate of the present invention.

Exemplary anti-IL-13-Rα2 ADCs are useful for treating cancer in which IL-13-Rα2 is expressed or overexpressed, relative to normal (e.g., non-cancerous tissue). Treatment or prevention of an IL-13-Rα2-expressing cancer, according to the methods described herein, can be achieved by administering to a subject in need of such treatment an effective amount of an anti-IL-13-Rα2 ADC. In some embodiments, an anti-IL-13-Rα2 full length antibody or antigen-binding fragment thereof or derivative thereof that is conjugated to a cytotoxic agent will be administered. In some exemplary embodiments, an ADC of the present invention will (i) bind to IL-13-Rα2 expressing cancer cells, and (ii) exert a cytotoxic or cytostatic effect to, for example, inhibit the proliferation of the IL-13-Rα2 expressing cancer cells, or kill IL-13-Rα2 expressing cancer cells.

In other embodiments, the anti-IL-13-Rα2 ADCs are co-administered with another therapeutic agent, or administered sequentially with another therapeutic agent. In some embodiments, the anti-IL-13-Rα2 ADCs are co-administered with chemotherapeutics, including standard of care chemotherapeutics, or administered sequentially.

In some embodiments, the other therapeutic agent will be an agent that is standard of care for the specific disease to be treated or is part of a salvage regimen for the specific disease to be treated. Anti-cancer agents and chemotherapeutic regimens include, for example, anti-cancer antibodies, including, for example, anti-CD52 antibodies (e.g., Alemtuzumab), anti-CD20 antibodies (e.g., Rituximab), and anti-CD40 antibodies (e.g., SGN40); chemotherapeutic regimens including, for example, CHOP (cyclophosphamide, doxorubicin, vincristine, and prednisone); CVP (cyclophosphamide, vincristine, and prednisone); RCVP (Rituximab+CVP); RCHOP (Rituximab+CHOP); RICE (RituximAb+ifosamide, carboplatin, etoposide); RDHAP, (Rituximab+dexamethasone, cytarabine, cisplatin); RESHAP (Rituximab+etoposide, methylprednisolone, cytarabine, cisplatin); gemcitabine; combination treatment with vincristine, prednisone, and anthracycline, with or without asparaginase; combination treatment with daunorubicin, vincristine, prednisone, and asparaginase; combination treatment with teniposide and Ara-C (cytarabine); combination treatment with methotrexate and leucovorin; combination treatment with bleomycin, doxorubicin, etoposide, mechlorethamine, prednisone, vinblastine, and vincristine; small molecule inhibitors; and proteosome inhibitors including, for example, bortezomib.

In some embodiments, methods for treating cancer including administering to a patient in need thereof an effective amount of an anti-IL-13-Rα2 ADC in combination with radiation treatment, and optionally another therapeutic agent. In some embodiments, the anti-IL-13-Rα2 ADC is administered concurrently or sequentially with an anti-cancer agent (e.g., a chemotherapeutic agent) and/or with radiation therapy. In some embodiments, the chemotherapeutic agent or radiation therapy is administered at least an hour, five hours, 12 hours, a day, a week, a month, several months (e.g., up to three months), prior or subsequent to administration of a compound of the present invention.

The ADCs of the present invention can be in the form of a pharmaceutical composition for administration that are formulated to be appropriate for the selected mode of administration, and pharmaceutically acceptable diluent or excipients, such as buffers, surfactants, preservatives, solubilizing agents, isotonicity agents, stabilizing agents, carriers, and the like. Remington's Pharmaceutical Sciences, Mack Publishing Co., Easton Pa., $18^{th}$ ed., 1995, provides a compendium of formulation techniques as are generally known to practitioners.

These pharmaceutical compositions may be administered by any means known in the art that achieve the generally intended purpose to treat cancer. The preferred route of administration is parenteral, defined herein as referring to modes of administration that include but not limited to intravenous, intramuscular, intraperitoneal, subcutaneous, and intraarticular injection and infusion. The dosage administered will be dependent upon the age, health, and weight of the recipient, kind of concurrent treatment, if any, frequency of treatment, and the nature of the effect desired.

Compositions within the scope of the invention include all compositions wherein an ADC is present in an amount that is effective to achieve the desired medical effect for treating cancer. While individual needs may vary from one patient to another, the determination of the optimal ranges of effective amounts of all of the components is within the ability of the clinician of ordinary skill.

Diagnostic

The antibodies or antibody fragments of the invention can also be used to detect hIL-13-Rα2 in a biological sample in vitro or in vivo. In one embodiment, the anti-hIL-13-Rα2 antibodies of the invention are used to determine the level of hIL-13-Rα2 in a tissue or in cells derived from the tissue. In a preferred embodiment, the tissue is a diseased tissue. In a preferred embodiment of the method, the tissue is a tumor or a biopsy thereof. In a preferred embodiment of the method, a tissue or a biopsy thereof is first excised from a patient, and the levels of hIL-13-Rα2 in the tissue or biopsy can then be determined in an immunoassay with the antibodies or antibody fragments of the invention. The tissue or biopsy thereof can be frozen or fixed. The same method can be used to determine other properties of the hIL-13-Rα2 protein, such as its level of cell surface levels, or cellular localization.

The above-described method can be used to diagnose a cancer in a subject known to or suspected to have a cancer, wherein the level of hIL-13-Rα2 measured in said patient is compared with that of a normal reference subject or standard. Said method can then be used to determine whether a tumor expresses hIL-13-Rα2, which may suggest that the tumor will respond well to treatment with the antibody-drug conjugates of the present invention. Preferably, the tumor is a cancer of the lung, colon, stomach, pancreatic, ovarian, malignant gliomas, and melanoma, or other carcinomas in which hIL-13-Rα2 is expressed, and other cancers yet to be determined in which hIL-13-Rα2 is expressed predominantly.

An embodiment of the invention is a method of treating an IL-13-Rα2 expressing cancer said method comprising: determining the level of hIL-13-Rα2 in a biological sample comprising the steps of: obtaining a sample from a subject suspected to have cancer; testing said sample in a immunoassay using an antibody of the present invention; determining the cell surface levels of hIL-13-Rα2 on said sample; comparing the cell surface levels of hIL-13-Rα2 with that of a normal reference subject or standard; and administering an antibody-drug conjugate of the present invention to said subject.

The present invention further provides for monoclonal antibodies, humanized antibodies and epitope-binding fragments thereof that are further labeled for use in research or diagnostic applications. In preferred embodiments, the label is a radiolabel, a fluorophore, a chromophore, an imaging agent or a metal ion.

A method for diagnosis is also provided in which said labeled antibodies or epitope-binding fragments thereof are administered to a subject suspected of having a cancer, and the distribution of the label within the body of the subject is measured or monitored.

Kit

The present invention also includes kits, e.g. comprising a described cytotoxic conjugate and instructions for the use of the cytotoxic conjugate for killing of particular cell types. The instructions may include directions for using the cytotoxic conjugates in vitro, in vivo or ex vivo. Typically, the kit will have a compartment containing the cytotoxic conjugate. The cytotoxic conjugate may be in a lyophilized form, liquid form, or other form amendable to being included in a kit. The kit may also contain additional elements needed to practice the method described on the instructions in the kit, such a sterilized solution for reconstituting a lyophilized powder, additional agents for combining with the cytotoxic conjugate prior to administering to a patient, and tools that aid in administering the conjugate to a patient.

All publications and patent documents cited above or in the following examples are hereby incorporated by reference in their entirety for all purposes to the same extent as if each were so individually denoted.

The invention will be further described with reference to the following examples; however, it is to be understood that the invention is not limited to such examples.

The following examples of specific aspects for carrying out the present invention are offered for illustrative purposes only, and are not intended to limit the scope of the present invention in any way.

Example 1

Generation and Evaluation of Murine Anti-IL-13Rα2 Antibodies mu07 and mu08

Anti-hIL-13Rα2 antibodies were prepared in mice using human IL-13Rα2 antigen and standard methods for immunization. (Zhang, C., *Antibody Methods and Protocols*, Methods in Molecular Biology, vol. 901, DOI 10.1007/978-1-61779-931-0_7, © Springer Science+Business Media, LLC 2012). Two murine antibodies, mu07 and mu08, were identified that bound to A375 cells, a melanoma cell line which endogenously expresses high levels of IL-13Rα2 on the cell surface.

An important characteristic of an antibody in an ADC is rapid internalization after binding to its receptor. The antibodies mu07 and mu08 were evaluated and were found to be internalized 38% and 31% respectively, after a1 hour incubation with A375 cells at 37° C.

Example 2

Variable Regions of Murine Anti-IL-13Rα2 Antibodies mu07 and mu08

The mu07 and mu08 anti-IL-13Rα2 antibody heavy chain and light chain variable regions were cloned using the SMARTer® cDNA synthesis system (Clontech Laboratories Inc. of Mountain View, Calif.) followed by PCR amplification. The cDNA was synthesized by standard techniques and amplified by PCR using a primer which anneals to the SMARTer® IIA oligo sequence and mouse constant region specific primer (mouse Kappa for the light chain and mouse IgG1 for the heavy chain) with PCR SuperMix High Fidelity (Invitrogen, Carlsbad, Calif.). Heavy chain and light chain variable region PCR products were subcloned into the pCR4-TOPO vector (Invitrogen, Carlsbad, Calif.) and the nucleic acid sequence was determined.

The amino acid sequences of the mu07 and mu08 heavy chain variable regions are set forth as amino acid residues of SEQ ID NO:25 and amino acid residues of SEQ ID NO:23, respectively. The amino acid sequences of the mu07 and mu08 light chain variable regions are set forth in SEQ ID NO:26 and SEQ ID NO:24, respectively.

Example 3

Binding Specificity and Binding Kinetics of Chimeric Antibodies ch07 and ch08

Chimeric antibodies 07 and 08 (ch07 and ch08) were constructed having murine heavy chain and light chain variable region sequences with human IgG1 heavy chain constant regions and human kappa light chain constant regions using methods known in the art. To assess the binding activity and specificity of ch07 and ch08, a standard direct ELISA protocol was performed utilizing recombinant hIL-13-Rα2 and hIL-13Ra1, receptors for IL-13 cytokine. The binding was detected by horseradish peroxidase (HRP) conjugated goat anti-human IgGKappa. The results in FIG. 1 demonstrate that both chimeric antibodies can bind specifically to hIL-13Rα2 but not hIL-13Rα1. The ED50 is 0.15 nM and 0.076 nM for ch07 and ch08, respectively.

To assess the binding kinetics of the ch07 and ch08 antibodies, SPR (Surface Plasmon Resonance) experiments were conducted on a Biacore® T100 or T200 instrument using a Biacore® human Fab Capture Kit (GE Healthcare). All data was analyzed using the Biacore® T100 evaluation software version 2.0 with a 1:1 Langmuir binding model.

$K_a$, $K_d$ and KD are shown on Table 5. At pH7.4, binding affinity to hIL-13-Rα2 for both ch07 and ch08 are in the pM range, 648pM and 964pM, respectively. ch07 dissociation from hIL-13-Rα2 is about 2 fold slower than ch08. At pH6.0, ch07 and ch08 binding affinity to hIL-13-Rα2 are in the low nM range. Dissociation rates of ch08 and ch07 are very similar. Higher KDs at pH6.0 than pH7.4 are due to a slower association rate.

TABLE 5

Kinetics analysis of chimeric antibody ch07 and ch08

| | Ka (1/Ms) | Kd (1/s) | KD(M) |
| --- | --- | --- | --- |
| ch07-pH 7.4 | 3.61E+05 | 2.34E−04 | 6.48E−10 |
| ch07-pH 6.0 | 6.43E+04 | 3.37E−04 | 5.24E−9 |
| ch08-pH 7.4 | 4.32E+05 | 4.16E−04 | 9.64E−10 |
| ch08-pH 6.0 | 7.12E+04 | 3.81E−04 | 5.36E−9 |

Example 4

Binding Epitopes of Antibodies ch07 and ch08

Figure 2A:
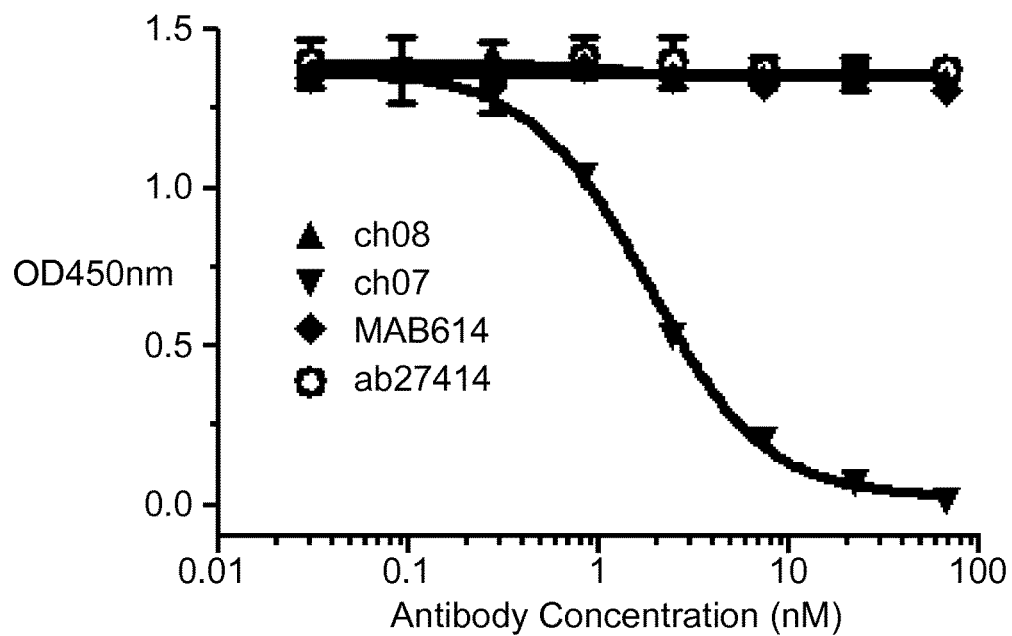
FIG. 2A and FIG. 2B: ch07, ch08 and antibodies MAB614 and ab27414 have distinct binding epitopes to IL-13Rα2.
Figure 2B:
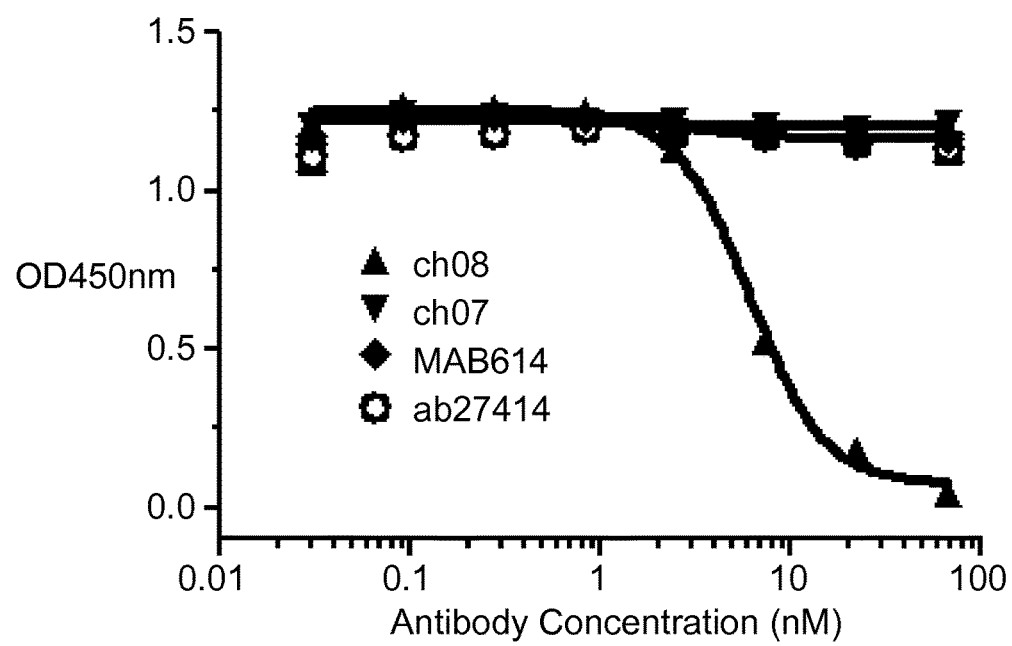

A competition ELISA was performed to examine whether ch07 and ch08 have distinct binding epitopes. Prior to the competition ELISA experiment, ch07 and ch08 were biotinylated. The EC50 of the biotinylated ch07 (biotin-ch07) and ch08 (biotin-ch08) were determined by direct standard ELISA. For the competition ELISA, recombinant hIL-13-Rα2 was coated onto 96-well plates at 50 ul of 2 μg/mL in PBS overnight at 4° C. The plates were then blocked and washed following a standard ELISA protocol. 3-fold serially diluted ch07 and ch08 (2× final concentration) were mixed with a constant amount of biotin-ch07 (FIG. 2A) or biotin-ch08 (FIG. 2B), respectively and were added to the plate and incubated for 1 hour at room temperature. The amount of biotinylated chimeric antibody bound was detected by HRP conjugated streptavidin at 1:5000 for 1 hour. The results are shown in FIG. 2. Unlabelled chimeric ch07 competes in binding to hIL-13-Rα2 with biotin-ch07 while unlabelled ch08 shows no sign of competition (FIG. 2A). Similar results are obtained when the same set of antibodies were used to compete with biotin-ch08 (FIG. 2B). This clearly demonstrates that antibodies ch07 and ch08 have distinct binding epitopes to hIL-13Rα2.

The competition ELISA was also performed with two commercially available antibodies, monoclonal mouse IgG1, MAB614 (R&D Systems) and monoclonal mouse IgG1, ab27414 (Abcam). FIG. 2A and FIG. 2B show that both commercial antibodies do not compete with either biotin-ch07 or biotin-ch08 for binding to IL-13Rα2, indicating that antibodies ch07 and ch08 have different binding epitopes than the two commercial antibodies.

Figure 2C:
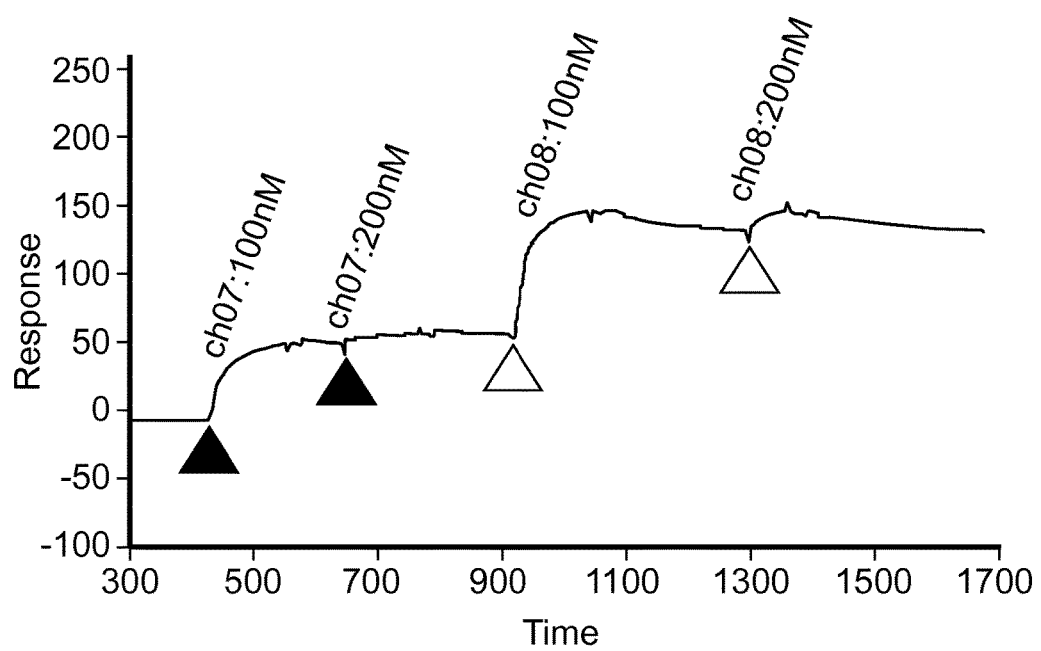
FIG. 2C: Biacore analysis indicating that ch07 and ch08 lack competition in binding.

This result was confirmed by a BiaCore experiment. About 100RU of hIL-13-Rα2 was immobilized on CM5 chip using amine coupling chemistry. ch07 (100 nM and 200 nM) and ch08 (100 nM and 200 nM) were sequentially injected over hIL-13-Rα2 experiment channel and control channel at flow rate 10 ul/min for 150 s. 50 RU was reached when 100 nM ch07 was injected to immobilized hIL-13Rα2. No further RU increased when ch07 concentration was increased to 200 nM, indicating that the binding sites on hIL-13-Rα2 for ch07 were saturated. With the injection of 100 nM ch08, 100 RU was added. This positive binding signal indicates that the two antibodies lack competition. The results further confirm that antibodies ch07 and ch08 have different binding epitopes (FIG. 2C).

Example 5 ch07 and ch08 Neutralization Studies

Figure 3:
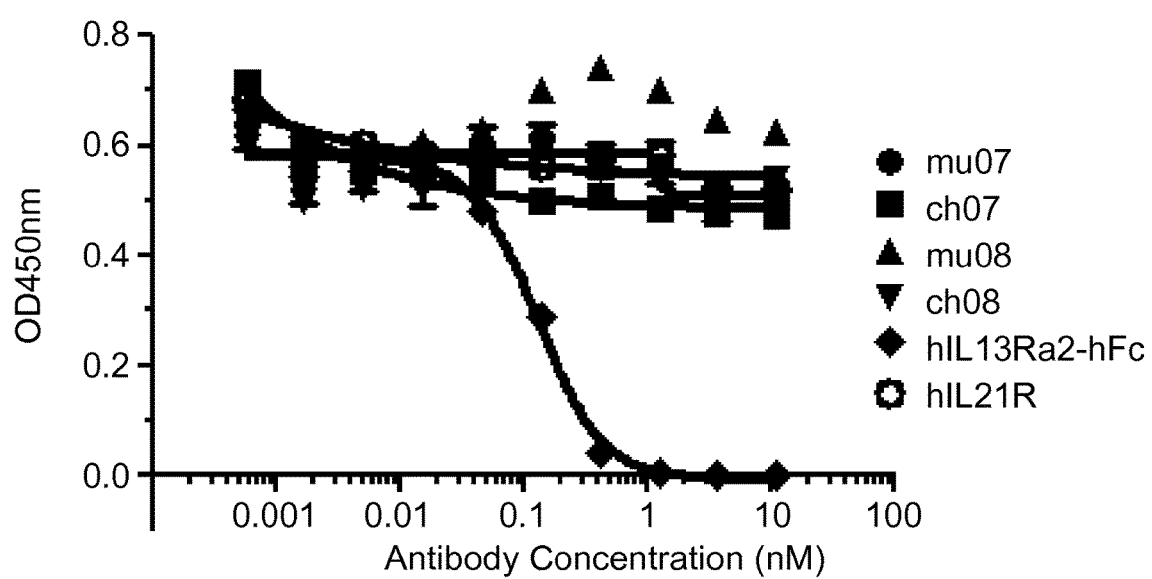
FIG. 3: ch07 and ch08 are non-neutralizing antibodies.

In order to assess whether ch07 and ch08 can neutralize IL-13 function, a competition ELISA was performed. An anti-Flag Ab was coated onto 96-well plates and incubated overnight at 4° C. Plates were then blocked and washed following standard ELISA protocol. A 3-fold serial dilution of mouse antibodies, chimeric antibodies, positive control naked IL-13Rα2, and negative control hIL-21R were incubated with a constant amount of biotinylated IL-13Rα2-Fc (4×ED50) and a constant amount of IL-13 (4×ED50) at RT for 1 h. 100 ul of the complex was added to the ELISA plate and incubated for 1 hour at room temperature. The amount of biotin-IL-13-Rα2 bound was detected by HRP conjugated streptavidin at 1:5000 for 1 hour. The results are shown in FIG. 3. Both antibodies 07 and 08 (murine and chimeric forms) do not compete with IL-13 for the IL-13-Rα2 binding site while naked IL-13Rα2 competes with biotinylated IL-13Rα2. This indicates that antibodies 07 and 08 (murine and chimeric forms) are non-neutralizing antibodies.

Example 6

Humanization of mu08

Monoclonal murine antibody mu08 (Seq ID NOs: 23 and 24) was humanized utilizing DP-54 and DPK9 as human acceptor frameworks. Humanized 08 antibodies (hu08) were prepared by CDR grafting with or without back mutations. The CDRs of the murine mu08 antibody were identified using the Kabat scheme.

A hu08 heavy chain variable region (VH version 1.0) was constructed by directly grafting the CDRs of mu08 onto a human DP-54 framework region. The version 1.1 was made by back mutations of frame work DP-54 at positions A40T, G42D, G44R and N83S. Both v1.0 and v1.1 were cloned into pSMED2 vector containing the hIgG1 constant region. The nucleotide sequences encoding humanized hu08 heavy chain variable regions are SEQ ID: NO: 17 for v1.0 and SEQ ID: NO: 20 for v1.1. The amino sequences encoding hu08 heavy chain variable regions are SEQ ID: NO: 1 for v1.0 and SEQ ID: NO: 19 for v1.1.

A hu08 light chain variable region (VK version 1.0) was constructed by directly grafting the CDRs of murine mu08 onto a human DPK9 framework region. The version 1.1 was made by back mutations of frame work DPK9 at positions K39I, S60D, T72S, T73F and T74I. Both versions v1.0 and v1.1 were cloned into pSMEN3 vector containing the hIg-Kappa constant region. The nucleotide sequences encoding hu08 light chain variable regions are SEQ ID: NO: 18 for v1.0 and SEQ ID: NO: 22 for v1.1. The amino acid sequences encoding hu08 light chain variable regions are SEQ ID: NO: 5 for v1.0 and SEQ ID: NO: 21 for v1.1.

Example 7

Characterization of Humanized hu08

Humanized hu08 binding to recombinant hIL-13-Rα2 was evaluated by a standard direct ELISA. Recombinant hIL-13-Rα2 was coated onto a 96-well plate. Serially diluted chimeric antibodies or humanized antibodies in combinations of heavy and light chains of versions 1.0 and 1.1 e.g. hu08 v1.0 HC/1.0 LC, hu08 v1.0 HC/v1.1 LC, hu08 v1.1 HC/v1.0 LC, and hu08 v1.1 HC/v1.1 LC, were added to the plate and incubated at room temperature for 1-2 hours. The binding was detected by HRP conjugated goat anti-human Ig Kappa. The results are shown in Table 6 below and demonstrate that all four combinations of humanized antibodies are able to bind to recombinant hIL-13-Rα2 and the ED50 is comparable to ch08.

Standard FACS (Fluorescent Activated Cell Sorter) analysis was performed to assess the binding activity of the antibodies to cell surface IL-13Rα2. A375 cells were washed with ice-cold PBS containing 1% bovine serum albumin and 0.001% sodium azide. Cells were incubated with serial dilutions of antibodies hu08 v1.0 and hu08 v1.1 e.g. hu08 v1.0 HC/1.0 LC, hu08 v1.0 HC/v1.1 LC, hu08 v1.1 HC/v1.0 LC, and hu08 v1.1 HC/v1.1 LC, for 30 min at 4° C. and then stained with phosphatidylethanolamine-labeled goat anti-human IgG, fixed in PBS containing 4% paraformaldehyde, and analyzed on a FACScan® (BD Biosciences). The data is consistent with the binding to recombinant receptor and illustrates that the binding to cell surface antigen for all 4 combinations is comparable to ch08 (Table 6).

A competition ELISA was performed to assess whether hu08 1.0 and hu08 v1.1 compete with ch08 for IL-13-Rα2 binding. Recombinant hIL-13-Rα2 was coated onto 96-well plates at 50 ul of 2 µ/ml in PBS overnight at 4° C. Plates were then blocked and washed following standard ELISA protocol. A 3-fold serially diluted ch08, hu08 1.0 and hu08 v1.1, and negative control ch07 (2× final concentration) were mixed with biotinylated ch08 (2×EC$_{50}$). 50 µl of the antibody and biotin-ch08 mixture were added to the plate and incubated for 1 hour at room temperature. The amount of biotin-ch08 bound was detected by HRP conjugated streptavidin. The results are shown in Table 6. All 4 combinations of humanized antibodies are similar to chimeric antibody ch08 in competing with biotinylated ch08, indicating that hu08 1.0 and hu08 v1.1 retained the same binding epitope as ch08 and have similar affinity to soluble and cell surface IL-13-Rα2.

TABLE 6

| Antibody | EC50 (nM) rec hIL-13Rα2 | EC50 (nM) A375 cells | IC50 (nM) Biotin-ch08 |
|---|---|---|---|
| ch08Hc + Lc | 0.152 | 5.637 | 1.979 |
| hu08 v1.0/1.0 | 0.175 | 4.098 | 2.120 |
| hu08 v1.0/1.1 | 0.143 | 6.522 | 2.144 |
| hu08 v1.1/1.0 | 0.163 | 4.152 | 2.562 |
| hu08 v1.1/1.1 | 0.198 | 5.157 | 3.164 | hu08 v1.0 HC/v1.0 LC and hu08 v1.1 HC/v1.1 LC were scaled up to generate purified proteins. Both antibodies were transiently expressed into HEK293F suspension cells. Surprisingly, humanization of 08 has improved the antibody production yield by 5-6 fold compared to the yield of ch08 (Table 7).

TABLE 7

| Antibody name | Expression level (ug/ml) |
|---|---|
| ch08 | 15 |
| hu08v1.0/1.0 | 89.6 |
| hu08v1.1/1.1 | 72.3 |

There is a direct correlation between the thermal stability of a protein or protein domain with the overall stability of the protein or protein domain. A higher melting point of a protein or protein domain often provides improved manufacturability and longer shelf life/stability. Thermal stability of ch08 and hu08 (v 1.0 and v1.1) was examined by Differential Scanning calorimetry (DSC). Thermal unfolding of chimeric and humanized antibodies by DSC was performed using a standard protocol on a MicroCal VP-DSC instrument. Both of the humanized antibodies, hu08 v1.0/1.0 and hu08 v1.1/1.1, show a higher Tm2 (Fab) than the chimeric version ch08 (Table 8). This demonstrates that humanization of cu08 improves the thermal stability of this antibody.

TABLE 8

| Antibody | CH2 Tm1 (° C.) | Fab Tm2 (° C.) | CH3 Tm3 (° C.) |
|---|---|---|---|
| ch08 | 73.41 + 0.47 | 70.44 + 0.04 | 84.35 + 0.09 |
| hu08v1.0/1.0 | 73.48 ± 0.19 | 80.29 ± 0.02 | 85.48 ± 0.14 |
| hu08v1.1/1.1 | 71.12 + 0.13 | 80.23 + 0.02 | |

The binding kinetics of hu08 antibodies was conducted on a Biacore® T100 as described above with the results shown in Table 9

TABLE 9

| Antibody | Antigen | pH | ka (1/Ms)on | kd (1/s)off | KD (nM) |
|---|---|---|---|---|---|
| hu08 v1.0 | hIL-13Rα2 | 7.4 | 9.75E+04 | 2.46E-04 | 2.52E-09 |
| hu08 v1.0 | hIL-13Rα2 | 6.0 | 5.29E+04 | 2.34E-04 | 4/42E-09 |

Example 8

Humanization of mu07

The general strategy of humanizing monoclonal murine antibody mu07 is the same as described for mu08 in Example 6. A humanized hu07 heavy chain variable region (VH version 1.0) was constructed by directly grafting the CDRs of mu07 onto a human DP-54 framework region. The versions 1.1-1.5 were made by back mutations of frame work DP-54 at various positions (Table 10). All versions were cloned into pSMED2 vector containing hIgG1 constant region.

A hu07 light chain variable region (VK version 1.0) was constructed by directly grafting the CDRs of mu07 onto a human DPK9 framework region. The versions 1.1-1.7 were made by back mutations of frame work DPK9 at various positions (Table 10). All versions were cloned into pSMEN3 vector containing hIg Kappa constant region. SEQ ID numbers of the amino acid sequences encoding hu07 variable regions are listed in Table 10.

TABLE 10

| | hu07 VH | | | hu07 VK | | |
|---|---|---|---|---|---|---|
| VH Variants | aa SEQ ID | Back-mutation | VL Variants | aa SEQ ID | Back-mutation | |
| hu07 VH v1.0 | 9 | | hu07 VK v1.0 | 13 | | |
| hu07 VH v1.1 | 37 | T28S, F29L, A49G, F67L, N76S | hu07 VK v1.1 | 42 | K41S, A42S, D70S | |
| hu07 VH v1.2 | 38 | R71K | hu07 VK v1.2 | 43 | L47W | |
| hu07 VH v1.3 | 39 | T28S, F29S, R71K | hu07 VK v1.3 | 44 | F71Y | |
| hu07 VH v1.4 | 40 | T28S, F29S, | hu07 VK v1.4 | 45 | L47W, F71Y | |
| hu07 VH v1.5 | 41 | T28S, F29S, A49G, R71K | hu07 VK v1.5 | 46 | K41S, A42S, D70S, L47W | |
| | | | hu07 VK v1.6 | 47 | K41S, A42S, D70S, F71Y | |
| | | | hu07 VK v1.7 | 48 | K41S, A42S, D70S, L47W, F71Y | |

Example 9

Characterization of Humanized hu07

To evaluate the binding/competition properties of the various versions of hu0, transient transfections with 19 combinations of hu07 heavy and light chains were performed in COS-1 M6 cells. 6 heavy chains and 3 light chains were included: chimeric heavy chain, humanized v1.0-1.5 heavy chain, chimeric light chain and humanized v1.0-1.1 light chain. Conditioned media (CM) was harvested 2 days after transfection and subjected for direct binding to recombinant IL-13-Rα2 by standard ELISA, cell surface receptor binding by cell-based ELISA using A375 cells, and competition ELISA with biotinylated ch07, utilizing protocols known in the art.

Based on initial screening data from CM, heavy chain v1.5 was selected for further study. Heavy chain v1.5 was paired with chimeric, humanized v1.0 and v1.1 light chain. Table 11 summarizes the binding activity, competition properties and cytoxicity of hu07 antibodies. hu07 v1.5 paired with chimeric light chain Kc demonstrates a similar ED50 and IC50 to the chimeric antibody. The competition activity on the A375 cells and recombinant protein were decreased when this heavy chain v1.5 was paired with light chain v1.0 and v1.1.

TABLE 11

|  | IC50 (nM) Competition ELISA Plate | ED50 (nM) ELISA rhIL-13Rα2 | ED50 (nM) cELISA A375 cells | IC50 (nM) Competition ELISA A375 cells | IC50 (nM) Saporin Assay A375 cells |
|---|---|---|---|---|---|
| ch07 | 2.21 | 0.217 | 0.85 | 17.27 | 0.08 |
| hu07v1.5/kc | 3.03 | 0.183 | 0.87 | 7.67 | ND |
| hu07v1.5/v1.0 | 62.00 | 0.754 | 1.17 | 12.27 | 0.19 |
| hu07v1.5/v1.1 | 46.62 | 1.214 | 1.29 | 19.00 | 0.20 | hu07 heavy chain v1.5 was used for light chain optimization. Transient transfections with 10 combinations of hu07 heavy and light chains were performed in COS-1 M6 cells. The heavy chain v1.5 was paired with chimeric light chain and humanized versions v1.0-1.7. CM was harvested and used in experiments to determine binding affinity to recombinant hIL-13α2 (rhIL-13α2) by ELISA and competition activity to biotinylated ch07 by competition ELISA. The data indicates that the combination of heavy chain v1.5 and light chain v1.7 is optimal. This result was confirmed with purified protein (Table 12).

TABLE 12

|  | ED50 (nM) rhIL-13Rα2 | IC50 (nM) Competition ELISA Plate |
|---|---|---|
| ch07 | 0.39 | 2.21 |
| hu07Hv1.5/kv1.7 | 0.39 | 7.7 |

Example 10

Species Cross Reactivity of ch07, hu07, ch08 and hu08

Cynomolgous (cyno) monkey IL-13-Rα2 (extracellular domain (ECD)) and Transmembrane Domain™ were isolated from cyno monkey testis and adipose tissues by RT-PCR. The amino acid sequence of cyno IL-13-Rα2 is shown in SEQ ID NO: 27. The identity is 94% between human and cyno IL-13Rα2.

The ECD/TM domain of cyno IL-13-Rα2 fused with Flag tag at the C-terminal end was cloned into the pSMED2 expression vector. HEK293 suspension cells were transiently transfected with cyno-IL-13-Rα2 containing plasmid and pSMED2 vector (as a mock transfection). The cells were harvested 72 hours later and subjected to FACS analysis. 4 antibodies including ch07, ch08, hu08v1.0/1.0 and hu08v1.1/1.1 were tested. The binding on the cell surface cyno-IL-13-Rα2 was detected with R-Phycoerythrin-labeled goat anti-human or mouse IgG. The data demonstrates that ch07, ch08, hu08v1.0/1.0 and hu08v1.1/1.1 are able to bind to the cell surface cyno-IL-13-Rα2 and have similar binding affinities (ED50) (Table 13).

TABLE 13

| Antibody | ED50 (nM) |
|---|---|
| ch07 | 1.494 |
| ch08 | 1.814 |
| hu08v1.0/1.0 | 1.961 |
| hu08v1.1/1.1 | 2.141 |

The binding of hu07 and hu08 to mouse IL-13-Rα2 was evaluated by direct ELISA. The identity between human and mouse IL-13-Rα2 at the amino acid level is approximately 64%. Recombinant mIL-13-Rα2 or hIL-13-Rα2 (as positive control) was coated onto a 96-well plate. Purified chimeric ch07 and ch08 were serially diluted and added to the antigen coated plate. The bound antibodies were detected by HRP conjugated goat anti-human IgGFc specific secondary antibody. There was no detectable signal for mIL-13-Rα2 binding while the binding to the positive control hIL-13-Rα2 was strong, indicating that hu07 and hu08 do not cross-react to murine mIL-13Rα2.

Example 11

Binding to Human Cell Lines Expressing IL13R-α2

Cell lines expressing the IL-13-Rα2 antigen and the negative control cells were plated at a density of 200,000 cells per well of 96 deep well plates and kept on ice. The mouse monoclonal antibodies mu07 or mu08 prepared in 3% bovine serum albumin BSA in Dulbecco's phosphate buffered saline (DPBS) were added to the plate at a final concentration of 10 μg/mL. The plates were then incubated on ice for 1 hour followed by 2 washes. The secondary antibody, PE (phycoerythrin) conjugated goat anti-mouse IgG Fc was added to the wells. After 30 minutes of incubation at 4° C., the mean fluorescence intensity was then analyzed by FACS on a FACScan™ (BD Biosciences).

The data in Table 14 indicates that the mu07 and mu08 antibodies bind to a diverse panel of IL-13R-α2 positive cell lines from various disease indications.

TABLE 14

|  | Mean Fluorescent Intensity | | IL-13-Rα2 |
|---|---|---|---|
| Human Cell Line | mu07 | mu08 | Expression |
| PC3MM2 (prostate) | 84000 | 72000 | 3+ |
| U87MG (glioblastoma) | 61000 | 62000 | 3+ |
| A375 (melanoma) | 53000 | 46000 | 3+ |
| H460 (lung, cisplatin resistant) | 28000 | 22000 | 2+ |
| Hs766T (pancreatic) | 13000 | 14000 | 2+ |
| A498 (renal) | 13000 | 5000 | 1+ |
| SW626 (ovarian) | 9000 | 8000 | 1+ |
| H460 (lung) | 800 | 300 | 0 |

Example 12

Internalization

Antibody internalization is a critical characteristic for delivering ADCs for cytotoxicity in IL-13-Rα2 expressing cells. Internalization of the antibody after binding to IL-13-Rα2 was examined using mu07 and mu08 antibodies and a positive control mouse monoclonal antibody (ab27414), on four cell lines (PC3MM2, A375, Hs766T, and H460R). The antibodies (10 μg/mL) were incubated with the various cells for 1 hour on ice and unbound antibody was removed by washing twice with cold media. The cell culture plates were incubated at 37° C. Samples of the cells were fixed at 15 minutes and at 4 hours. The percent internalization at different timepoints is shown in Table 15. The data show that mu07 and mu08 are readily internalized into IL-13-Rα2 expressing cells.

TABLE 15

| | % internalization | | | | | | | |
|---|---|---|---|---|---|---|---|---|
| | 15 min | | | | 4 hours | | | |
| Primary Abs | A375 | Hs766T | PC3MM2 | H460R | A375 | Hs766T | PC3MM2 | H460R |
| mu07 | 63.1 | 69.6 | 88.6 | 74.4 | 38.1 | 69.0 | 50.3 | 38.4 |
| mu08 | 68.0 | 64.1 | 81.9 | 55.9 | 61.8 | 76.3 | 41.6 | 47.4 |
| ab27414 | 49.3 | 60.8 | 60.2 | 57.5 | 68.2 | 73.6 | 49.7 | 49.2 |

Example 13

Synthesis of Compounds 0101 and 3377

Compounds 0101 and 3377 were prepared according to the methods described in U.S. patent application Ser. No. 13/670,612, herein incorporated by reference.

Experimental for Compound 0101 (#54 in the Schematic)

Preparation of 2-Methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#54)

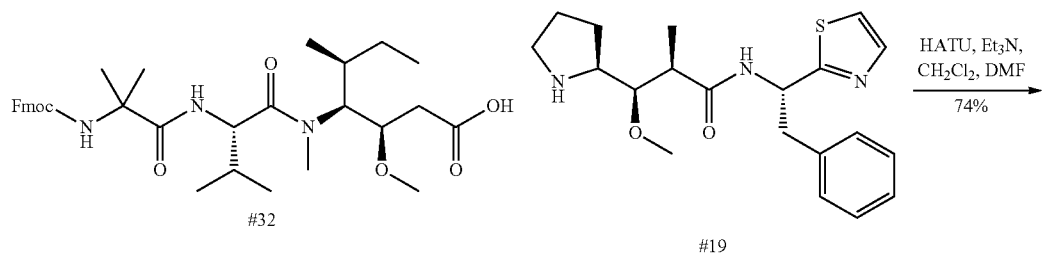

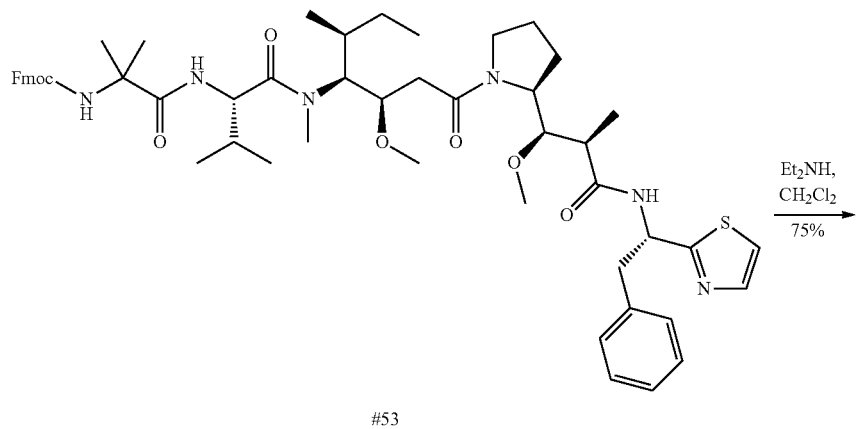

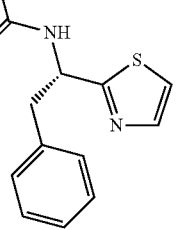

54

Step 1. Synthesis of N-[(9H-fluoren-9-ylmethoxy)carbonyl]-2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#53). According to general procedure D, from #32 (2.05 g, 2.83 mmol, 1 eq.) in dichloromethane (20 mL, 0.1 M) and N,N-dimethylformamide (3 mL), the amine #19 (2.5 g, 3.4 mmol, 1.2 eq.), HATU (1.29 g, 3.38 mmol, 1.2 eq.) and triethylamine (1.57 mL, 11.3 mmol, 4 eq.) was synthesized the crude desired material, which was purified by silica gel chromatography (Gradient: 0% to 55% acetone in heptane), producing #53 (2.42 g, 74%) as a solid. LC-MS: m/z 965.7 [M+H$^+$], 987.6 [M+Na$^+$], retention time=1.04 minutes; HPLC (Protocol A): m/z 965.4 [M+H$^+$], retention time=11.344 minutes (purity >97%); $^1$H NMR (400 MHz, DMSO-d$_6$), presumed to be a mixture of rotamers, characteristic signals: δ 7.86-7.91 (m, 2H), [7.77 (d, J=3.3 Hz) and 7.79 (d, J=3.2 Hz), total 1H], 7.67-7.74 (m, 2H), [7.63 (d, J=3.2 Hz) and 7.65 (d, J=3.2 Hz), total 1H], 7.38-7.44 (m, 2H), 7.30-7.36 (m, 2H), 7.11-7.30 (m, 5H), [5.39 (ddd, J=11.4, 8.4, 4.1 Hz) and 5.52 (ddd, J=11.7, 8.8, 4.2 Hz), total 1H], [4.49 (dd, J=8.6, 7.6 Hz) and 4.59 (dd, J=8.6, 6.8 Hz), total 1H], 3.13, 3.17, 3.18 and 3.24 (4s, total 6H), 2.90 and 3.00 (2 br s, total 3H), 1.31 and 1.36 (2 br s, total 6H), [1.05 (d, J=6.7 Hz) and 1.09 (d, J=6.7 Hz), total 3H].

Step 2. Synthesis of 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#54) According to general procedure A, from #53 (701 mg, 0.726 mmol) in dichloromethane (10 mL, 0.07 M) was synthesized the crude desired material, which was purified by silica gel chromatography (Gradient: 0% to 10% methanol in dichloromethane). The residue was diluted with diethyl ether and heptane and was concentrated in vacuo to afford #54 (406 mg, 75%) as a white solid. LC-MS: m/z 743.6 [M+H$^+$], retention time=0.70 minutes; HPLC (Protocol A): m/z 743.4 [M+H$^+$], retention time=6.903 minutes, (purity >97%); $^1$H NMR (400 MHz, DMSO-d$_6$), presumed to be a mixture of rotamers, characteristic signals: δ [8.64 (br d, J=8.5 Hz) and 8.86 (br d, J=8.7 Hz), total 1H], [8.04 (br d, J=9.3 Hz) and 8.08 (br d, J=9.3 Hz), total 1H], [7.77 (d, J=3.3 Hz) and 7.80 (d, J=3.2 Hz), total 1H], [7.63 (d, J=3.3 Hz) and 7.66 (d, J=3.2 Hz), total 1H], 7.13-7.31 (m, 5H), [5.39 (ddd, J=11, 8.5, 4 Hz) and 5.53 (ddd, J=12, 9, 4 Hz), total 1H], [4.49 (dd, J=9, 8 Hz) and 4.60 (dd, J=9, 7 Hz), total 1H], 3.16, 3.20, 3.21 and 3.25 (4s, total 6H), 2.93 and 3.02 (2 br s, total 3H), 1.21 (s, 3H), 1.13 and 1.13 (2 s, total 3H), [1.05 (d, J=6.7 Hz) and 1.10 (d, J=6.7 Hz), total 3H], 0.73-0.80 (m, 3H).

Experimental for Compound 3377 (#115 in the Schematic)

Preparation of N,2-dimethylalanyl-N-{(1S,2R)-4-{(2S)-2-[(1R,2R)-3-{[(1S)-1-carboxy-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide, trifluoroacetic acid salt (#115).

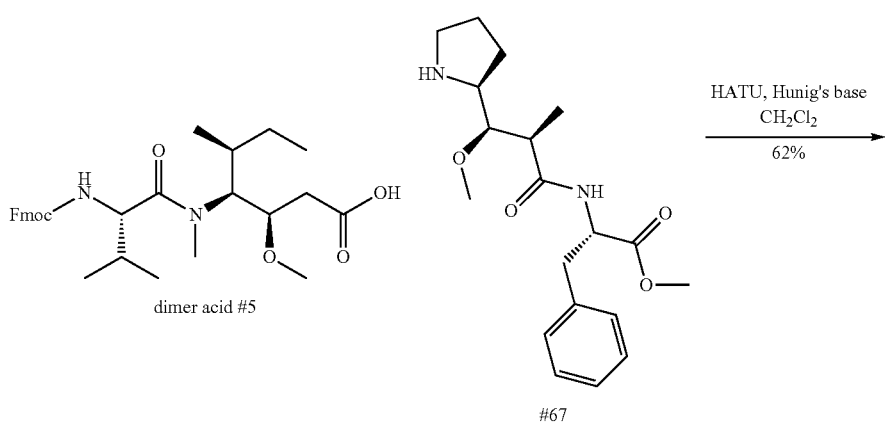

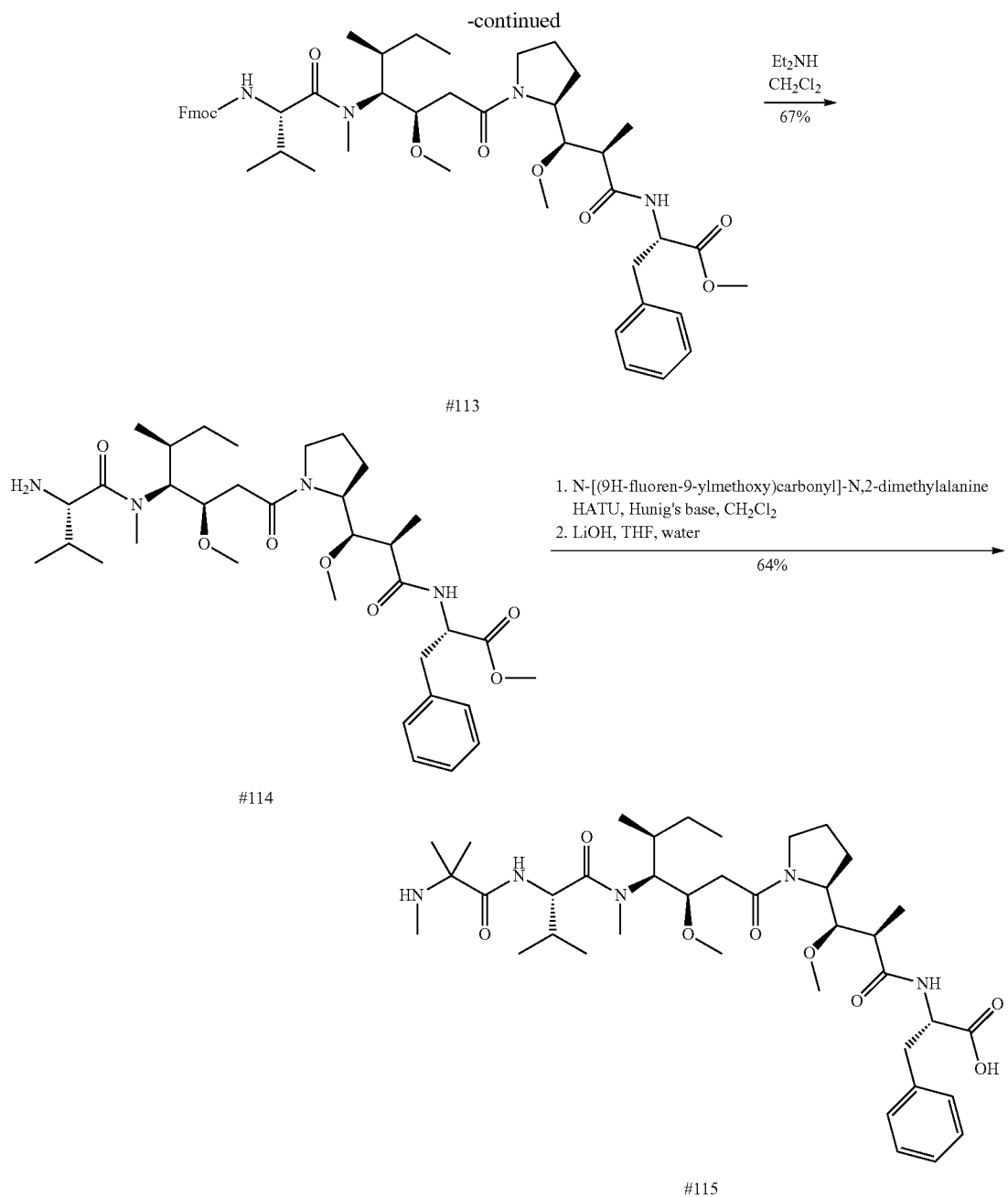

Step 1. Synthesis of methyl N-{(2R,3R)-3-[(2S)-1-{(3R,4S,5S)-4-[{N-[(9H-fluoren-9-ylmethoxy)carbonyl]-L-valyl}(methyl)amino]-3-methoxy-5-methylheptanoyl}pyrrolidin-2-yl]-3-methoxy-2-methylpropanoyl}-L-phenylalaninate (#113). To a stirring mixture of dimer acid #5 (12. 1 g, 23.0 mM) and #67 (11.5 g, 23.0 mM) in 75 mL of dichloromethane under nitrogen, HATU (10.8 g, 27.6 mM) was added followed by Hunig's base (12.1 mL, 69.0 mM). The reaction was allowed to stir at room temperature for 15 hours. Reaction was concentrated to a smaller volume, taken up with ethyl acetate and washed with 1 N HCl two times. The organic layer was then washed with brine, dried over sodium sulfate, filtered, and concentrated in vacuo. Residue was then purified by silica gel chromatography (Gradient: 0% to 70% acetone in heptanes), producing #113 (12.3 g, 62%) as a white solid. LC-MS (Protocol Q): m/z 855.3 [M+H$^+$], 877.2 [M+Na$^+$], retention time=2.32 minutes; HPLC (Protocol R): m/z 855.5 [M+H$^+$], retention time=9.596 minutes (purity >97%).

Step 2. Synthesis of methyl N-{(2R,3R)-3-methoxy-3-[(2S)-1-{(3R,4S,5S)-3-methoxy-5-methyl-4-[methyl(L-valyl)amino]heptanoyl}pyrrolidin-2-yl]-2-methylpropanoyl}-L-phenylalaninate (#114). According to general procedure A, from #113 (12 g, 14 mmol, 1 eq.), dichloromethane (60 mL, 0.24 M) and diethylamine (40 mL, 390 mM) was synthesized #114 (5.9 g, 67%) white/slight yellow solid after purification by silica gel chromatography (Gradient: 0% to 25% methanol in dichloromethane). LC-MS (Protocal Q): m/z 633.0 [M+H$^+$], retention time=1.19 minutes. HPLC (Protocol A): m/z 633.5 [M+H$^+$], retention time=7.142 minutes (purity >98%).

Step 3. Synthesis of N,2-dimethylalanyl-N-{(1S,2R)-4-{(2S)-2-[(1R,2R)-3-{[(1S)-1-carboxy-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide-trifluoroacetic acid salt (#115). To a stirring mixture of N-[(9H-fluoren-9-ylmethoxy)carbonyl]-N,2-dimethylalanine (167 mg, 0.493 mM), #114 (260 mg, 0.411 mM), and HATU (188 mg, 0.493 mM) in 10 mL of dichloromethane, Hunig's base (0.14 mL, 0.82 mM) was added. The reaction was allowed to stir at room temperature for 1 hour and 20 minutes. Reaction was reduced down. THF (9 mL) was added to crude material and to this stirring mixture lithium hydroxide (49.2 mg, 2.06 mM) dissolved in 3 mL of water was added. The reaction was allowed to stir at room temperature for 4 hours. Reaction was concentrated down followed by purification by medium pressure reverse phase C18 chromatography (Gradient: 5% to 45% water in acetonitrile with 0.02% TFA in each phase) #115 (218 mg, 64%) white solid. LC-MS (Protocol Q): m/z 718.7 [M+H$^+$], 740.6 [M+Na$^+$], retention time=1.21 minutes. HPLC (Protocol A at 45° C.): m/z 718.4 [M+H$^+$], retention time=6.903 minutes.

Example 14

Preparation of Anti-IL-13-Rα2 ADCs

The ADCs of the present invention can be prepared using a section of the linker having a reactive site for binding to a chemical compound and introducing another section of the linker having a reactive site for an antibody. In one aspect, a linker has a reactive site which has an electrophilic group that is reactive with a nucleophilic group present on an antibody unit, such as an antibody. Useful nucleophilic groups on an antibody include but are not limited to, sulfhydryl, hydroxyl and amino groups. The heteroatom of the nucleophilic group of an antibody is reactive to an electrophilic group on a linker and forms a covalent bond to a linker. Useful electrophilic groups include, but are not limited to, maleimide and haloacetamide groups.

A linker has a reactive site which has a nucleophilic group that is reactive with an electrophilic group present on an antibody unit. The electrophilic group on an antibody provides a convenient site for attachment to a linker. Useful electrophilic groups on an antibody include, but are not limited to, aldehyde and ketone carbonyl groups. The heteroatom of a nucleophilic group of a linker can react with an electrophilic group on an antibody and form a covalent bond to the antibody. Useful nucleophilic groups on a linker include, but are not limited to, hydrazide, oxime, amino, hydrazine, thiosemicarbazone, hydrazine carboxylate, and arylhydrazide.

As used herein, "mc-" refers to:

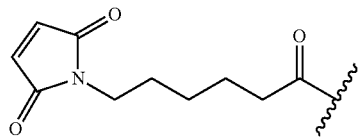 [SMILES: *C(=O)CCCCCN1C(=O)C=CC1=O]

As used herein, "vc-" refers to:

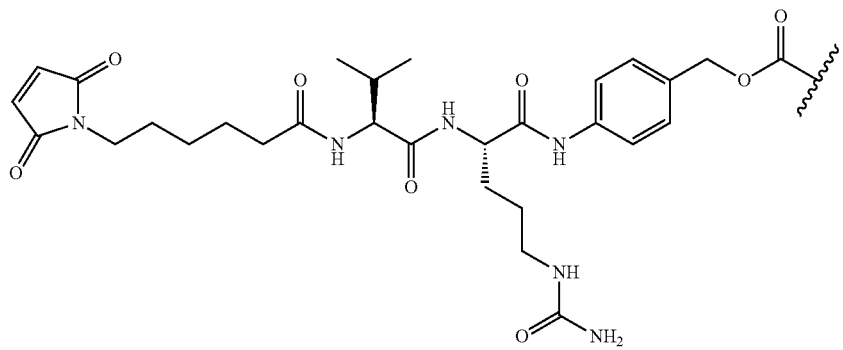 [SMILES: *C(=O)OCc1ccc(NC(=O)[C@H](CCCNC(N)=O)NC(=O)[C@@H](NC(=O)CCCCCN2C(=O)C=CC2=O)C(C)C)cc1]

The anti-IL-13-Rα2 ADCs were prepared via partial reduction of the mAb with tris(2-carboxyethyl)phosphine (TCEP) followed by reaction of reduced cysteine residues with the desired maleimide terminated linker-payload. In particular, hu08 was partially reduced via addition of 2.2 molar excess of tris(2-carboxyethyl)phosphine (TCEP) in 100 mM HEPES (4-(2-hydroxyethyl)-1-piperazineethanesulfonic add buffer), pH 7.0 and 1 mM diethylenetriaminepentaacetic acid (DTPA) for 2 h at 37° C. The desired linker-payload was then added to the reaction mixture at a linker-payload/mAb molar ratio of 7.0 maleimidocapronic-valine-citruline-p-aminobenzyloxycarbonyl-aurstatin-0101 [vc-0101, see below]), or 7.0 maleimidocapronic-auristatin-3377 [mc-3377, see below] and reacted for an additional 1 h at 25° C. in the presence of 15% v/v of dimethylacetamide (DMA). After the 1 h incubation period, N-ethylmaleimide (3 fold excess for vc-0101 and for mc-3377) was added to cap the unreacted thiols and is allowed to react for 15 minutes, followed by addition of 6 fold excess L-Cys to quench any unreacted linker-payload. The reaction mixture was dialyzed overnight at 4° C. in phosphate buffered saline (PBS), pH 7.4, and purified via SEC (AKTA explorer, Superdex 200 10/30 GL column). The ADC was further characterized via size exclusion chromatography (SEC) for purity, hydrophobic interaction chromatography (HIC), and liquid chromatography electrospray ionization tandem mass spectrometry (LC-ESI MS) to calculate drug-antibody ratio (loading). The protein concentration was determined via UV spectrophotometer.

mc-3377 (conjugation to antibody X through a cysteine residue)

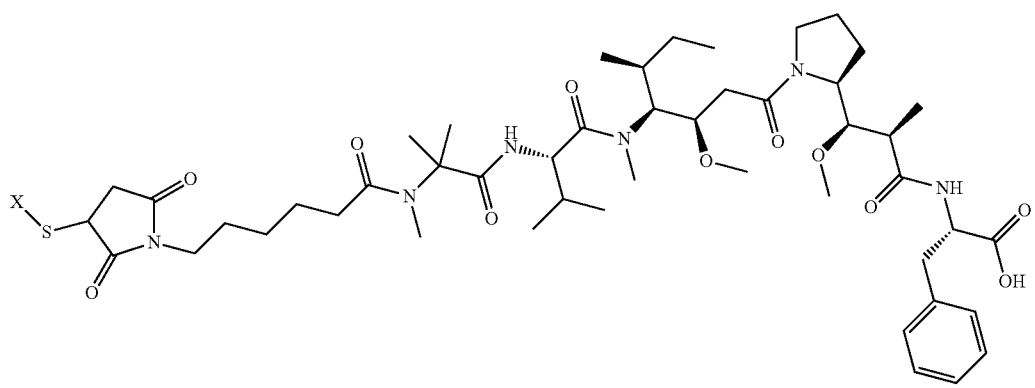

vc-0101 (conjugation to antibody X through a cysteine residue)

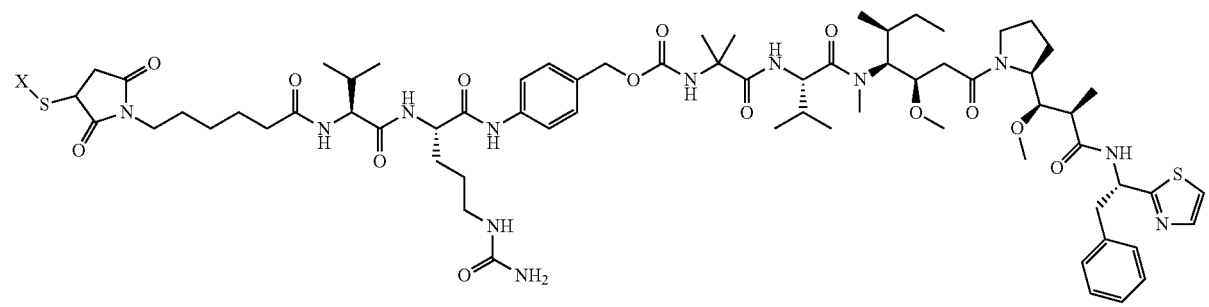

Example 15

In Vitro Cytotoxicity Assay

Cell lines expressing the IL-13-Rα2 antigen and a negative control cell line, were cultured with increasing concentrations of anti-IL-13-Rα2 ADC. After four days, viability of each culture is assessed. $IC_{50}$ values were calculated by logistic non-linear regression and are presented as ng Ab/mL. The preferred linker payloads were vc-0101 and mc-3377.

Humanized anti-IL-13Rα2 antibody hu08 was conjugated to various linker-payload combinations as provided in Table 16. The antibody drug conjugates were prepared according to the methods described in U.S. patent application Ser. No. 13/670,612, now U.S. Pat. No. 8,828,401, which is incorporated herein by reference, with the corresponding nomenclature and experimental chemical synthesis schematic number indicated in Table 16.

TABLE 16

| ADC Linker-Payload | Corresponding ADC Linker-Payload # |
| --- | --- |
| hu08-vc-0101 | IL13Rα2-AB08-v1010-hG1-(C)_mcValCitPABC-#54 |
| hu08-mc-3377 | IL13Rα2-AB08-v1010-hG1-(C)_mc-#115 |
| hu08-mc-0131 | IL13Rα2-AB08-v1010-hG1-(C)_mc-0#118 |

TABLE 16-continued

| ADC Linker-Payload | Corresponding ADC Linker-Payload # |
| --- | --- |
| hu08-Malpeg-6121 | IL13Rα2-AB08-v1010-hG1-(C)_MalPeg6C2-#117 |
| hu08-Malpeg-0131 | IL13Rα2-AB08-v1010-hG1-(C)_Mal(H2O)Peg6C2-0#118 |
| hu08-mc-6121 | IL13Rα2-AB08-v1010-hG1-(C)_mc-#117 |
| hu08-vc-3906 | IL13Rα2-AB08-v1010-hG1-(C)_mcValCitPABC-#226 |
| hu08-vc-6780 | IL13Rα2-AB08-v1010-hG1-(C)_mcValCitPABC-#112 |
| hu08-mc-8261 | IL13Rα2-AB08-v1010-hG1-(C)_mc-#69 |
| hu08-mc-3906 | IL13Rα2-AB08-v1010-hG1-(C)_mc-#226 |
| hu08-MalPeg-8261 | IL13Rα2-AB08-v1010-hG1-(C)_MalPeg6C2-#69 |
| huIgG8.8-vc-0101 | huIgG8.84-mcValCitPABC-#54 |
| huIgG8.8-mc-3377 | huIgG8.84-mc-#115 |

Further, a mutant version of hu08 (hu08MAC) was generated as described in Example 21 and according to standard protocols. Compound 0101 was conjugated to a cleavable linker to form the structure:

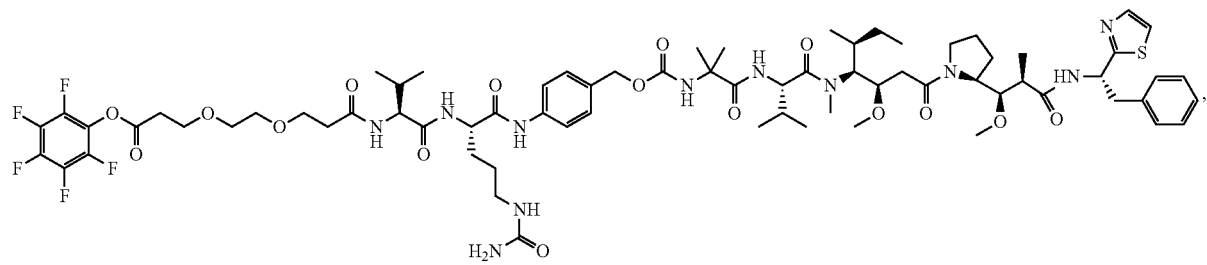 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)C(C)(C)NC(=O)OCc1ccc(NC(=O)[C@H](CCCNC(N)=O)NC(=O)[C@@H](NC(=O)CCOCCOCCC(=O)Oc2c(F)c(F)c(F)c(F)c2F)C(C)C)cc1)C(C)C]

and thereafter conjugated to hu08MAC according to the techniques described herein to form hu08MAC-0101.

The data demonstrates that the anti-IL-13-Rα2 antibody hu08v1.0/1.0 conjugated to six different auristatin payloads was effective against both of the IL-13-Rα2 positive cell lines tested (PC3MM2 and A375), having an $IC_{50}$ ranging from 1.1 to 4.9 ng Ab/mL or 7.3-32.7 pM) (Table 17). Further, hu08MAC-0101 was effective against both of the IL-13Rα2 positive cell lines tested (PC3MM2 and A375), having an $IC_{50}$ of 7.9 ng Ab/mL. All ADCs were not active against the IL-13-Rα2 negative cell line, H460, and the non-IL-13-Rα2 binding control ADCs, hIgG8.8-vc-0101 and hIgG8.8-mc-3377, were not active against any of the cell lines tested.

TABLE 17

| ADC | DAR | $IC_{50}$ (ng Ab/mL) | | |
|---|---|---|---|---|
| | | PC3MM2 | A375 | H460 |
| hu08-vc-0101 | 3.2 | 2.5 | 3.8 | >400000 |
| hu08-mc-3377 | 4.3 | 1.2 | 2.2 | >400000 |
| hu08-mc-0131 | 3.2 | 1.3 | 2.1 | >400000 |
| hu08-MalPeg-6121 | 3.3 | 3.5 | 3.4 | >400000 |
| hu08-MalPeg-0131 | 2.9 | 2.9 | 4.9 | >400000 |
| hu08-mc-6121 | 3.3 | 1.1 | 2.4 | >400000 |
| hu08-mc-3906 | 3 | 1.5 | 2.9 | >400000 |
| hu08 vc-6780 | 4 | 1.2 | 2.2 | >400000 |
| hu08MAC-0101 | 1.9 | 4.9 | 7.9 | >400000 |
| hIgG8.8-vc-0101 | 3.7 | >400000 | >400000 | >400000 |
| hIgG8.8-mc-3377 | 4.3 | >400000 | >400000 | >400000 |

Example 16

Subcutaneous Xenograft Models

Female, athymic (nude) mice were injected s.c. with PC3MM2 or A375 tumor cells. Mice with staged tumors, approximately 0.2 to 0.8 g (n=8 to 10 mice/treatment group), were administered intravenously q4d×4 with normal saline (vehicle), hu08v1.0/1.0 ADCs with linker-payloads vc-0101, vc-6780, vc-3906, mc-8261, mc-0131, mc-6121, mc-3377, MalPeg-8261, MalPeg-0131, MalPeg-6121, and MalPeg-3906, and a non-binding Ab (hIgG8.8) conjugated with vc-0101 or mc-3377, at a dose of 2 or 3 mg Ab/kg. The ADCs were dosed based on Ab content. Tumors were measured at least once a week and their size is calculated as $mm^3=0.5\times(tumor\ width^2)\times(tumor\ length)$.

The in vivo efficacy results listed in Table 18 show a range of anti-tumor activity with the various ADCs tested. The relative order of potency is hu08-vc-0101>hu08-vc-6780 hu08-mc-0131>hu08-mc-6121>hu08-mc-3906>hu08-MalPeg-0131>hu08-MalPeg-6121>hu08-MalPeg-3906>hu08-mc-8261.

The data in Table 19 indicates that ADCs hu08-vc-0101 and hu08-mc-3377 were efficacious 3 mg/kg in reducing tumor growth in the PC3MM2. Compared to the vehicle control group which was terminated at Day 15 due to large size of tumors (>2500 mm³ from some of animals), hu08-vc-0101 and hu07-mc-3377 have 5 out of 8 or 3 out of 8 animals without measurable tumors at Day 76, respectively. Similar to the vehicle control group, irrelevant ADC control groups of hIgG8.8-vc-0101 at 3 mg/kg and hIgG8.4-mc-3377 at 10 mg/kg was terminated at Day 15 and Day 19 respectively due to the large size of tumors in the groups, respectively. These results demonstrate that the significant therapeutic efficacy (some animals were cured of disease) from hu08-vc-0101 and hu07-mc-3377 was IL-13-Rα2 target-mediated.

TABLE 18

| ADC | Dose (mg/kg) Q4dx4 | PC3MM2 xenograft, tumor volume (mm³ +/− SEM) | | | | | | | |
|---|---|---|---|---|---|---|---|---|---|
| | | Day −1 | Day 3 | Day 8 | Day 16 | Day 20 | Day 30 | Day 42 | Day 52 |
| Vehicle | 0 | 638 ± 27 | 1149 ± 82 | 1707 ± 133 | GT | GT | GT | GT | GT |
| hu08-Malpeg-3906 | 2 | 642 ± 36 | 1036 ± 60 | 1176 ± 51 | GT | GT | GT | GT | GT |
| hu08-mc-8261 | 2 | 642 ± 51 | 1088 ± 121 | 1429 ± 158 | GT | GT | GT | GT | GT |
| hu08-mc-0131 | 2 | 637 ± 44 | 1004 ± 73 | 778 ± 83 | GT | GT | GT | GT | GT |
| hu08-Malpeg-6121 | 2 | 638 ± 36 | 947 ± 85 | 1000 ± 126 | 693 ± 129 | 780 ± 198 | GT | GT | GT |

TABLE 18-continued

| ADC | Dose (mg/kg) Q4dx4 | PC3MM2 xenograft, tumor volume (mm³ +/− SEM) | | | | | | |
|---|---|---|---|---|---|---|---|---|
| | | Day −1 | Day 3 | Day 8 | Day 16 | Day 20 | Day 30 | Day 42 | Day 52 |
| hu08-Malpeg-0131 | 2 | 649 ± 39 | 1085 ± 54 | 1040 ± 88 | GT | GT | GT | GT | GT |
| hu08-vc-0101 | 2 | 646 ± 36 | 899 ± 54 | 557 ± 49 | 243 ± 28 | 201 ± 20 | 113 ± 17 | 207 ± 49 | 532 ± 151 |
| hu08-vc-6780 | 2 | 641 ± 28 | 850 ± 100 | 652 ± 54 | 279 ± 55 | 217 ± 45 | 230 ± 133 | GT | GT |
| hu08-mc-6121 | 2 | 636 ± 37 | 909 ± 63 | 821 ± 93 | 441 ± 83 | 414 ± 104 | GT | GT | GT |
| hu08-mc-3906 | 2 | 637 ± 26 | 875 ± 48 | 806 ± 70 | 611 ± 150 | GT | GT | GT | GT |
| hu08-Malpeg-8261 | 2 | 645 ± 34 | 991 ± 71 | 1220 ± 115 | GT | GT | GT | GT | GT |

GT = group terminated due to large tumor size

TABLE 19

| ADC | Dose (mg/kg) Q4dx4 | PC3MM2 xenograft, tumor volume(mm³ +/− SEM) | | | | | | |
|---|---|---|---|---|---|---|---|---|
| | | Day −1 | Day 2 | Day 10 | Day 19 | Day 40 | Day 51 | Day 61 | Day 71 |
| vehicle | 0 | 340 ± 16 | 573 ± 47 | 1441 ± 176 | 1975 ± 272 | GT | GT | GT | GT |
| hIgG8.84-mc-3377 | 10 | 328 ± 27 | 459 ± 63 | 295 ± 121 | 544 ± 258 | GT | GT | GT | GT |
| hu08-mc-3377 | 3 | 337 ± 21 | 385 ± 36 | 41 ± 12 | 0 ± 0 | 78 ± 36 | 346 ± 147 | 616 ± 243 | 902 ± 364 |
| hu08-vc-0101 | 3 | 339 ± 18 | 433 ± 45 | 38 ± 14 | 6 ± 6 | 110 ± 110 | 230 ± 230 | GT | GT |
| hIgG8.8-vc-0101 | 3 | 333 ± 23 | 449 ± 15 | 686 ± 134 | GT | GT | GT | GT | GT |

GT = group terminated due to large tumor size.

The data in Table 20a indicates that ADCs of hu08-vc-0101 and hu08-mc-3377 were efficacious at 3 mg/kg in a second in vivo xenograft model using A375 cells. The vehicle control group and irrelevant ADC control groups of hIgG8.8-vc-0101 and hIgG8.8-mc-3377 were terminated due to large tumor size at Day 19, 22, 27, respectively. Treatment with hu08-vc-0101 and hu08-mc-3377 at 3 mg/kg caused tumor regression in all animals and provided significant survival advantage. No measureable tumor was observed in all animals treated with hu08-mc-3377 at Day 19-22. Although some tumors relapsed, there were 5 out of 10 animals without measurable tumors at Day 71. The group treated with hu08-vc-0101 was monitored over 100 days and 8 of animals had no measurable tumors at Day 19-100. These results demonstrate potent antitumor activities of hu08-vc-0101 and hu08-mc-3377 against IL-13-Rα2 positive tumors.

TABLE 20a

| ADC | Dose (mg/kg) Q4dx4 | A375 Xenograft Tumor Volume (mm³ ± SEM) | | | | | | |
|---|---|---|---|---|---|---|---|---|
| | | Day −1 | Day 2 | Day 13 | Day 19 | Day 40 | Day 51 | Day 61 | Day 71 |
| Vehicle | 0 | 340 ± 16 | 573 ± 47 | 1441 ± 176 | 1975 ± 272 | GT | GT | GT | GT |
| hIgG8.8-mc-3377 | 3 | 328 ± 27 | 459 ± 63 | 295 ± 121 | 544 ± 258 | GT | GT | GT | GT |
| Hu08-mc-3377 | 3 | 337 ± 21 | 385 ± 36 | 41 ± 14 | 0 ± 0 | 78 ± 36 | 346 ± 147 | 616 ± 243 | 902 ± 364 |
| Hu08-vc-0101 | 3 | 336 ± 19 | 407 ± 42 | 43 ± 15 | 7 ± 15 | 122 ± 7 | 256 ± 122 | 0 ± 0 | 0 ± 0 |
| hIgG8.8-vc-0101 | 3 | 333 ± 23 | 449 ± 15 | 686 ± 135 | 1145 ± 212 | GT | GT | GT | GT |

GT = group terminated due to large tumor size.

The data in Tables 20b and 20c indicates that ADCs hu08-vc-0101 and hu08-mc3377 were efficacious in a third in vivo xenograft model using the HEY-C2 ovarian cancer cell line. The vehicle control group and negative ADC control group's hIgG8.8-vc0101 (3 mg/kg and 10 mg/kg) and hIgG8.8-mc-3377 (10 mg/kg) were terminated due to large tumor size as indicated with the GT designation. Treatment with hu08-vc-0101 and hu08-mc-3377 at dose levels of 1, 3 and 10 mg/kg, provided a dose-dependent response. Five out of nine animals treated with 3 mg/kg of hu08-vc-0101 and seven out of nine animals treated with 10 mg/kg of hu08-vc-0101 survived to end of the study (Day 103). Similarly, five out of nine animals treated with 3 mg/kg of hu08-mc-3377 and nine out of nine animals treated with 10 mg/kg of hu08-mc-3377 survived to the end of the study (Day 103).

TABLE 20b

| ADC | Dose (mPk) Q4d | HEY-C2 Xenograft, tumor volume (mm³ ± SEM) | | | | | | | | | |
|---|---|---|---|---|---|---|---|---|---|---|---|
| | | Day −1 | Day 3 | Day 12 | Day 23 | Day 30 | Day 40 | Day 51 | Day 60 | Day 72 | Day 79 | Day 95 | Day 103 |
| vehicle | 0 | 211 ± 16 | 375 ± 21 | 919 ± 53 | 2311 ± 156 | GT | GT | GT | GT | GT | GT | GT | GT |
| hAB08 mc_3377 | 1 | 211 ± 17 | 324 ± 23 | 337 ± 25 | 510 ± 128 | 665 ± 203 | GT | GT | GT | GT | GT | GT | GT |
| | 3 | 211 ± 17 | 319 ± 38 | 250 ± 37 | 207 ± 41 | 239 ± 64 | 336 ± 131 | 602 ± 258 | GT | GT | GT | GT | GT |
| | 10 | 211 ± 16 | 303 ± 28 | 181 ± 17 | 114 ± 10 | 106 ± 7 | 84 ± 16 | 69 ± 14 | 53 ± 14 | 42 ± 11 | 41 ± 12 | 121 ± 59 | 308 ± 166 |
| hIgG 8.8 mc_3377 | 10 | 212 ± 18 | 375 ± 46 | 557 ± 53 | 650 ± 183 | GT | GT | GT | GT | GT | GT | GT | GT |

TABLE 20c

| ADC | Dose (mpk) Q4d | HEY-C2 Xenograft, tumor volume (mm³ ± SEM) | | | | | | | | | |
|---|---|---|---|---|---|---|---|---|---|---|---|
| | | Day −1 | Day 3 | Day 12 | Day 23 | Day 30 | Day 40 | Day 51 | Day 60 | Day 72 | Day 79 | Day 95 | Day 103 |
| hAB08 vc_0101 | 1 | 211 ± 16 | 335 ± 27 | 331 ± 43 | 479 ± 96 | 697 ± 177 | GT | GT | GT | GT | GT | GT | GT |
| | 3 | 210 ± 18 | 324 ± 19 | 258 ± 36 | 200 ± 56 | 222 ± 90 | 354 ± 239 | GT | GT | GT | GT | GT | GT |
| | 10 | 211 ± 15 | 333 ± 16 | 295 ± 29 | 204 ± 26 | 142 ± 15 | 94 ± 14 | 66 ± 13 | 83 ± 35 | 208 ± 129 | 324 ± 219 | GT | GT |
| hIgG 8.8 vc_0101 | 3 | 212 ± 22 | 384 ± 35 | 567 ± 95 | 963 ± 204 | GT | GT | GT | GT | GT | GT | GT | GT |
| | 10 | 211 ± 20 | 354 ± 37 | 349 ± 48 | 198 ± 38 | 151 ± 31 | 165 ± 33 | 413 ± 128 | 922 ± 287 | GT | GT | GT | GT |

GT = group terminated due to large tumor size.

Example 17

Cysteine Mutant Generation for Site-Specific Conjugation

Site specific conjugation of linker-payloads to antibodies was done in order to improve homogeneous drug loading and avoid ADC subpopulations with altered antigen-binding or altered pharmacokinetics, often observed by conventional conjugation methods. One such site-specific conjugation method is to introduce cysteine residues at specific sites in the amino acid sequence of the target antibody. A number of amino acid positions in the constant heavy chain and constant light chain have been previously identified (see patent application U.S. Ser. No. 61/580,169) and were substituted with a cysteine residue at the specific amino acid position in the hu08v1.0/1.0 antibody. All cysteine mutations were constructed by site-directed mutagenesis or overlapping PCR based on pSMED-hu08v1.0 and pSEMN3-hu08v1.0. Below is the list of cysteine mutants derived from hu08v1.0/1.0 and the respective SEQ ID numbers (Table 21).

TABLE 21

| Antibody | | Mutation Site | aa SEQ ID NO: |
|---|---|---|---|
| Single mutant | HC | L443C | 28 |
| | | Q347C | 29 |
| | LC | kA111C | 30 |
| | | kK183C | 31 |
| | | kK188C | 32 |

TABLE 21-continued

| Antibody | | Mutation Site | aa SEQ ID NO: |
|---|---|---|---|
| Double mutant | HC | L443C/K392C | 33 |
| | | L443C/V422C | 34 |
| | HC/LC | L443C/kA111C | 28/30 |
| | | L443C/kK183C | 28/31 |
| | | Q347C/kA111C | 29/30 |
| | | Q347C/kK183C | 29/31 |

Example 18

Characterization of Cysteine Mutants

Cysteine mutants of hu08v1.0/1.0 were expressed either in transiently transfected HEK293 suspension cell cultures in freestyle 293 expression medium (Invitrogen, Carlsbad, Calif.) or in CHO cell culture stable pools. The antibodies were isolated from the cell culture medium by Protein A (ProA) chromatography under standard conditions. The column fractions were pooled and concentrated using a Millipore spin tube equipped with a 30,000 MWCO membrane. The protein was then loaded onto a size exclusion column (Superdex 200) equilibrated with PBS-CMF, pH 7.2. Peak fractions were pooled and concentrated using a Millipore spin tube equipped with a 30,000 MWCO membrane and finally filtered through a 0.22 um filter. Data is shown in Table 22 from transient expression and in Table 23 from CHO cell stable pools. Wild type hu08v1.0/1.0 and its cysteine derivatives have comparable final yield and purity after ProA capture, reach up to 99% purity after SEC and are stable after 2-3 cycles of freezing and thawing. This data demonstrates that the cysteine mutants maintain their expression profile and purification properties compared to hu08v1.0/1.0.

TABLE 22

| Antibody Name | Final Yield (mg/L) | Purity (ProA capture) | Purity (SEC) | F/T 2-3 cycles |
|---|---|---|---|---|
| hu08v1.0/1.0 | 26.5 | 97% | ND | stable |
| hu08v1.0/1.0-L443C | 56.0 | 94% | 99% | stable |
| hu08v1.0/1.0-Q347C | 30.0 | 97% | 99% | stable |
| hu08v1.0/1.0-A111C | 52.8 | 96.4% | 99% | stable |
| hu08v1.0/1.0-K183C | 44.4 | 97.0% | 99% | stable |
| hu08v1.0/1.0-K188C | 27.9 | 96.2% | 99% | stable |
| hu08v1.0/1.0-K392C/L443C | 28.0 | 85.0% | 99% | stable |
| hu08v1.0/1.0-V422C/L443C | 40.5 | 99.7% | ND | stable |
| hu08v1.0/1.0-Q347C/A111C | 31.4 | 96.6% | 99% | stable |
| hu08v1.0/1.0-L443C/A111C | 43.7 | ND | 99% | stable |
| hu08v1.0/1.0-Q347C/K183C | 29.0 | 97.2% | 99% | stable |
| hu08v1.0/1.0-L443C/K183C | 57.0 | ND | 99% | stable |

TABLE 23

| Antibody Name | Final Yield (mg/L) | Purity (ProA capture) | Purity (SEC) | F/T 2-3 cycles |
|---|---|---|---|---|
| hu08v1.0/1.0-Q347C | 26.74 | 94.0% | 99.0% | stable |
| hu08v1.0/1.0-K392C/L443C | 38.33 | 89.0% | 99.0% | stable |
| hu08v1.0/1.0 | 91.0 | 95% | 99.0% | stable |

Binding Properties of hu08v1.0/1.0 Cysteine Mutants.

The binding properties of the cysteine mutants to hIL-13-Rα2 were evaluated by a standard ELISA and a competition ELISA. The results show that all of the Cys mutants have a similar ED50 compared to wild type hu08v1.0/1.0 (Table 23). This conclusion was confirmed by a competition ELISA with biotinylated ch08. Table 24 demonstrates that all the Cys mutants have a similar IC50 as wild type hu08, indicating that the binding affinity is the same as wild type hu08. ch07 was used as a negative control.

TABLE 24

| | ED50 (nM) | IC50 (nM) |
|---|---|---|
| hu08 | 0.11 | 2.01 |
| hu08/L443C | 0.10 | 2.25 |
| hu08/L443C/K392C | 0.09 | 2.10 |
| hu08/L443C/V422C | 0.09 | 2.17 |
| hu08/L443C/kA111C | 0.12 | 2.32 |
| hu08/L443C/kK183C | 0.11 | 2.45 |
| hu08/Q347C | 0.10 | 2.07 |
| hu08/Q347C/kA111C | 0.10 | 2.44 |
| hu08/Q347C/kK183C | 0.13 | 2.41 |
| hu08/kA111C | 0.22 | 4.07 |
| hu08/kK183C | 0.11 | 2.47 |
| hu08/kK188C | 0.18 | 2.73 |
| hu08/kD185A | 0.108 | 2.364 |
| ch07 | 0.10 | 2.11 |

Thermal Stability of hu08v1.0/1.0 Cysteine Mutants.

The thermal stability of the anti-IL-13-Rα2 cysteine mutant mAbs was analyzed by Capillary Differential Scanning calorimetry (DSC) using a MicroCal's Capillary-DSC system equipped with an autosampler (Northampton, Mass.). A standard protocol was utilized. The heat capacity difference between the sample cell and reference cell was recorded and analyzed using the non-2 states model fit to 3 thermal transitions in the Origin7.0 software (OriginLab, Northampton, Mass.). A baseline thermogram was also generated with PBS buffer in both the sample and reference cells, and used for subtraction of any system heat not associated with protein denaturation. The results in Table 25 show that 2 single and 3 double cysteine mutant antibodies have comparable Tms as the parental hu08v1.0/1.0.

TABLE 25

| hu08v1.0/1.0 and its cysteine mutants | | Tm1 (° C.) CH2 | Tm2 (° C.) Fab | Tm3 (° C.) CH3 |
|---|---|---|---|---|
| Single Mutant | L443C | 72.85 ± 0.17 | 80.30 ± 0.02 | |
| | Q347C | 72.78 ± 0.15 | 80.18 ± 0.02 | |
| Double mutant | K392C/L443C | 74.09 ± 0.27 | 80.17 ± 0.22 | 78.14 ± 0.15 |
| | Q347C/kK183C | 72.59 ± 0.23 | 79.82 ± 0.12 | |
| | L443C/kK183C | 72.68 ± 0.12 | 79.93 ± 0.02 | 85.58 ± 0.18 |
| hu08v1.0/1.0 | | 73.48 ± 0.19 | 80.29 ± 0.02 | 85.48 ± 0.14 |

Thermal Stability of hu08v1.0/1.0 Cysteine Mutant ADCs

Wild type hu08v1.0/1.0 and 5 cysteine mutants were conjugated with vc-0101 as described in U.S. Provisional Patent Application 61/580,169. Thermal stability of all ADCs was measured by Capillary Differential Scanning calorimetry (DSC, see details above). As shown below in Table 26, the Tm1 of the wild type hu08v1.0/1.0 vc-0101 conjugate are significantly lower 5° C.) than its naked antibody (see Table 8). The Tm2 of the ADC is about 1-2° C. lower than naked antibody while the Tm3 is comparable. In terms of the hu08v1.0/1.0 cysteine mutants, Tm1, Tm2 and Tm3 of the vc-0101 conjugates are similar or slightly lower than 1-2° C.) its corresponding naked antibodies (see Table 25). This indicates that cysteine mutants are more thermal stable than wild type antibody after conjugation.

TABLE 26

| | Antibody | Conjugation linker payload | DAR | DSC (differential scanning calorimetry) | | |
|---|---|---|---|---|---|---|
| | | | | Tm1 (° C.) CH2 | Tm2 (° C.) Fab | Tm3 (° C.) CH3 |
| Single mutant | L443C | vc-0101 | 2.1 | 73.27 ± 0.19 | 79.29 ± 0.01 | |
| | Q347C | vc-0101 | 2.1 | 71.49 ± 0.09 | 79.16 ± 0.59 | 77.25 ± 0.59 |
| Double mutant | K392C/L443C | vc-0101 | 3.7 | 69.02 ± 0.07 | 78.83 ± 0.02 | 76.70 ± 0.11 |
| | Q347C/kK183C | vc-0101 | 4.3 | 70.15 ± 0.08 | 78.21 ± 0.12 | 76.20 ± 1.10 |
| | L443C/kK183C | vc-0101 | 4.0 | 71.30 ± 0.13 | 77.85 ± 0.02 | 84.16 ± 0.11 |
| hu08v1.0/1.0 | | vc-0101 | 3.2 | 68.42 ± 0.09 | 77.77 ± 0.10  79.45 ± 0.02 | 85.03 ± 0.07 |

Plasma and Glutathione Stability of hu08v1.0/1.0 Cysteine Mutants Conjugated with Vc-0101.

Sample preparation for GSH stability: 30 μg of a hu08-vc-0101 ADC or hu08-cys mutant-vc-0101 ADC in PBS was mixed with glutathione (GSH) solution to produce a final concentration of 0.5 mM GSH. The ADC in 0.5 mM GSH and control ADC (0 mM GSH) were incubated at 37° C. and sampled at 0, 3, and 6 days. TCEP (tris(2-carboxyethyl) phosphine) was used for reduction.

Sample preparation for mouse plasma stability: 90 μg ADC sample in PBS was mixed with mouse plasma, diluted 1:1 with 20% MPER (Mammalian Protein Extraction Reagent). The ADC/plasma samples were incubated at 37° C. and aliquots were taken at 0, 1, and 2 days and immune-precipitated with biotinylated recombinant hIL-13-Rα2 protein. The ADCs were eluted with 0.15% formic acid solution and neutralized with concentrated Tris HCl buffer to pH 7.8. Samples were deglycosylated by adding PNGaseF (Peptide: N-Glycosidase F) and reduced with TCEP.

LC/MS analysis procedure: Aliquots of the ADC/plasma and ADC/GSH stability samples were acidified by adding 0.1% formic acid solution with 10% acetonitrile and followed by LC/MS analysis on an Agilent 1100 capillary HPLC coupled with a Water Xevo G2 Q-TOF mass spectrometer. The analytes were loaded onto a Zorbax Poroshell 300SB C8 column (0.5 mm×75 mm, maintained at 80° C.) with 0.1% formic acid, and eluted using a gradient of 20-40% buffer B (80% acetonitrile, 18% 1-propanol, 2% water with 0.1% formic acid) at a flow rate of 20 μl/min over 5.5 minutes. Mass spectrometric detection was carried out in positive, sensitivity mode with capillary voltage set at 3.3 kV. Data analysis was performed with MaxEnt 1 function in MassLynx and intensities were used for loading calculation based on the following formula:

Loading=2*[LC1/(LC0+LC1)]+2*HC1/(HC0+HC1+HC2)]+4*HC2/(HC0+HC1+HC2)].

The ADCs of hu08 and its cys mutant conjugated with vc-0101 (from Table 26) were subjected to plasma and GSH stability assay. The results demonstrate that ADCs derived from cysteine mutants are more stable than the ADCs derived from the conventional conjugation technology (Table 27).

TABLE 27

| | Cys mutant-vc-0101 ADC | Plasma Stability % of loading Day 2 | GSH Stability % of loading Day 6 |
|---|---|---|---|
| Single mutant | L443C | 95.0% | 94.7% |
| | Q347C | 95.0% | 100.0% |
| Double mutant | K392C/L443C | 89.7% | 100.0% |
| | Q347C/kK183C | 81.6% | 97.4% |
| | L443C/kK183C | 91.9% | 86.8% |
| hu08 | | — | 62.5% |

Example 19

In Vitro Cytotoxicity Assay of Cys Mutant ADCs

Cell lines expressing the IL-13-Rα2 antigen or the IL-13-Rα2 negative cell line, H460, were cultured with increasing concentrations of hu08v1.0/1.0 cysteine mutants conjugated with vc-0101 or mc-3377. After four days, viability of each culture was assessed. $IC_{50}$ values were calculated by logistic non-linear regression and are presented in ng/mL (Tables 28a and 28b).

TABLE 28a

| ADC | | $IC_{50}$ (ng/mL) | |
|---|---|---|---|
| (variant-vc-0101) | DAR | PC3MM2 | A375 |
| Wild type hu08 | 3.2 | 1.93 ± 0.22 | 1.70 ± 0.98 |
| Q347C/kK183C | 4.3 | 1.77 ± 0.46 | 1.13 ± 0.15 |
| Q347C | 2.1 | 2.66 ± 0.60 | 1.65 ± 0.09 |
| L443C | 2.1 | 2.40 | 1.41 |
| K392C/L443C | 3.7 | 1.41 | 0.63 |
| L443C/kK183C | 4.0 | 1.72 | 0.83 |

TABLE 28b

| ADC | | $IC_{50}$ (ng Ab/mL) | | |
|---|---|---|---|---|
| (variant-mc-3377) | DAR | PC3MM2 | A375 | H460 |
| Wild type hu08 | 3.5 | 1.8 | 1.8 | >400000 |
| L443C | 2.3 | 3.9 | 3.3 | >400000 |
| K392C + L443C | 3.5 | 2.2 | 1.3 | >400000 |
| L443C + kK183C | 4 | 1.9 | 2.3 | >400000 |

Example 20

Subcutaneous Xenograft Models of Cys Mutant ADCs

Female, athymic (nude) mice were injected s.c. with PC3MM2 tumor cells. Mice with staged tumors, approximately 0.2 to 0.5 g (n=8 to 10 mice/treatment group) were administered a single dose at 1.5 or 4.5 mg/kg intravenously with normal saline (vehicle) cysteine mutants L443C-vc-0101, K392C/L443C-vc-0101, L443C/K183C-vc-0101, Q347C-vc-0101, or hAB-vc-0101, or 3, 6, and 12 mg/kg L443C-mc-3377, K392C/L443C-mc-3377, L443C/K183C-mc-3377. All ADCs were dosed based on Ab content. Tumors were measured at least once a week and their size ($mm^3$±SEM) was calculated as $mm^3$=0.5×(tumor width$^2$)× (tumor length).

The data in Table 29 indicates that L443C-vc-0101, K392C/L443C-vc-0101, L443C/K183C-vc-0101, and hu08-vc-0101, at both 1.5 mg/kg and 4.5 mg/kg all inhibit the growth of PC3MM2 xenografts compared to vehicle control group. L443C/K183-vc-0101 is the most potent compound tested in the experiment as indicated with the longest monitoring time at Day 70 before the termination of the group at the dose level of 4.5 mg/kg.

TABLE 29

| ADC | Single dose | \multicolumn{11}{c}{PC3MM2 xenograft, tumor volume (mm³ ± SEM)} | | | | | | | | | | |
|---|---|---|---|---|---|---|---|---|---|---|---|---|
| | | Day 0 | Day 3 | Day 6 | Day 10 | Day 13 | Day 18 | Day 21 | Day 32 | Day 42 | Day 53 | Day 63 | Day 70 |
| vehicle | | 341 ± 8 | 469 ± 25 | 681 ± 42 | 857 ± 60 | 1058 ± 115 | 1272 ± 167 | GT | GT | GT | GT | GT | GT |
| L443C vc-0101 | 1.5 | 353 ± 26 | 421 ± 51 | 429 ± 65 | 428 ± 65 | 472 ± 93 | 567 ± 133 | 629 ± 176 | GT | GT | GT | GT | GT |
| K392C + L443C vc-0101 | 1.5 | 343 ± 10 | 441 ± 31 | 417 ± 22 | 344 ± 23 | 356 ± 27 | 479 ± 57 | 565 ± 61 | 1219 ± 154 | 1411 ± 157 | GT | GT | GT |
| L443C + Kk183C vc-0101 | 1.5 | 350 ± 18 | 431 ± 35 | 453 ± 49 | 396 ± 44 | 390 ± 49 | 464 ± 46 | 446 ± 54 | 842 ± 171 | GT | GT | GT | GT |
| hu08-vc-0101 | 1.5 | 335 ± 16 | 451 ± 28 | 468 ± 47 | 439 ± 65 | 461 ± 86 | 600 ± 116 | 680 ± 135 | 1502 ± 406 | GT | GT | GT | GT |
| L443C-vc-0101 | 4.5 | 358 ± 8 | 397 ± 13 | 334 ± 24 | 199 ± 25 | 164 ± 17 | 143 ± 23 | 124 ± 20 | 156 ± 47 | 242 ± 86 | 509 ± 193 | 618 ± 232 | GT |
| K392C + L443C-vc-0101 | 4.5 | 351 ± 19 | 363 ± 27 | 353 ± 28 | 196 ± 10 | 169 ± 9 | 136 ± 17 | 118 ± 27 | 230 ± 98 | 318 ± 142 | 553 ± 235 | GT | GT |
| L443C + Kk183C-vc-0101 | 4.5 | 343 ± 17 | 417 ± 32 | 397 ± 44 | 219 ± 18 | 156 ± 18 | 121 ± 8 | 93 ± 10 | 105 ± 27 | 175 ± 77 | 461 ± 221 | 423 ± 134 | 694 ± 222 |

GT = group terminated due to large tumor size.

The data in Table 30 indicates that Q347C-vc-0101 and Q347C/K183C-vc-0101, all inhibit the growth of PC3MM2 xenografts at both 1.5 mg/kg and 4.5 mg/kg compared to vehicle control group. Further, the data demonstrates that hu08MAC-0101 inhibits the growth of PC3MM2 xenografts at 1.5 mg/kg compared to the vehicle control group. The most potent compound was Q347C/K183C-vc-0101 as indicated at the dose level of 4.5 mg/kg with the longest monitoring time of Day 77. These results show that site-specific vc-0101 conjugates are comparable or superior in efficacy to wild-type hu08-vc-0101 conjugates.

TABLE 30

| ADC | single dose | \multicolumn{9}{c}{PC3MM2 xenograft, tumor volume (mm³ ± SEM)} | | | | | | | | |
|---|---|---|---|---|---|---|---|---|---|---|
| | | Day 0 | Day 5 | Day 8 | Day 12 | Day 15 | Day 20 | Day 30 | Day 41 | Day 55 | Day 77 |
| Vehicle | 0 | 325 ± 9 | 590 ± 41 | 782 ± 79 | 1140 ± 142 | GT | GT | GT | GT | GT | GT |
| Q347 + kC183-vc-0101 | 1.5 | 337 ± 17 | 383 ± 39 | 324 ± 35 | 347 ± 46 | 381 ± 63 | 481 ± 89 | 770 ± 121 | GT | GT | GT |
| Q347-vc-0101 | 1.5 | 333 ± 11 | 341 ± 14 | 308 ± 32 | 309 ± 39 | 352 ± 54 | 473 ± 79 | 757 ± 238 | GT | GT | GT |
| hu08MAC-0101 | 1.5 | 328 ± 49 | 393 ± 96 | 352 ± 106 | 432 ± 124 | 556 ± 236 | 732 ± 305 | GT | GT | GT | GT |
| Q347 + kC183-vc-0101 | 4.5 | 336 ± 17 | 252 ± 19 | 171 ± 18 | 145 ± 13 | 128 ± 8 | 88 ± 14 | 113 ± 37 | 28 ± 28 | 75 ± 75 | 128 ± 128 |
| Q347-vc-0101 | 4.5 | 338 ± 16 | 278 ± 28 | 176 ± 20 | 136 ± 16 | 130 ± 30 | 128 ± 41 | 267 ± 112 | GT | GT | GT |
| hu08-vc-0101 | 1.5 | 333 ± 12 | 431 ± 40 | 281 ± 25 | 299 ± 32 | 362 ± 47 | 450 ± 58 | 956 ± 166 | GT | GT | GT |

GT = group terminated due to large tumor size

The data in Table 31 a and b indicates that L443C-mc-3377, K392C/L443C-mc-3377, L443C/K183C-mc-3377, and hu08-mc-3377 caused tumor regression in a dose-dependent manner compared to vehicle control group. L443C/K183C-mc-3377 was the most potent compound tested in the experiment as indicated with the small average tumor size at 12 mg/kg dose level compared to other compounds. In addition, there were 6 out of 8 animals without measurable tumors from the group treated with L443C/K183C-mc3377 at 12 mg/kg at Day 60.

TABLE 31a

| ADC | single dose | Day 0 | Day 7 | Day 14 | Day 21 | Day 28 | Day 38 | Day 45 | Day 50 | Day 60 |
|---|---|---|---|---|---|---|---|---|---|---|
| | Dose (mg/kg) | PC3MM2 xenograft, tumor volume (mm³ +/− SEM) | | | | | | | | |
| vehicle | 0 | 339 ± 19 | 1021 ± 112 | 1737 ± 194 | GT | GT | GT | GT | GT | GT |
| C443 mc_3377 | 3 | 341 ± 24 | 350 ± 61 | 461 ± 82 | 601 ± 139 | 954 ± 250 | GT | GT | GT | GT |
| | 6 | 333 ± 31 | 352 ± 51 | 280 ± 54 | 366 ± 103 | 501 ± 147 | 1030 ± 307 | GT | GT | GT |
| | 12 | 338 ± 27 | 293 ± 45 | 177 ± 39 | 153 ± 22 | 278 ± 52 | 559 ± 117 | 752 ± 179 | 871 ± 267 | GT |
| C392 + C443 mc_3377 | 3 | 341 ± 26 | 387 ± 64 | 462 ± 132 | 496 ± 197 | 977 ± 381 | GT | GT | GT | GT |
| | 6 | 335 ± 31 | 237 ± 37 | 123 ± 37 | 133 ± 48 | 179 ± 85 | 469 ± 193 | 606 ± 252 | 768 ± 334 | GT |
| | 12 | 340 ± 23 | 312 ± 40 | 213 ± 45 | 150 ± 49 | 208 ± 79 | 261 ± 94 | 507 ± 242 | 695 ± 319 | GT |
| C443 + kC183 mc_3377 | 3 | 343 ± 27 | 386 ± 50 | 336 ± 60 | 452 ± 125 | 809 ± 245 | GT | GT | GT | GT |
| | 6 | 332 ± 28 | 311 ± 58 | 189 ± 32 | 135 ± 27 | 129 ± 37 | 237 ± 101 | 385 ± 185 | 491 ± 271 | GT |
| | 12 | 336 ± 32 | 238 ± 44 | 103 ± 30 | 49 ± 25 | 65 ± 26 | 61 ± 52 | 70 ± 55 | 109 ± 87 | 158 ± 123 |

TABLE 31 b

| ADC | single dose | Day 0 | Day 7 | Day 14 | Day 21 | Day 28 | Day 38 | Day 45 | Day 50 | Day 60 |
|---|---|---|---|---|---|---|---|---|---|---|
| | Dose (mg/kg) | PC3MM2 xenograft, tumor volume (mm³ +/− SEM) | | | | | | | | |
| mc_3377 | 3 | 336 ± 29 | 340 ± 33 | 285 ± 75 | 436 ± 131 | 732 ± 265 | GT | GT | GT | GT |
| | 6 | 327 ± 35 | 231 ± 45 | 89 ± 29 | 30 ± 16 | 84 ± 25 | 184 ± 42 | 285 ± 108 | 402 ± 158 | GT |
| | 12 | 340 ± 28 | 180 ± 14 | 81 ± 28 | 52 ± 28 | 76 ± 45 | 171 ± 102 | 282 ± 179 | 354 ± 233 | 442 ± 328 |

GT = group terminated due to large tumor size

Example 21

Site-Specific Conjugation with MAC Technology

A method of preparing a multifunctional antibody conjugate (MAC) comprising an antibody or antigen binding fragment thereof has been described previously (WO2012/007896 and U.S. Ser. No. 61/584,675). An aspect of the present invention is a method of preparing a MAC utilizing an antibody or antigen binding fragment thereof that specifically binds to human IL-13Rα2 wherein the antibody has the mutation D185A at position 185 of the LC as shown in SEQ ID NO: 52, and the antibody is covalently conjugated to at least one drug moiety through a linker attached to a side chain of K188 of the LC of SEQ ID NO:49; said method comprising: covalently attaching the drug moiety using a PFP (Pentafluorophenyl) ester and reacting the Effector Moiety-linker-leaving group complex so formed with the antibody at a molar ratio of between about 3.5:1 to about 4.5:1 of drug moiety:antibody. In some aspects, the molar ratio is about 3.7:1 to about 4.3:1. The MAC described herein is designated as hu08MAC-0101 and comprises the mutation D185A of the LC of SEQ ID NO: 52; and, the drug moiety 0101 (Example 13), which is conjugated to a side chain of the lysine residue at position 188 (K188) of the LC of SEQ ID NO: 52. In vitro activity of hu08MAC-0101 is shown in Table 17 (Example 15). In vivo activity in the PC3MM2 xenograft model is shown in Table 30 (Example 20).

What is claimed:

1. An isolated antibody or antigen-binding fragment thereof that specifically binds to human IL-13 receptor alpha 2 (IL-13-Rα2) wherein the antibody comprises a heavy chain variable region and a light chain variable region comprising
a heavy chain variable region comprising CDR1, CDR2, and CDR3 of SEQ ID NO: 1 and a light chain variable region comprising a CDR1, CDR2, and CDR3 of SEQ ID NO: 5.

2. An antibody-drug conjugate comprising a cytotoxic agent conjugated to the antibody or antigen-binding fragment thereof of claim 1.

3. A nucleic acid that encodes the antibody or antigen-binding fragment thereof of claim 1.

4. A vector comprising the nucleic acid of claim 3.

5. An isolated host cell comprising the vector of claim 4.

6. A process for producing an antibody comprising cultivating the isolated host cell of claim 5 and recovering the antibody from a cell culture.

7. An isolated antibody or antigen-binding fragment thereof that specifically binds to human IL-13-Rα2, wherein the antibody comprises:
a heavy chain CDR1 comprising SEQ ID NO: 2;
a heavy chain CDR2 comprising SEQ ID NO: 3;
a heavy chain CDR3 comprising SEQ ID NO: 4;
a light chain CDR1 comprising SEQ ID NO: 6;
a light chain CDR2 comprising SEQ ID NO: 7 and
a light chain CDR3 comprising SEQ ID NO: 8.

8. The isolated antibody or antigen-binding fragment thereof of claim 7, wherein said isolated antibody comprises the heavy chain variable region set forth in the amino acid sequence SEQ ID NO: 1.

9. The isolated antibody or antigen-binding fragment thereof of claim 7, wherein said isolated antibody comprises the light chain variable region set forth in the amino acid sequence SEQ ID NO: 5.

10. The isolated antibody or antigen-binding fragment thereof of claim 7, wherein said antibody comprises a heavy chain comprising the amino acid sequence of SEQ ID NO: 50.

11. The isolated antibody or antigen-binding fragment thereof of claim 1, wherein said antibody comprises a light chain comprising the amino acid sequence of SEQ ID NO: 51.

12. An antibody-drug conjugate of the formula:

Ab-(L-D)

wherein:
(a) Ab is an isolated antibody or antigen-binding fragment thereof that specifically binds to human IL-13-Rα2 wherein the antibody comprises a heavy chain variable region and a light chain variable region comprising a heavy chain variable region comprising CDR1, CDR2, and CDR3 of SEQ ID NO: 1 and a light chain variable region comprising a CDR1, CDR2, and CDR3 of SEQ ID NO: 5; and
(b) L-D is a linker-drug moiety, wherein L is a linker, and D is a drug.

13. The antibody-drug conjugate of claim 12 wherein L is selected from the group consisting of Maleimidocaproyl-Val-Cit-PABA (vc), maleimidocaproyl (mc), and maleimide-propylene glycol (MalPeg).

14. The antibody-drug conjugate of claim 12 wherein D is selected from the group consisting of 0101, 3377, 0131, 6121, 3906, 6780 and 8261.

15. The antibody-drug conjugate of claim 12 wherein L-D is selected from the group consisting of vc-0101 and mc-3377.

16. The antibody-drug conjugate of claim 12, wherein Ab comprises a heavy chain variable region and a light chain variable region comprising
a heavy chain variable region comprising a CDR1, CDR2, and CDR3 of SEQ ID NO: 1 and a light chain variable region comprising a CDR1, CDR2, and CDR3 of sequence of SEQ ID NO: 5.

17. The antibody-drug conjugate of claim 12, wherein Ab comprises a heavy chain variable region and a light chain variable region comprising:
a heavy chain CDR1 comprising SEQ ID NO: 2;
a heavy chain CDR2 comprising SEQ ID NO: 3;
a heavy chain CDR3 comprising SEQ ID NO: 4;
a light chain CDR1 comprising SEQ ID NO: 6;
a light chain CDR2 comprising SEQ ID NO: 7 and
a light chain CDR3 comprising SEQ ID NO: 8.

18. An antibody-drug conjugate of the formula:

Ab-(L-D)

wherein:
(a) Ab is an isolated antibody or antigen-binding fragment thereof of claim 1; and
(b) L-D is a linker-drug moiety of vc-0101.

19. An antibody-drug conjugate of the formula:

Ab-(L-D)

wherein:
(a) Ab is an isolated antibody or antigen-binding fragment thereof of claim 1; and
(b) L-D is a linker-drug moiety of mc-3377.

20. A pharmaceutical composition comprising the antibody-drug conjugate of claim 12 and a pharmaceutically acceptable carrier.

21. A method of treating an IL-13-Rα2 expressing cancer in to patient in need thereof comprising administering to said patient the antibody-drug conjugate of claim 12.

22. The method of claim 21 wherein said cancer is selected from the group consisting of lung, colon, stomach, pancreatic, ovarian, malignant gliomas, and melanoma.

23. A process for producing an anti-IL-13-Rα2 antibody-drug conjugate of claim 12 comprising:
(a) linking a linker selected from the group consisting of vc, mc and MalPeg to the drug;
(b) conjugating said linker-drug moiety to the antibody; and,
(c) purifying the antibody-drug conjugate.

\* \* \* \* \*